US011078287B2

(12) United States Patent
Bhinder et al.

(10) Patent No.: US 11,078,287 B2
(45) Date of Patent: Aug. 3, 2021

(54) BINDING AGONIST FOR TREATMENT OF NEUROLOGICAL AND OTHER DISORDERS

(71) Applicant: GlaxoSmithKline Intellectual Property Development Limited, Middlesex (GB)

(72) Inventors: Tejinder Kaur Bhinder, Stevenage (GB); Chong Ding, Shanghai (CN); Xu Feng, Shanghai (CN); Wenqing Jiang, Shanghai (CN); Alan Peter Lewis, Stevenage (GB); Yingli Ma, Shanghai (CN); Guhan Nagappan, Shanghai (CN); Radha Shah Parmar, Stevenage (GB); Yangsheng Qiu, Shanghai (CN); Liuqing Yang, Shanghai (CN); Qing Zhang, Shanghai (CN); Yanjiao Zhou, Shanghai (CN)

(73) Assignee: GLAXOSMITHKLINE INTELLECTUAL PROPERTY DEVELOPMENT LIMITED, Middlesex (GB)

(*) Notice: Subject to any disclaimer, the term of this patent is extended or adjusted under 35 U.S.C. 154(b) by 273 days.

(21) Appl. No.: 15/776,493

(22) PCT Filed: Nov. 15, 2016

(86) PCT No.: PCT/EP2016/077644
§ 371 (c)(1),
(2) Date: May 16, 2018

(87) PCT Pub. No.: WO2017/085035
PCT Pub. Date: May 26, 2017

(65) Prior Publication Data
US 2020/0165345 A1  May 28, 2020

(30) Foreign Application Priority Data

Nov. 17, 2015  (WO) ................ PCT/CN2015/094778
Aug. 16, 2016  (WO) ................ PCT/CN2016/095545
Nov. 8, 2016  (GB) .................................. 1618814.6

(51) Int. Cl.
*A61K 39/395* (2006.01)
*C07K 16/28* (2006.01)
*A61P 25/00* (2006.01)
*A61P 27/16* (2006.01)
*A61K 39/00* (2006.01)

(52) U.S. Cl.
CPC .......... *C07K 16/2863* (2013.01); *A61P 25/00* (2018.01); *A61P 27/16* (2018.01); *A61K 2039/505* (2013.01); *C07K 16/2878* (2013.01); *C07K 2317/24* (2013.01); *C07K 2317/33* (2013.01); *C07K 2317/565* (2013.01); *C07K 2317/75* (2013.01)

(58) Field of Classification Search
CPC ............ C07K 16/2863; C07K 16/2878; A61K 39/3955; A61P 25/00; A61P 27/16
See application file for complete search history.

(56) References Cited

U.S. PATENT DOCUMENTS 9,914,781 B1  3/2018  Bhinder et al.
2009/0291897 A1  11/2009  Lin et al.

FOREIGN PATENT DOCUMENTS

| WO | WO 2006/133164 A2 | 12/2006 |
| WO | WO 2008/058127 A2 | 5/2008 |
| WO | 2008078179 A1 | 7/2008 |
| WO | WO 2009/053442 A1 | 4/2009 |
| WO | 2009092049 A1 | 7/2009 |
| WO | 2010086828 A2 | 8/2010 |
| WO | 2011103667 A1 | 9/2011 |
| WO | 2011103668 A1 | 9/2011 |
| WO | 2012156505 A1 | 11/2012 |

OTHER PUBLICATIONS

Jackowski, British Journal of Neurosurgery 9 (1995): 303-317.*
Sung-Wuk Jang, et al., Deoxygedunin, a Natural Product with Potent Neurotrophic Activity in Mice, Plos One, 5(7):e11528 (2010).
Qian MD, et al., Novel agonist monoclonal antibodies activate TrkB receptors and demonstrate potent neurotrophic activities, Journal of Neuroscience, Society for Neuroscience, 26(37):9349-9403 (2006), ISSN: 0270-6474.
Hu, et al., Neurotrophic effect of a novel TrkB agonist on retinal ganglion cells, Investigative Ophthalmology & Visual Science—IOVS, Association for Research in Vision and Ophthalmology, 51(3):1747-1754 (2010), ISN: 0146-0404.
Gab Seok Kim, et al., TrkB Agonist Antibody Pretreatment Enhances Neuronal Survival and Long-Term Sensory Motor Function Following Hypoxic Ischemic Injury in Neonatal Rats, Plos One, 9(2):e88962 (2014).
Yujing Bai, et al., An Agonistic TrkB mAb Causes sustained TrkB Activation, Delays RGC Death, and Protects the Retinal Structure in Optic Nerve Axotomy and in Glaucoma, Investigative Ophthalmology & Visual Science, 51(9):4722-4731 (2010), ISSN: 1552-5783.
Ruth L Naylor, et al., A Discrete Domain of the Human TrkB Receptor Defines the Binding Sites for BDNF and NT-4, Biochemical and Biophysical Research Communications, 291(3):501-507 (2002), ISSN: 0006-291X.
Alan H. Nagahara, et al., Potential Therapeutic uses of BDNF in Neurological and Psychiatric disorders, Nature Reviews, Drug Discovery, 10(3):209-219 (2011), ISSN: 1474-1776.
Todd, et al., A Monoclonal Antibody TrkB Receptor Agonist as a Potential Therapeutic for Huntington's Disease, PLOS One, 9(2):e87923 (2014).

(Continued)

Primary Examiner — Robert C Hayes
(74) Attorney, Agent, or Firm — Shan Liu; Fang Qian

(57) ABSTRACT

The present invention relates to TrkB binding agonists, and to the use of such agonists in the treatment of neurological disorders and other disorders. The present invention also relates to specific TrkB binding agonists comprising CDRs, variable regions, heavy and light chains, and variant sequences thereof.

18 Claims, 10 Drawing Sheets

Specification includes a Sequence Listing.

(56) References Cited

OTHER PUBLICATIONS

Meltser, et al., *Curr Biology*, "TrkB mediated protection against circadian sensitivity to noise trauma in the murine cochlea," 17:24(6):658-663 (2014).

Yu, et al., *Biochem Biophys Res Commun.*, "7,8,3'—Trihydroxyflavone, a potent small molecule TrkB receptor agonist, protects spiral ganglion neurons from degeneration both in vitro and in vivo," 8:422(3):387-392 (2012).

\* cited by examiner

SEQUENCE LISTING

<160> NUMBER OF SEQ ID NOS: 88

<210> SEQ ID NO 1
<211> LENGTH: 399
<212> TYPE: PRT
<213> ORGANISM: Artificial
<220> FEATURE:
<223> OTHER INFORMATION: Human TrkB-Extracellular Domain

<400> SEQUENCE: 1

Cys Pro Thr Ser Cys Lys Cys Ser Ala Ser Arg Ile Trp Cys Ser Asp
1               5                   10                  15

Pro Ser Pro Gly Ile Val Ala Phe Pro Arg Leu Glu Pro Asn Ser Val
            20                  25                  30

Asp Pro Glu Asn Ile Thr Glu Ile Phe Ile Ala Asn Gln Lys Arg Leu
        35                  40                  45

Glu Ile Ile Asn Glu Asp Val Glu Ala Tyr Val Gly Leu Arg Asn
    50                  55                  60

Leu Thr Ile Val Asp Ser Gly Leu Lys Phe Val Ala His Lys Ala Phe
65                  70                  75                  80

Leu Lys Asn Ser Asn Leu Gln His Ile Asn Phe Thr Arg Asn Lys Leu
            85                  90                  95

Thr Ser Leu Ser Arg Lys His Phe Arg His Leu Asp Leu Ser Glu Leu
            100                 105                 110

Ile Leu Val Gly Asn Pro Phe Thr Cys Ser Cys Asp Ile Met Trp Ile
            115                 120                 125

Lys Thr Leu Gln Glu Ala Lys Ser Ser Pro Asp Thr Gln Asp Leu Tyr
130                 135                 140

Cys Leu Asn Glu Ser Ser Lys Asn Ile Pro Leu Ala Asn Leu Gln Ile
145                 150                 155                 160

Pro Asn Cys Gly Leu Pro Ser Ala Asn Leu Ala Ala Pro Asn Leu Thr
                165                 170                 175

Val Glu Glu Gly Lys Ser Ile Thr Leu Ser Cys Ser Val Ala Gly Asp
                180                 185                 190

Pro Val Pro Asn Met Tyr Trp Asp Val Gly Asn Leu Val Ser Lys His
            195                 200                 205

Met Asn Glu Thr Ser His Thr Gln Gly Ser Leu Arg Ile Thr Asn Ile
210                 215                 220

Ser Ser Asp Asp Ser Gly Lys Gln Ile Ser Cys Val Ala Glu Asn Leu
225                 230                 235                 240

Val Gly Glu Asp Gln Asp Ser Val Asn Leu Thr Val His Phe Ala Pro
                245                 250                 255

Thr Ile Thr Phe Leu Glu Ser Pro Thr Ser Asp His His Trp Cys Ile
                260                 265                 270

Pro Phe Thr Val Lys Gly Asn Pro Lys Pro Ala Leu Gln Trp Phe Tyr
            275                 280                 285

Asn Gly Ala Ile Leu Asn Glu Ser Lys Tyr Ile Cys Thr Lys Ile His
            290                 295                 300

Val Thr Asn His Thr Glu Tyr His Gly Cys Leu Gln Leu Asp Asn Pro
305                 310                 315                 320

Thr His Met Asn Asn Gly Asp Tyr Thr Leu Ile Ala Lys Asn Glu Tyr
                325                 330                 335

Gly Lys Asp Glu Lys Gln Ile Ser Ala His Phe Met Gly Trp Pro Gly
            340                 345                 350

Ile Asp Asp Gly Ala Asn Pro Asn Tyr Pro Asp Val Ile Tyr Glu Asp
            355                 360                 365

Tyr Gly Thr Ala Ala Asn Asp Ile Gly Asp Thr Thr Asn Arg Ser Asn
            370                 375                 380

Glu Ile Pro Ser Thr Asp Val Thr Asp Lys Thr Gly Arg Glu His
385                 390                 395

<210> SEQ ID NO 2

-continued

```
<211> LENGTH: 822
<212> TYPE: PRT
<213> ORGANISM: Human

<400> SEQUENCE: 2

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile
370                 375                 380

Asp Asp Gly Ala Asn Pro Asn Tyr Pro Asp Val Ile Tyr Glu Asp Tyr
```

-continued

```
                385                 390                 395                 400
        Gly Thr Ala Ala Asn Asp Ile Gly Asp Thr Thr Asn Arg Ser Asn Glu
                        405                 410                 415

Ile Pro Ser Thr Asp Val Thr Asp Lys Thr Gly Arg Glu His Leu Ser
                        420                 425                 430

Val Tyr Ala Val Val Ile Ala Ser Val Val Gly Phe Cys Leu Leu
                        435                 440                 445

Val Met Leu Phe Leu Leu Lys Leu Ala Arg His Ser Lys Phe Gly Met
                    450                 455                 460

Lys Gly Pro Ala Ser Val Ile Ser Asn Asp Asp Ser Ala Ser Pro
        465                 470                 475                 480

Leu His His Ile Ser Asn Gly Ser Asn Thr Pro Ser Ser Glu Gly
                                485                 490                 495

Gly Pro Asp Ala Val Ile Ile Gly Met Thr Lys Ile Pro Val Ile Glu
                        500                 505                 510

Asn Pro Gln Tyr Phe Gly Ile Thr Asn Ser Gln Leu Lys Pro Asp Thr
                        515                 520                 525

Phe Val Gln His Ile Lys Arg His Asn Ile Val Leu Lys Arg Glu Leu
                    530                 535                 540

Gly Glu Gly Ala Phe Gly Lys Val Phe Leu Ala Glu Cys Tyr Asn Leu
        545                 550                 555                 560

Cys Pro Glu Gln Asp Lys Ile Leu Val Ala Val Lys Thr Leu Lys Asp
                        565                 570                 575

Ala Ser Asp Asn Ala Arg Lys Asp Phe His Arg Glu Ala Glu Leu Leu
                        580                 585                 590

Thr Asn Leu Gln His Glu His Ile Val Lys Phe Tyr Gly Val Cys Val
                    595                 600                 605

Glu Gly Asp Pro Leu Ile Met Val Phe Glu Tyr Met Lys His Gly Asp
        610                 615                 620

Leu Asn Lys Phe Leu Arg Ala His Gly Pro Asp Ala Val Leu Met Ala
                        625                 630                 635                 640

Glu Gly Asn Pro Pro Thr Glu Leu Thr Gln Ser Gln Met Leu His Ile
                        645                 650                 655

Ala Gln Gln Ile Ala Ala Gly Met Val Tyr Leu Ala Ser Gln His Phe
                    660                 665                 670

Val His Arg Asp Leu Ala Thr Arg Asn Cys Leu Val Gly Glu Asn Leu
                675                 680                 685

Leu Val Lys Ile Gly Asp Phe Gly Met Ser Arg Asp Val Tyr Ser Thr
                        690                 695                 700

Asp Tyr Tyr Arg Val Gly Gly His Thr Met Leu Pro Ile Arg Trp Met
        705                 710                 715                 720

Pro Pro Glu Ser Ile Met Tyr Arg Lys Phe Thr Thr Glu Ser Asp Val
                        725                 730                 735

Trp Ser Leu Gly Val Val Leu Trp Glu Ile Phe Thr Tyr Gly Lys Gln
                    740                 745                 750

Pro Trp Tyr Gln Leu Ser Asn Asn Glu Val Ile Glu Cys Ile Thr Gln
                        755                 760                 765

Gly Arg Val Leu Gln Arg Pro Arg Thr Cys Pro Gln Glu Val Tyr Glu
                        770                 775                 780

Leu Met Leu Gly Cys Trp Gln Arg Glu Pro His Met Arg Lys Asn Ile
        785                 790                 795                 800

Lys Gly Ile His Thr Leu Leu Gln Asn Leu Ala Lys Ala Ser Pro Val
                        805                 810                 815
```

Tyr Leu Asp Ile Leu Gly
            820

<210> SEQ ID NO 3
<211> LENGTH: 11
<212> TYPE: PRT
<213> ORGANISM: Artificial
<220> FEATURE:
<223> OTHER INFORMATION: 1G11 and humanised 1G11 CDR L2 (Kabat, Chothia,
      AbM)

<400> SEQUENCE: 3

Arg Ala Ser Gln Arg Ile Ser Asn Asn Leu His
1               5                   10

<210> SEQ ID NO 4
<211> LENGTH: 7
<212> TYPE: PRT
<213> ORGANISM: Artificial
<220> FEATURE:
<223> OTHER INFORMATION: 1G11 and humanised 1G11 CDR L2 (Kabat, Chothia,
      AbM)

<400> SEQUENCE: 4

Tyr Val Ser Gln Ser Ile Ser
1               5

<210> SEQ ID NO 5
<211> LENGTH: 9
<212> TYPE: PRT
<213> ORGANISM: Artificial
<220> FEATURE:
<223> OTHER INFORMATION: 1G11 and humanised 1G11 CDR L3 (Kabat, Chothia,
      AbM)

<400> SEQUENCE: 5

Gln Gln Ser Asn Ser Trp Pro Leu Thr
1               5

<210> SEQ ID NO 6
<211> LENGTH: 5
<212> TYPE: PRT
<213> ORGANISM: Artificial
<220> FEATURE:
<223> OTHER INFORMATION: 1G11 and humanised 1G11 CDR H1 (Kabat)

<400> SEQUENCE: 6

Ser Tyr Tyr Ile Asn
1               5

<210> SEQ ID NO 7
<211> LENGTH: 15
<212> TYPE: PRT
<213> ORGANISM: Artificial
<220> FEATURE:
<223> OTHER INFORMATION: 1G11 and humanised 1G11 CDR H2 (Kabat)

<400> SEQUENCE: 7

Arg Ile Ala Pro Gly Asn Thr Tyr Tyr Asn Glu Ile Phe Lys Gly
1               5                   10                  15

<210> SEQ ID NO 8
<211> LENGTH: 9
<212> TYPE: PRT
<213> ORGANISM: Artificial
<220> FEATURE:
<223> OTHER INFORMATION: 1G11 and humanised 1G11 CDR H3 (Kabat, Chothia, AbM)

<400> SEQUENCE: 8

Arg Gly Tyr Glu Gly Ala Leu Asp Tyr
1               5

<210> SEQ ID NO 9
<211> LENGTH: 17
<212> TYPE: PRT
<213> ORGANISM: Artificial
<220> FEATURE:
<223> OTHER INFORMATION: 3A3 CDR L1 (Kabat)

<400> SEQUENCE: 9

Lys Ser Ser Gln Ser Leu Leu Tyr Ser Gly Asn Gln Lys Asn Tyr Leu
1               5                   10                  15

Ala

<210> SEQ ID NO 10
<211> LENGTH: 7
<212> TYPE: PRT
<213> ORGANISM: Artificial
<220> FEATURE:
<223> OTHER INFORMATION: 3A3 CDR L2 (Kabat)

<400> SEQUENCE: 10

Trp Ala Ser Thr Arg Glu Ser
1               5

<210> SEQ ID NO 11
<211> LENGTH: 9
<212> TYPE: PRT
<213> ORGANISM: Artificial
<220> FEATURE:
<223> OTHER INFORMATION: 3A3 CDR L3 (Kabat)

<400> SEQUENCE: 11

Gln Gln Tyr Tyr Ser Tyr Pro Tyr Thr
1               5

<210> SEQ ID NO 12
<211> LENGTH: 5
<212> TYPE: PRT
<213> ORGANISM: Artificial
<220> FEATURE:
<223> OTHER INFORMATION: 3A3 CDR H1 (Kabat)

<400> SEQUENCE: 12

Ser Tyr Trp Met His
1               5

<210> SEQ ID NO 13
<211> LENGTH: 17
<212> TYPE: PRT
<213> ORGANISM: Artificial
<220> FEATURE:
<223> OTHER INFORMATION: 3A3 CDR H2 (Kabat)

<400> SEQUENCE: 13

Tyr Ile Asn Pro Ser Thr Gly Tyr Thr Asp Tyr Asn Gln Lys Phe Lys
1               5                   10                  15

Asp

<210> SEQ ID NO 14
<211> LENGTH: 6

```
<212> TYPE: PRT
<213> ORGANISM: Artificial
<220> FEATURE:
<223> OTHER INFORMATION: 3A3 CDR H3 (Kabat)

<400> SEQUENCE: 14

Ser Arg Ala Ala Arg Tyr
1               5

<210> SEQ ID NO 15
<211> LENGTH: 12
<212> TYPE: PRT
<213> ORGANISM: Artificial
<220> FEATURE:
<223> OTHER INFORMATION: 8E5 CDR L1 (Kabat)

<400> SEQUENCE: 15

Arg Ala Ser Ser Ser Val Ser Ser Ser Tyr Leu His
1               5                   10

<210> SEQ ID NO 16
<211> LENGTH: 7
<212> TYPE: PRT
<213> ORGANISM: Artificial
<220> FEATURE:
<223> OTHER INFORMATION: 8E5 CDR L2 (Kabat)

<400> SEQUENCE: 16

Ser Thr Ser Asn Leu Ala Ser
1               5

<210> SEQ ID NO 17
<211> LENGTH: 9
<212> TYPE: PRT
<213> ORGANISM: Artificial
<220> FEATURE:
<223> OTHER INFORMATION: 8E5 CDR L3 (Kabat)

<400> SEQUENCE: 17

Gln Gln Tyr Ser Gly Tyr Pro Leu Thr
1               5

<210> SEQ ID NO 18
<211> LENGTH: 5
<212> TYPE: PRT
<213> ORGANISM: Artificial
<220> FEATURE:
<223> OTHER INFORMATION: 8E5 CDR H1 (Kabat)

<400> SEQUENCE: 18

Thr Tyr Gly Met Ser
1               5

<210> SEQ ID NO 19
<211> LENGTH: 17
<212> TYPE: PRT
<213> ORGANISM: Artificial
<220> FEATURE:
<223> OTHER INFORMATION: 8E5 CDR H2 (Kabat)

<400> SEQUENCE: 19

Thr Val Ser Thr Gly Gly Thr Tyr Thr Tyr Tyr Pro Asp Ser Val Lys
1               5                   10                  15

Gly

<210> SEQ ID NO 20
```

```
<211> LENGTH: 7
<212> TYPE: PRT
<213> ORGANISM: Artificial
<220> FEATURE:
<223> OTHER INFORMATION: 8E5 CDR H3 (Kabat)

<400> SEQUENCE: 20

Gly Gly Tyr Ser Phe Ala Tyr
1               5

<210> SEQ ID NO 21
<211> LENGTH: 15
<212> TYPE: PRT
<213> ORGANISM: Artificial
<220> FEATURE:
<223> OTHER INFORMATION: 5D11 CDR L1 (Kabat)

<400> SEQUENCE: 21

Arg Ala Ser Gln Ser Val Ser Thr Ser Phe Tyr Ser Tyr Met His
1               5                   10                  15

<210> SEQ ID NO 22
<211> LENGTH: 7
<212> TYPE: PRT
<213> ORGANISM: Artificial
<220> FEATURE:
<223> OTHER INFORMATION: 5D11 CDR L2 (Kabat)

<400> SEQUENCE: 22

Tyr Ala Ser Asn Leu Gln Ser
1               5

<210> SEQ ID NO 23
<211> LENGTH: 9
<212> TYPE: PRT
<213> ORGANISM: Artificial
<220> FEATURE:
<223> OTHER INFORMATION: 5D11 CDR L3 (Kabat)

<400> SEQUENCE: 23

Gln His Ser Trp Glu Ile Pro Trp Thr
1               5

<210> SEQ ID NO 24
<211> LENGTH: 5
<212> TYPE: PRT
<213> ORGANISM: Artificial
<220> FEATURE:
<223> OTHER INFORMATION: 5D11 CDR H1 (Kabat)

<400> SEQUENCE: 24

Asn Tyr Leu Ile Glu
1               5

<210> SEQ ID NO 25
<211> LENGTH: 17
<212> TYPE: PRT
<213> ORGANISM: Artificial
<220> FEATURE:
<223> OTHER INFORMATION: 5D11 CDR H2 (Kabat)

<400> SEQUENCE: 25

Val Ile Asn Pro Gly Ser Gly Gly Thr Asn Tyr Asn Asp Lys Phe Lys
1               5                   10                  15

Gly
```

-continued

```
<210> SEQ ID NO 26
<211> LENGTH: 8
<212> TYPE: PRT
<213> ORGANISM: Artificial
<220> FEATURE:
<223> OTHER INFORMATION: 5D11 CDR H3 (Kabat)

<400> SEQUENCE: 26

Gly Gly Asn Asp Tyr Gly Asp Tyr
1               5

<210> SEQ ID NO 27
<211> LENGTH: 440
<212> TYPE: PRT
<213> ORGANISM: Mouse

<400> SEQUENCE: 27

Gln Val Gln Leu Gln Gln Ser Gly Asp Asp Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Ile Asn Trp Ile Lys Gln Arg Pro Gly Gln Gly Leu Glu Cys Ile
        35                  40                  45

Gly Arg Ile Ala Pro Gly Asn Thr Tyr Tyr Asn Glu Ile Phe Lys Gly
    50                  55                  60

Lys Ala Ile Leu Thr Val Asp Thr Ser Ser Thr Ala Tyr Ile Gln
65                  70                  75                  80

Leu Ser Ser Leu Ser Ser Glu Asp Ser Gly Val Tyr Phe Cys Ala Arg
                85                  90                  95

Arg Gly Tyr Glu Gly Ala Leu Asp Tyr Trp Gly Gln Gly Thr Ser Val
            100                 105                 110

Thr Val Ser Ser Ala Lys Thr Thr Pro Pro Ser Val Tyr Pro Leu Ala
        115                 120                 125

Pro Gly Ser Ala Ala Gln Thr Asn Ser Met Val Thr Leu Gly Cys Leu
    130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Pro Ser Ser Thr Trp Pro
            180                 185                 190

Ser Glu Thr Val Thr Cys Asn Val Ala His Pro Ala Ser Ser Thr Lys
        195                 200                 205

Val Asp Lys Lys Ile Val Pro Arg Asp Cys Gly Cys Lys Pro Cys Ile
    210                 215                 220

Cys Thr Val Pro Glu Val Ser Ser Val Phe Ile Phe Pro Pro Lys Pro
225                 230                 235                 240

Lys Asp Val Leu Thr Ile Thr Leu Thr Pro Lys Val Thr Cys Val Val
                245                 250                 255

Val Asp Ile Ser Lys Asp Asp Pro Glu Val Gln Phe Ser Trp Phe Val
            260                 265                 270

Asp Asp Val Glu Val His Thr Ala Gln Thr Gln Pro Arg Glu Glu Gln
        275                 280                 285

Phe Asn Ser Thr Phe Arg Ser Val Ser Glu Leu Pro Ile Met His Gln
    290                 295                 300

Asp Trp Leu Asn Gly Lys Glu Phe Lys Cys Arg Val Asn Ser Ala Ala
305                 310                 315                 320
```

Phe Pro Ala Pro Ile Glu Lys Thr Ile Ser Lys Thr Lys Gly Arg Pro
            325                 330                 335

Lys Ala Pro Gln Val Tyr Thr Ile Pro Pro Lys Glu Gln Met Ala
        340                 345                 350

Lys Asp Lys Val Ser Leu Thr Cys Met Ile Thr Asp Phe Phe Pro Glu
        355                 360                 365

Asp Ile Thr Val Glu Trp Gln Trp Asn Gly Gln Pro Ala Glu Asn Tyr
370                 375                 380

Lys Asn Thr Gln Pro Ile Met Asp Thr Asp Gly Ser Tyr Phe Val Tyr
385                 390                 395                 400

Ser Lys Leu Asn Val Gln Lys Ser Asn Trp Glu Ala Gly Asn Thr Phe
            405                 410                 415

Thr Cys Ser Val Leu His Glu Gly Leu His Asn His His Thr Glu Lys
            420                 425                 430

Ser Leu Ser His Ser Pro Gly Lys
        435                 440

<210> SEQ ID NO 28
<211> LENGTH: 214
<212> TYPE: PRT
<213> ORGANISM: Mouse

<400> SEQUENCE: 28

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Arg Ile Ser Asn Asn
            20                  25                  30

Leu His Trp Tyr Gln Gln Lys Ser His Glu Ser Pro Arg Leu Leu Ile
        35                  40                  45

Lys Tyr Val Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 29
<211> LENGTH: 439
<212> TYPE: PRT

<213> ORGANISM: mouse

<400> SEQUENCE: 29

```
Gln Val Gln Leu Gln Gln Ser Gly Ala Glu Leu Ala Lys Pro Gly Ala
 1               5                  10                  15

Ser Val Lys Met Ser Cys Lys Ala Ser Gly Tyr Thr Phe Ser Ser Tyr
            20                  25                  30

Trp Met His Trp Val Lys Gln Arg Pro Gly Gln Gly Leu Glu Trp Ile
        35                  40                  45

Gly Tyr Ile Asn Pro Ser Thr Gly Tyr Thr Asp Tyr Asn Gln Lys Phe
    50                  55                  60

Lys Asp Lys Ala Thr Leu Thr Ala Asp Lys Ser Ser Asn Thr Ala Tyr
65                  70                  75                  80

Met Gln Leu Ser Ser Leu Thr Ser Asp Asp Ser Ala Val Tyr Tyr Cys
                85                  90                  95

Ala Arg Ser Arg Ala Ala Arg Tyr Trp Gly Gln Gly Thr Thr Leu Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Glu Thr Val Thr Cys Asn Val Ala His Pro Ala Ser Ser Thr Lys Val
        195                 200                 205

Asp Lys Lys Ile Val Pro Arg Asp Cys Gly Cys Lys Pro Cys Ile Cys
    210                 215                 220

Thr Val Pro Glu Val Ser Ser Val Phe Ile Phe Pro Pro Lys Pro Lys
225                 230                 235                 240

Asp Val Leu Thr Ile Thr Leu Thr Pro Lys Val Thr Cys Val Val Val
                245                 250                 255

Asp Ile Ser Lys Asp Asp Pro Glu Val Gln Phe Ser Trp Phe Val Asp
            260                 265                 270

Asp Val Glu Val His Thr Ala Gln Thr Gln Pro Arg Glu Glu Gln Phe
        275                 280                 285

Asn Ser Thr Phe Arg Ser Val Ser Glu Leu Pro Ile Met His Gln Asp
    290                 295                 300

Trp Leu Asn Gly Lys Glu Phe Lys Cys Arg Val Asn Ser Ala Ala Phe
305                 310                 315                 320

Pro Ala Pro Ile Glu Lys Thr Ile Ser Lys Thr Lys Gly Arg Pro Lys
                325                 330                 335

Ala Pro Gln Val Tyr Thr Ile Pro Pro Pro Lys Glu Gln Met Ala Lys
            340                 345                 350

Asp Lys Val Ser Leu Thr Cys Met Ile Thr Asp Phe Phe Pro Glu Asp
        355                 360                 365

Ile Thr Val Glu Trp Gln Trp Asn Gly Gln Pro Ala Glu Asn Tyr Lys
    370                 375                 380

Asn Thr Gln Pro Ile Met Asp Thr Asp Gly Ser Tyr Phe Val Tyr Ser
385                 390                 395                 400
```

Lys Leu Asn Val Gln Lys Ser Asn Trp Glu Ala Gly Asn Thr Phe Thr
                405                 410                 415

Cys Ser Val Leu His Glu Gly Leu His Asn His His Thr Glu Lys Ser
            420                 425                 430

Leu Ser His Ser Pro Gly Lys
            435

<210> SEQ ID NO 30
<211> LENGTH: 220
<212> TYPE: PRT
<213> ORGANISM: Mouse

<400> SEQUENCE: 30

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Tyr Thr Phe Gly Gly Gly Thr Lys Leu Glu Ile
            100                 105                 110

Lys Arg Ala Asp Ala Ala Pro Thr Val Ser Ile Phe Pro Pro Ser Ser
        115                 120                 125

Glu Gln Leu Thr Ser Gly Gly Ala Ser Val Val Cys Phe Leu Asn Asn
    130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
        195                 200                 205

Ser Pro Ile Val Lys Ser Phe Asn Arg Asn Glu Cys
    210                 215                 220

<210> SEQ ID NO 31
<211> LENGTH: 440
<212> TYPE: PRT
<213> ORGANISM: Mouse

<400> SEQUENCE: 31

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Thr Tyr
            20                  25                  30

Gly Met Ser Trp Val Arg Gln Thr Pro Asp Lys Gly Leu Glu Trp Val
        35                  40                  45

Ala Thr Val Ser Thr Gly Gly Thr Tyr Thr Tyr Tyr Pro Asp Ser Val
    50                  55                  60

```
Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
             85                  90                  95

Ala Arg Gly Gly Tyr Ser Phe Ala Tyr Trp Gly Gln Gly Thr Leu Val
            100                 105                 110

Thr Val Ser Ala Ala Lys Thr Thr Pro Pro Ser Val Tyr Pro Leu Ala
        115                 120                 125

Pro Gly Ser Ala Ala Gln Thr Asn Ser Met Val Thr Leu Gly Cys Leu
    130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Pro Ser Ser Thr Trp Pro
            180                 185                 190

Ser Glu Thr Val Thr Cys Asn Val Ala His Pro Ala Ser Ser Thr Lys
        195                 200                 205

Val Asp Lys Lys Ile Val Pro Arg Asp Cys Gly Cys Lys Pro Cys Ile
210                 215                 220

Cys Thr Val Pro Glu Val Ser Ser Val Phe Ile Phe Pro Pro Lys Pro
225                 230                 235                 240

Lys Asp Val Leu Thr Ile Thr Leu Thr Pro Lys Val Thr Cys Val Val
                245                 250                 255

Val Asp Ile Ser Lys Asp Asp Pro Glu Val Gln Phe Ser Trp Phe Val
            260                 265                 270

Asp Asp Val Glu Val His Thr Ala Gln Thr Gln Pro Arg Glu Glu Gln
        275                 280                 285

Phe Asn Ser Thr Phe Arg Ser Val Ser Glu Leu Pro Ile Met His Gln
    290                 295                 300

Asp Trp Leu Asn Gly Lys Glu Phe Lys Cys Arg Val Asn Ser Ala Ala
305                 310                 315                 320

Phe Pro Ala Pro Ile Glu Lys Thr Ile Ser Lys Thr Lys Gly Arg Pro
                325                 330                 335

Lys Ala Pro Gln Val Tyr Thr Ile Pro Pro Lys Glu Gln Met Ala
            340                 345                 350

Lys Asp Lys Val Ser Leu Thr Cys Met Ile Thr Asp Phe Phe Pro Glu
        355                 360                 365

Asp Ile Thr Val Glu Trp Gln Trp Asn Gly Gln Pro Ala Glu Asn Tyr
370                 375                 380

Lys Asn Thr Gln Pro Ile Met Asp Thr Asp Gly Ser Tyr Phe Val Tyr
385                 390                 395                 400

Ser Lys Leu Asn Val Gln Lys Ser Asn Trp Glu Ala Gly Asn Thr Phe
                405                 410                 415

Thr Cys Ser Val Leu His Glu Gly Leu His Asn His Thr Glu Lys
            420                 425                 430

Ser Leu Ser His Ser Pro Gly Lys
        435                 440

<210> SEQ ID NO 32
<211> LENGTH: 215
<212> TYPE: PRT
<213> ORGANISM: Mouse

<400> SEQUENCE: 32
```

```
Glu Asn Val Leu Thr Gln Ser Pro Ala Ile Met Ser Ala Ser Pro Gly
1               5                   10                  15

Glu Lys Val Thr Met Thr Cys Arg Ala Ser Ser Val Ser Ser Ser
            20                  25                  30

Tyr Leu His Trp Tyr Gln Gln Lys Ser Gly Val Ser Pro Lys Leu Trp
            35                  40                  45

Ile Tyr Ser Thr Ser Asn Leu Ala Ser Gly Val Pro Ala Arg Phe Ser
50                      55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Leu Lys Arg Ala Asp Ala
            100                 105                 110

Ala Pro Thr Val Ser Ile Phe Pro Pro Ser Ser Glu Gln Leu Thr Ser
            115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
        210                 215

<210> SEQ ID NO 33
<211> LENGTH: 441
<212> TYPE: PRT
<213> ORGANISM: Mouse

<400> SEQUENCE: 33

Gln Val His Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Ile Lys Gln Arg Pro Gly Gln Gly Leu Glu Trp Ile
            35                  40                  45

Gly Val Ile Asn Pro Gly Ser Gly Gly Thr Asn Tyr Asn Asp Lys Phe
50                  55                  60

Lys Gly Lys Ala Ile Leu Thr Ala Asp Lys Ser Ser Thr Thr Ala Tyr
65                  70                  75                  80

Met Gln Leu Ser Ser Leu Thr Ser Asp Asp Ser Ala Val Tyr Phe Cys
                85                  90                  95

Ala Arg Gly Gly Asn Asp Tyr Gly Asp Tyr Trp Gly Gln Gly Thr Ser
            100                 105                 110

Val Thr Val Ser Ser Ala Lys Thr Thr Pro Pro Ser Val Tyr Pro Leu
            115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
```

```
                145                 150                 155                 160
        Gly Ser Leu Ser Ser Gly Val His Thr Phe Pro Ala Val Leu Gln Ser
                        165                 170                 175

Asp Leu Tyr Thr Leu Ser Ser Val Thr Val Pro Ser Ser Thr Trp
                    180                 185                 190

Pro Ser Glu Thr Val Thr Cys Asn Val Ala His Pro Ala Ser Ser Thr
                    195                 200                 205

Lys Val Asp Lys Lys Ile Val Pro Arg Asp Cys Gly Cys Lys Pro Cys
                    210                 215                 220

Ile Cys Thr Val Pro Glu Val Ser Ser Val Phe Ile Phe Pro Pro Lys
        225                 230                 235                 240

Pro Lys Asp Val Leu Thr Ile Thr Leu Thr Pro Lys Val Thr Cys Val
                            245                 250                 255

Val Val Asp Ile Ser Lys Asp Asp Pro Glu Val Gln Phe Ser Trp Phe
                        260                 265                 270

Val Asp Asp Val Glu Val His Thr Ala Gln Thr Gln Pro Arg Glu Glu
                        275                 280                 285

Gln Phe Asn Ser Thr Phe Arg Ser Val Ser Glu Leu Pro Ile Met His
                290                 295                 300

Gln Asp Trp Leu Asn Gly Lys Glu Phe Lys Cys Arg Val Asn Ser Ala
        305                 310                 315                 320

Ala Phe Pro Ala Pro Ile Glu Lys Thr Ile Ser Lys Thr Lys Gly Arg
                            325                 330                 335

Pro Lys Ala Pro Gln Val Tyr Thr Ile Pro Pro Lys Glu Gln Met
                        340                 345                 350

Ala Lys Asp Lys Val Ser Leu Thr Cys Met Ile Thr Asp Phe Phe Pro
                    355                 360                 365

Glu Asp Ile Thr Val Glu Trp Gln Trp Asn Gly Gln Pro Ala Glu Asn
                370                 375                 380

Tyr Lys Asn Thr Gln Pro Ile Met Asp Thr Asp Gly Ser Tyr Phe Val
        385                 390                 395                 400

Tyr Ser Lys Leu Asn Val Gln Lys Ser Asn Trp Glu Ala Gly Asn Thr
                            405                 410                 415

Phe Thr Cys Ser Val Leu His Glu Gly Leu His Asn His His Thr Glu
                        420                 425                 430

Lys Ser Leu Ser His Ser Pro Gly Lys
                        435                 440

<210> SEQ ID NO 34
<211> LENGTH: 218
<212> TYPE: PRT
<213> ORGANISM: Mouse

<400> SEQUENCE: 34

Asp Ile Val Leu Thr Gln Ser Pro Ala Ser Leu Ala Val Ser Leu Gly
        1               5                   10                  15

Gln Arg Ala Thr Ile Ser Cys Arg Ala Ser Gln Ser Val Ser Thr Ser
                        20                  25                  30

Phe Tyr Ser Tyr Met His Trp Tyr Gln Gln Lys Pro Gly Gln Pro Pro
                    35                  40                  45

Lys Val Phe Ile Lys Tyr Ala Ser Asn Leu Gln Ser Gly Val Pro Ala
                50                  55                  60

Arg Phe Ser Gly Ser Gly Ser Gly Thr Asp Phe Thr Leu Asn Ile His
        65                  70                  75                  80
```

```
Pro Val Glu Glu Asp Thr Ala Thr Tyr Tyr Cys Gln His Ser Trp
            85                  90                  95

Glu Ile Pro Trp Thr Phe Gly Gly Thr Lys Leu Glu Ile Lys Arg
            100                 105                 110

Ala Asp Ala Ala Pro Thr Val Ser Ile Phe Pro Pro Ser Glu Gln
            115                 120                 125

Leu Thr Ser Gly Gly Ala Ser Val Val Cys Phe Leu Asn Asn Phe Tyr
            130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                    165                 170                 175

Tyr Ser Met Ser Ser Thr Leu Thr Leu Thr Lys Asp Glu Tyr Glu Arg
                    180                 185                 190

His Asn Ser Tyr Thr Cys Glu Ala Thr His Lys Thr Ser Thr Ser Pro
                    195                 200                 205

Ile Val Lys Ser Phe Asn Arg Asn Glu Cys
210                 215

<210> SEQ ID NO 35
<211> LENGTH: 165
<212> TYPE: PRT
<213> ORGANISM: Artificial
<220> FEATURE:
<223> OTHER INFORMATION: Human TrkB D1-D3 domain deletion variant C32-
      L196

<400> SEQUENCE: 35

Cys Pro Thr Ser Cys Lys Cys Ser Ala Ser Arg Ile Trp Cys Ser Asp
1               5                   10                  15

Pro Ser Pro Gly Ile Val Ala Phe Pro Arg Leu Glu Pro Asn Ser Val
            20                  25                  30

Asp Pro Glu Asn Ile Thr Glu Ile Phe Ile Ala Asn Gln Lys Arg Leu
            35                  40                  45

Glu Ile Ile Asn Glu Asp Asp Val Glu Ala Tyr Val Gly Leu Arg Asn
50                  55                  60

Leu Thr Ile Val Asp Ser Gly Leu Lys Phe Val Ala His Lys Ala Phe
65                  70                  75                  80

Leu Lys Asn Ser Asn Leu Gln His Ile Asn Phe Thr Arg Asn Lys Leu
                85                  90                  95

Thr Ser Leu Ser Arg Lys His Phe Arg His Leu Asp Leu Ser Glu Leu
            100                 105                 110

Ile Leu Val Gly Asn Pro Phe Thr Cys Ser Cys Asp Ile Met Trp Ile
            115                 120                 125

Lys Thr Leu Gln Glu Ala Lys Ser Ser Pro Asp Thr Gln Asp Leu Tyr
            130                 135                 140

Cys Leu Asn Glu Ser Ser Lys Asn Ile Pro Leu Ala Asn Leu Gln Ile
145                 150                 155                 160

Pro Asn Cys Gly Leu
                165

<210> SEQ ID NO 36
<211> LENGTH: 234
<212> TYPE: PRT
<213> ORGANISM: Artificial
<220> FEATURE:
<223> OTHER INFORMATION: Human TrkB D4-D5-JM domain deletion variant
      P197-H430
```

<400> SEQUENCE: 36

Pro Ser Ala Asn Leu Ala Ala Pro Asn Leu Thr Val Glu Glu Gly Lys
1               5                   10                  15

Ser Ile Thr Leu Ser Cys Ser Val Ala Gly Asp Pro Val Pro Asn Met
            20                  25                  30

Tyr Trp Asp Val Gly Asn Leu Val Ser Lys His Met Asn Glu Thr Ser
            35                  40                  45

His Thr Gln Gly Ser Leu Arg Ile Thr Asn Ile Ser Ser Asp Asp Ser
    50                  55                  60

Gly Lys Gln Ile Ser Cys Val Ala Glu Asn Leu Val Gly Glu Asp Gln
65                  70                  75                  80

Asp Ser Val Asn Leu Thr Val His Phe Ala Pro Thr Ile Thr Phe Leu
                85                  90                  95

Glu Ser Pro Thr Ser Asp His His Trp Cys Ile Pro Phe Thr Val Lys
            100                 105                 110

Gly Asn Pro Lys Pro Ala Leu Gln Trp Phe Tyr Asn Gly Ala Ile Leu
        115                 120                 125

Asn Glu Ser Lys Tyr Ile Cys Thr Lys Ile His Val Thr Asn His Thr
130                 135                 140

Glu Tyr His Gly Cys Leu Gln Leu Asp Asn Pro Thr His Met Asn Asn
145                 150                 155                 160

Gly Asp Tyr Thr Leu Ile Ala Lys Asn Glu Tyr Gly Lys Asp Glu Lys
                165                 170                 175

Gln Ile Ser Ala His Phe Met Gly Trp Pro Gly Ile Asp Asp Gly Ala
            180                 185                 190

Asn Pro Asn Tyr Pro Asp Val Ile Tyr Glu Asp Tyr Gly Thr Ala Ala
        195                 200                 205

Asn Asp Ile Gly Asp Thr Thr Asn Arg Ser Asn Glu Ile Pro Ser Thr
210                 215                 220

Asp Val Thr Asp Lys Thr Gly Arg Glu His
225                 230

<210> SEQ ID NO 37
<211> LENGTH: 147
<212> TYPE: PRT
<213> ORGANISM: Artificial
<220> FEATURE:
<223> OTHER INFORMATION: Human TrkB D5 domain deletion variant H284-H430

<400> SEQUENCE: 37

His Phe Ala Pro Thr Ile Thr Phe Leu Glu Ser Pro Thr Ser Asp His
1               5                   10                  15

His Trp Cys Ile Pro Phe Thr Val Lys Gly Asn Pro Lys Pro Ala Leu
            20                  25                  30

Gln Trp Phe Tyr Asn Gly Ala Ile Leu Asn Glu Ser Lys Tyr Ile Cys
            35                  40                  45

Thr Lys Ile His Val Thr Asn His Thr Glu Tyr His Gly Cys Leu Gln
    50                  55                  60

Leu Asp Asn Pro Thr His Met Asn Asn Gly Asp Tyr Thr Leu Ile Ala
65                  70                  75                  80

Lys Asn Glu Tyr Gly Lys Asp Glu Lys Gln Ile Ser Ala His Phe Met
                85                  90                  95

Gly Trp Pro Gly Ile Asp Asp Gly Ala Asn Pro Asn Tyr Pro Asp Val
            100                 105                 110

```
Ile Tyr Glu Asp Tyr Gly Thr Ala Ala Asn Asp Ile Gly Asp Thr Thr
            115                 120                 125

Asn Arg Ser Asn Glu Ile Pro Ser Thr Asp Val Thr Asp Lys Thr Gly
130                 135                 140

Arg Glu His
145

<210> SEQ ID NO 38
<211> LENGTH: 221
<212> TYPE: PRT
<213> ORGANISM: Artificial
<220> FEATURE:
<223> OTHER INFORMATION: 1G11 chimeric Fab1 [variable region (VH) from
      1G11 fused with constant region (CH1) from human IgG1]

<400> SEQUENCE: 38

Gln Val Gln Leu Gln Gln Ser Gly Asp Asp Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Ile Asn Trp Ile Lys Gln Arg Pro Gly Gln Gly Leu Glu Cys Ile
        35                  40                  45

Gly Arg Ile Ala Pro Gly Asn Thr Tyr Tyr Asn Glu Ile Phe Lys Gly
    50                  55                  60

Lys Ala Ile Leu Thr Val Asp Thr Ser Ser Thr Ala Tyr Ile Gln
65                  70                  75                  80

Leu Ser Ser Leu Ser Ser Glu Asp Ser Gly Val Tyr Phe Cys Ala Arg
                85                  90                  95

Arg Gly Tyr Glu Gly Ala Leu Asp Tyr Trp Gly Gln Gly Thr Ser Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys
    210                 215                 220

<210> SEQ ID NO 39
<211> LENGTH: 214
<212> TYPE: PRT
<213> ORGANISM: Artificial
<220> FEATURE:
<223> OTHER INFORMATION: 1G11 chimeric Fab1 [variable region (VL) from
      1G11 fused with constant region (CL1) from human IgG1]

<400> SEQUENCE: 39

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Arg Ile Ser Asn Asn
            20                  25                  30
```

```
Leu His Trp Tyr Gln Gln Lys Ser His Glu Ser Pro Arg Leu Leu Ile
         35                  40                  45

Lys Tyr Val Ser Gln Ser Ile Ser Gly Ile Pro Ser Arg Phe Ser Gly
 50                  55                  60

Ser Gly Ser Gly Thr Asp Phe Thr Leu Ser Ile Asn Ser Val Glu Thr
 65                  70                  75                  80

Glu Asp Phe Gly Met Tyr Phe Cys Gln Gln Ser Asn Ser Trp Pro Leu
                 85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 40
<211> LENGTH: 116
<212> TYPE: PRT
<213> ORGANISM: Artificial
<220> FEATURE:
<223> OTHER INFORMATION: Humanised 1G11 VH

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Tyr Ile Asn Trp Val Arg Gln Ala Pro Gly Gln Gly Leu Glu Ser Met
        35                  40                  45

Gly Arg Ile Ala Pro Gly Asn Thr Tyr Tyr Asn Glu Ile Phe Lys Gly
    50                  55                  60

Arg Val Thr Ile Thr Ala Asp Lys Ser Thr Ser Thr Ala Tyr Met Glu
65                  70                  75                  80

Leu Ser Ser Leu Arg Ser Glu Asp Thr Ala Val Tyr Tyr Cys Ala Arg
                85                  90                  95

Arg Gly Tyr Glu Gly Ala Leu Asp Tyr Trp Gly Gln Gly Thr Leu Val
            100                 105                 110

Thr Val Ser Ser
        115

<210> SEQ ID NO 41
<211> LENGTH: 107
<212> TYPE: PRT
<213> ORGANISM: Artificial
<220> FEATURE:
<223> OTHER INFORMATION: Humanised 1G11 VL

<400> SEQUENCE: 41
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Arg Ile Ser Asn Asn
            20                  25                  30

Leu His Trp Tyr Gln Gln Lys Pro Gly Gln Ala Pro Arg Leu Leu Ile
        35                  40                  45

Lys Tyr Val Ser Gln Ser Ile Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Ser Trp Pro Leu
                85                  90                  95

Thr Phe Gly Gln Gly Thr Lys Leu Glu Ile Lys
            100                 105

<210> SEQ ID NO 42
<211> LENGTH: 446
<212> TYPE: PRT
<213> ORGANISM: Artificial
<220> FEATURE:
<223> OTHER INFORMATION: Humanised 1G11 Heavy chain

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Tyr Ile Asn Trp Val Arg Gln Ala Pro Gly Gln Gly Leu Glu Ser Met
        35                  40                  45

Gly Arg Ile Ala Pro Gly Asn Thr Tyr Tyr Asn Glu Ile Phe Lys Gly
50                  55                  60

Arg Val Thr Ile Thr Ala Asp Lys Ser Thr Ser Thr Ala Tyr Met Glu
65                  70                  75                  80

Leu Ser Ser Leu Arg Ser Glu Asp Thr Ala Val Tyr Tyr Cys Ala Arg
                85                  90                  95

Arg Gly Tyr Glu Gly Ala Leu Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Val Glu Pro Lys Ser Cys Asp Lys Thr His Thr
210                 215                 220

Cys Pro Pro Cys Pro Ala Pro Glu Leu Ala Gly Ala Pro Ser Val Phe
225                 230                 235                 240

Leu Phe Pro Pro Lys Pro Lys Asp Thr Leu Met Ile Ser Arg Thr Pro
                245                 250                 255

```
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
            275                 280                 285
Lys Pro Arg Glu Glu Gln Tyr Asn Ser Thr Tyr Arg Val Val Ser Val
        290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
        370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
            435                 440                 445

<210> SEQ ID NO 43
<211> LENGTH: 214
<212> TYPE: PRT
<213> ORGANISM: Artificial
<220> FEATURE:
<223> OTHER INFORMATION: Humanised 1G11 Light chain

<400> SEQUENCE: 43

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Arg Ile Ser Asn Asn
            20                  25                  30
Leu His Trp Tyr Gln Gln Lys Pro Gly Gln Ala Pro Arg Leu Leu Ile
        35                  40                  45
Lys Tyr Val Ser Gln Ser Ile Ser Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Ser Asn Ser Trp Pro Leu
                85                  90                  95
Thr Phe Gly Gln Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 44
<211> LENGTH: 1338
<212> TYPE: DNA
<213> ORGANISM: Artificial
<220> FEATURE:
<223> OTHER INFORMATION: DNA encoding humanised 1G11 Heavy chain

<400> SEQUENCE: 44
caggtgcagc tcgtgcagag cggcgccgaa gtcaaaaagc ccggcagcag cgtgaaggtg      60
agctgcaagg ccagcggcta caccttcacc tcctactaca tcaactgggt gaggcaggct     120
cccggacagg gcctggagag catgggcagg atcgccccg gcaacaccta ctacaacgag     180
atcttcaagg gcagggtgac catcactgcc gacaagagca ccagcaccgc ctacatggaa     240
ctgtctagcc tgaggagcga ggacaccgcc gtgtactact gcgccagaag gggctacgag     300
ggcgccctgg actattgggg ccagggcaca ctagtgaccg tgtccagcgc cagcaccaag     360
ggccccagcg tgttcccct ggccccagc agcaagagca ccagcggcgg cacagccgcc     420
ctgggctgcc tggtgaagga ctacttcccc gaaccggtga ccgtgtcctg aacagcgga     480 gccctgacca cggcgtgca caccttcccc gccgtgctgc agagcagcgg cctgtacagc     540
ctgagcagcg tggtgaccgt gcccagcagc agcctgggca cccagaccta catctgtaac     600
gtgaaccaca agcccagcaa caccaaggtg gacaagaagg tggagcccaa gagctgtgac     660
aagacccaca cctgccccc ctgccctgcc ccgagctgg ccggagcccc cagcgtgttc     720
ctgttccccc caagcctaa ggacaccctg atgatcagca aaccccga ggtgacctgt     780 gtggtggtgg atgtgagcca cgaggaccct gaggtgaagt tcaactggta cgtggacggc     840
gtggaggtgc acaatgccaa gaccaagccc agggaggagc agtacaacag cacctaccgg     900
gtggtgtccg tgctgaccgt gctgcaccag gattggctga acggcaagga gtacaagtgt     960
aaggtgtcca caaggccct gcctgcccct atcgagaaaa ccatcagcaa ggccaagggc    1020
cagcccagag agccccaggt gtacaccctg ccccctagca gagatgagct gaccaagaac    1080
caggtgtccc tgacctgcct ggtgaagggc ttctaccca cgacatcgc cgtggagtgg    1140 gagagcaacg gccagcccga gaacaactac aagaccaccc cccctgtgct ggacagcgat    1200
ggcagcttct tcctgtacag caagctgacc gtggacaaga gcagatggca gcagggcaac    1260
gtgttcagct gctccgtgat gcacgaggcc ctgcacaatc actacaccca gaagagcctg    1320
agcctgtccc ctggcaag                                                  1338

<210> SEQ ID NO 45
<211> LENGTH: 642
<212> TYPE: DNA
<213> ORGANISM: Artificial
<220> FEATURE:
<223> OTHER INFORMATION: DNA encoding humanised 1G11 Light chain

<400> SEQUENCE: 45
gagatcgtgc tgacccagag ccccgccact ctgagcctga gccaggcga agggcaacc      60 ctgagctgca gggcctccca gaggatcagc aacaacctgc actggtacca gcagaagccc     120
```

```
ggccaggccc ccaggctgct gatcaaatac gtgagccaga gcatcagcgg catccccgcc      180
aggtttagcg gaagcggcag cggcaccgac ttcacgctga ccattagcag cctggagccc      240
gaggacttcg ccgtctacta ctgccagcag tctaacagct ggcccctgac cttcggccag      300
ggcaccaagc tcgagatcaa gcgtacggtg gccgccccca gcgtgttcat cttccccccc      360
agcgatgagc agctgaagag cggcaccgcc agcgtggtgt gtctgctgaa caacttctac      420
cccgcggagg ccaaggtgca gtggaaggtg gacaatgccc tgcagagcgg caacagccag      480
gagagcgtga ccgagcagga cagcaaggac tccacctaca gcctgagcag caccctgacc      540
ctgagcaagg ccgactacga gaagcacaag gtgtacgcct gtgaggtgac ccaccagggc      600
ctgtccagcc ccgtgaccaa gagcttcaac cggggcgagt gc                        642
```

<210> SEQ ID NO 46
<211> LENGTH: 115
<212> TYPE: PRT
<213> ORGANISM: Artificial
<220> FEATURE:
<223> OTHER INFORMATION: Humanised 3A3 VH

<400> SEQUENCE: 46

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Met
        35                  40                  45

Gly Tyr Ile Asn Pro Ser Thr Gly Tyr Thr Asp Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Ala Ala Arg Tyr Trp Gly Gln Gly Thr Leu Val Thr
            100                 105                 110

Val Ser Ser
        115
```

<210> SEQ ID NO 47
<211> LENGTH: 113
<212> TYPE: PRT
<213> ORGANISM: Artificial
<220> FEATURE:
<223> OTHER INFORMATION: Humanised 3A3 VL

<400> SEQUENCE: 47

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
```

```
                85                  90                  95
Tyr Tyr Ser Tyr Pro Tyr Thr Phe Gly Gln Gly Thr Lys Leu Glu Ile
            100                 105                 110
Lys

<210> SEQ ID NO 48
<211> LENGTH: 445
<212> TYPE: PRT
<213> ORGANISM: Artificial
<220> FEATURE:
<223> OTHER INFORMATION: Humanised 3A3 HC

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Met
        35                  40                  45

Gly Tyr Ile Asn Pro Ser Thr Gly Tyr Thr Asp Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Ala Ala Arg Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335
```

```
Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 49
<211> LENGTH: 220
<212> TYPE: PRT
<213> ORGANISM: Artificial
<220> FEATURE:
<223> OTHER INFORMATION: Humanised 3A3 LC

<400> SEQUENCE: 49

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 50
<211> LENGTH: 1335
<212> TYPE: DNA
<213> ORGANISM: Artificial
```

<220> FEATURE:
<223> OTHER INFORMATION: DNA encoding humanised 3A3 HC

<400> SEQUENCE: 50

```
caggtccagc tggtgcagag cggcgccgag gtgaagaaac ccggcagctc cgtgaaggtg      60
agctgcaagg ccagcggcta caccttctcc agctactgga tgcactgggt gaggcaggcc     120
cccggacagg gcctggagtg gatgggctac atcaacccca gcaccggcta caccgactac     180
aaccagaagt tcaaggacag ggtgaccatc accgccgaca gagccaccag caccgcctac     240
atggaactga gcagcctgag gagcgaggac accgccgtgt actattgcgc caggagcagg     300
gctgccaggt actggggcca gggcacacta gtgaccgtgt ccagcgccag caccaagggc     360
ccagcgtgt tccccctggc cccagcagc aagagcacca gcggcggcac agccgccctg       420
ggctgcctgg tgaaggacta cttccccgaa ccggtgaccg tgtcctggaa cagcggagcc     480
ctgaccagcg gcgtgcacac cttccccgcc gtgctgcaga gcagcggcct gtacagcctg     540
agcagcgtgg tgaccgtgcc agcagcagc ctgggcaccc agacctacat ctgtaacgtg      600
aaccacaagc ccagcaacac caaggtggac aagaaggtgg agcccaagag ctgtgacaag     660
acccacacct gcccccctg ccctgcccc gagctggccg gagcccccag cgtgttcctg       720
ttcccccca agcctaagga caccctgatg atcagcagaa cccccgaggt gacctgtgtg      780
gtggtggatg tgagccacga ggaccctgag gtgaagttca actggtacgt ggacggcgtg     840
gaggtgcaca atgccaagac caagcccagg gaggagcagt acaacagcac ctaccgggtg     900
gtgtccgtgc tgaccgtgct gcaccaggat tggctgaacg gcaaggagta caagtgtaag     960
gtgtccaaca aggccctgcc tgcccctatc gagaaaacca tcagcaaggc caagggccag    1020
cccagagagc cccaggtgta caccctgccc cctagcagag atgagctgac caagaaccag    1080
gtgtccctga cctgcctggt gaagggcttc taccccagcg acatcgccgt ggagtgggag    1140
agcaacggcc agcccgagaa caactacaag accaccccc ctgtgctgga cagcgatggc    1200
agcttcttcc tgtacagcaa gctgaccgtg gacaagagca gatggcagca gggcaacgtg    1260
ttcagctgct ccgtgatgca cgaggccctg cacaatcact acacccagaa gagcctgagc    1320
ctgtcccctg gcaag                                                    1335
```

<210> SEQ ID NO 51
<211> LENGTH: 660
<212> TYPE: DNA
<213> ORGANISM: Artificial
<220> FEATURE:
<223> OTHER INFORMATION: DNA encoding humanised 3A3 LC

<400> SEQUENCE: 51

```
gacatcgtga tgacccagag ccccgactct ctggccgtga gcctgggcga aagggccacc      60
atcaactgca gagcagcca gagcctcctg tacagcggca accagaagaa ctacctggcc     120
tggtatcagc agaagcccgg ccagccccc aaactgctga tctactgggc tagcacaagg      180
gagagcggcg tgcctgatag gttcagcgga agcggcagcg gcaccgactt cacccctgacc   240
attagcagcc tgcaggccga ggacgtggcc gtctactact gccagcagta ctactcctac     300
ccctacacct tcggccaggg caccaagctg gagatcaagc gtacggtggc cgcccccagc     360
gtgttcatct tcccccccag cgatgagcag ctgaagagcg gcaccgccag cgtggtgtgt     420
ctgctgaaca acttctaccc ccggagcc aaggtgcagt ggaaggtgga caatgccctg       480
cagagcggca acagccagga gagcgtgacc gagcaggaca gcaaggactc cacctacagc     540
```

```
ctgagcagca ccctgaccct gagcaaggcc gactacgaga agcacaaggt gtacgcctgt    600
gaggtgaccc accagggcct gtccagcccc gtgaccaaga gcttcaaccg gggcgagtgc    660
```

```
<210> SEQ ID NO 52
<211> LENGTH: 117
<212> TYPE: PRT
<213> ORGANISM: Artificial
<220> FEATURE:
<223> OTHER INFORMATION: Humanised 5D11 VH

<400> SEQUENCE: 52
```

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Asp Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Asp Tyr Gly Asp Tyr Trp Gly Gln Gly Thr Leu
            100                 105                 110

Val Thr Val Ser Ser
        115

```
<210> SEQ ID NO 53
<211> LENGTH: 111
<212> TYPE: PRT
<213> ORGANISM: Artificial
<220> FEATURE:
<223> OTHER INFORMATION: Humanised 5D11 VL

<400> SEQUENCE: 53
```

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Thr Ser
            20                  25                  30

Phe Tyr Ser Tyr Met His Trp Tyr Gln Gln Lys Pro Gly Gln Pro Pro
        35                  40                  45

Lys Val Leu Ile Lys Tyr Ala Ser Asn Leu Gln Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Trp Thr Phe Gly Gly Gly Thr Lys Leu Glu Ile Lys
            100                 105                 110

```
<210> SEQ ID NO 54
<211> LENGTH: 447
<212> TYPE: PRT
<213> ORGANISM: Artificial
<220> FEATURE:
<223> OTHER INFORMATION: Humanised 5D11 Heavy chain

<400> SEQUENCE: 54
```

```
Gln Val Gln Leu Val Gln Ser Gly Ala Glu Val Lys Lys Pro Gly Ser
  1               5                  10                  15

Ser Val Lys Val Ser Cys Lys Ala Ser Gly Tyr Ala Phe Thr Asn Tyr
             20                  25                  30

Leu Ile Glu Trp Val Arg Gln Ala Pro Gly Gln Gly Leu Glu Trp Met
             35                  40                  45

Gly Val Ile Asn Pro Gly Ser Gly Gly Thr Asn Tyr Asn Asp Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Gly Gly Asn Asp Tyr Gly Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
            210                 215                 220

Thr Cys Pro Pro Cys Pro Ala Pro Glu Leu Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
```

His Asn His Tyr Thr Gln Lys Ser Leu Ser Leu Ser Pro Gly Lys
            435                 440                 445

<210> SEQ ID NO 55
<211> LENGTH: 218
<212> TYPE: PRT
<213> ORGANISM: Artificial
<220> FEATURE:
<223> OTHER INFORMATION: Humanised 5D11 Light Chain

<400> SEQUENCE: 55

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Thr Ser
            20                  25                  30

Phe Tyr Ser Tyr Met His Trp Tyr Gln Gln Lys Pro Gly Gln Pro Pro
        35                  40                  45

Lys Val Leu Ile Lys Tyr Ala Ser Asn Leu Gln Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 56
<211> LENGTH: 1341
<212> TYPE: DNA
<213> ORGANISM: Artificial
<220> FEATURE:
<223> OTHER INFORMATION: DNA encoding humanised 5D11 Heavy chain

<400> SEQUENCE: 56
caggtgcagc tggtgcagag cggcgccgaa gtcaagaagc ccggcagctc cgtgaaggtg     60
agctgcaaag ccagcggcta cgccttcacc aactacctga tcgagtgggt gaggcaggct    120
cccggccagg gcctggagtg gatgggagtg atcaatcccg gcagcggcgg caccaactac    180
aacgacaagt tcaagggcag ggtgaccatc accgccgaca gagcaccag caccgcctac    240 atggaactga gcagcctcag gagcgaggac actgccgtgt actattgcgc caggggcggg    300
aacgattacg cgactactg gggccagggc acactagtga ccgtgtccag cgccagcacc    360

```
aagggcccca gcgtgttccc cctggccccc agcagcaaga gcaccagcgg cggcacagcc    420
gccctgggct gcctggtgaa ggactacttc cccgaaccgg tgaccgtgtc ctggaacagc    480
ggagccctga ccagcggcgt gcacaccttc ccgccgtgc tgcagagcag cggcctgtac     540
agcctgagca gcgtggtgac cgtgcccagc agcagcctgg gcacccagac ctacatctgt    600
aacgtgaacc acaagcccag caacaccaag gtggacaaga aggtggagcc caagagctgt    660
gacaagaccc acacctgccc ccctgcccct gccccgagc tggccggagc ccccagcgtg     720
ttcctgttcc cccccaagcc taaggacacc ctgatgatca gcagaacccc cgaggtgacc    780
tgtgtggtgg tggatgtgag ccacgaggac cctgaggtga agttcaactg gtacgtggac    840
ggcgtggagg tgcacaatgc caagaccaag cccggggagg agcagtacaa cagcacctac    900
cgggtggtgt ccgtgctgac cgtgctgcac caggattggc tgaacggcaa ggagtacaag    960
tgtaaggtgt ccaacaaggc cctgcctgcc cctatcgaga aaaccatcag caaggccaag   1020
ggccagccca gagagcccca ggtgtacacc ctgcccccta gcagagatga gctgaccaag   1080
aaccaggtgt ccctgacctg cctggtgaag ggcttctacc ccagcgacat cgccgtggag   1140
tgggagagca cggccagcc cgagaacaac tacaagacca ccccccctgt gctggacagc    1200
gatggcagct tcttcctgta cagcaagctg accgtggaca gagcagatg gcagcagggc    1260 aacgtgttca gctgctccgt gatgcacgag gccctgcaca atcactacac ccagaagagc   1320
ctgagcctgt ccctggcaa g                                               1341

<210> SEQ ID NO 57
<211> LENGTH: 654
<212> TYPE: DNA
<213> ORGANISM: Artificial
<220> FEATURE:
<223> OTHER INFORMATION: DNA encoding humanised 5D11 Light chain

<400> SEQUENCE: 57
gacatcgtga tgacccagag ccccgatagc ctggccgtga gcctgggcga gagggccacc     60
attaactgca gggccagcca gagcgtgagc accagcttct actcctacat gcactggtac    120
cagcagaaac ccggccagcc ccccaaggtg ctgatcaaat acgccagcaa cctccagagc    180
ggcgtgcccg acaggttcag cggctcaggc tccggcaccg acttcacact gaccatcagc    240
agcctgcagg cagaggacgt ggccgtctac tactgccagc acagctggga gatcccctgg    300
accttcggcc agggaaccaa gctggagatc aagcgtacgg tggccgcccc cagcgtgttc    360
atcttccccc ccagcgatga gcagctgaag agcggcaccg ccagcgtggt gtgtctgctg    420
aacaacttct accccgggga ggccaaggtg cagtggaagg tggacaatgc cctgcagagc    480
ggcaacagcc aggagagcgt gaccgagcag gacagcaagg actccaccta cagcctgagc    540
agcaccctga ccctgagcaa ggccgactac gagaagcaca aggtgtacgc ctgtgaggtg    600
acccaccagg gcctgtccag ccccgtgacc aagagcttca ccggggcga gtgc           654

<210> SEQ ID NO 58
<211> LENGTH: 7
<212> TYPE: PRT
<213> ORGANISM: Artificial
<220> FEATURE:
<223> OTHER INFORMATION: 1G11 and humanised 1G11 CDRH1 (Chothia)

<400> SEQUENCE: 58

Gly Tyr Thr Phe Thr Ser Tyr
1               5
```

<210> SEQ ID NO 59
<211> LENGTH: 4
<212> TYPE: PRT
<213> ORGANISM: Artificial
<220> FEATURE:
<223> OTHER INFORMATION: 1G11 and humanised 1G11 CDRH2 (Chothia)

<400> SEQUENCE: 59

Ala Pro Gly Asn
1

<210> SEQ ID NO 60
<211> LENGTH: 10
<212> TYPE: PRT
<213> ORGANISM: Artificial
<220> FEATURE:
<223> OTHER INFORMATION: 1G11 and humanised 1G11 CDRH1 (AbM)

<400> SEQUENCE: 60

Gly Tyr Thr Phe Thr Ser Tyr Tyr Ile Asn
1               5                   10

<210> SEQ ID NO 61
<211> LENGTH: 8
<212> TYPE: PRT
<213> ORGANISM: Artificial
<220> FEATURE:
<223> OTHER INFORMATION: 1G11 and humanised 1G11 CDRH2 (AbM)

<400> SEQUENCE: 61

Arg Ile Ala Pro Gly Asn Thr Tyr
1               5

<210> SEQ ID NO 62
<211> LENGTH: 6
<212> TYPE: PRT
<213> ORGANISM: Artificial
<220> FEATURE:
<223> OTHER INFORMATION: 1G11 and humanised 1G11 CDRH1 (Contact)

<400> SEQUENCE: 62

Thr Ser Tyr Tyr Ile Asn
1               5

<210> SEQ ID NO 63
<211> LENGTH: 11
<212> TYPE: PRT
<213> ORGANISM: Artificial
<220> FEATURE:
<223> OTHER INFORMATION: 1G11 CDRH2 (Contact)

<400> SEQUENCE: 63

Cys Ile Gly Arg Ile Ala Pro Gly Asn Thr Tyr
1               5                   10

<210> SEQ ID NO 64
<211> LENGTH: 11
<212> TYPE: PRT
<213> ORGANISM: Artificial
<220> FEATURE:
<223> OTHER INFORMATION: humanised 1G11 CDRH2 (Contact)

<400> SEQUENCE: 64

Ser Met Gly Arg Ile Ala Pro Gly Asn Thr Tyr
1               5                   10

```
<210> SEQ ID NO 65
<211> LENGTH: 10
<212> TYPE: PRT
<213> ORGANISM: Artificial
<220> FEATURE:
<223> OTHER INFORMATION: 1G11 and humanised 1G11 CDRH3

<400> SEQUENCE: 65

Ala Arg Arg Gly Tyr Glu Gly Ala Leu Asp
1               5                   10

<210> SEQ ID NO 66
<211> LENGTH: 7
<212> TYPE: PRT
<213> ORGANISM: Artificial
<220> FEATURE:
<223> OTHER INFORMATION: 1G11 and humanised 1G11 CDRL1 (Contact)

<400> SEQUENCE: 66

Ser Asn Asn Leu His Trp Tyr
1               5

<210> SEQ ID NO 67
<211> LENGTH: 10
<212> TYPE: PRT
<213> ORGANISM: Artificial
<220> FEATURE:
<223> OTHER INFORMATION: 1G11 and humanised 1G11 CDRL2 (Contact)

<400> SEQUENCE: 67

Leu Leu Ile Lys Tyr Val Ser Gln Ser Ile
1               5                   10

<210> SEQ ID NO 68
<211> LENGTH: 8
<212> TYPE: PRT
<213> ORGANISM: Artificial
<220> FEATURE:
<223> OTHER INFORMATION: 1G11 and humanised 1G11 CDRL3 (Contact)

<400> SEQUENCE: 68

Gln Gln Ser Asn Ser Trp Pro Leu
1               5

<210> SEQ ID NO 69
<211> LENGTH: 20
<212> TYPE: PRT
<213> ORGANISM: Artificial
<220> FEATURE:
<223> OTHER INFORMATION: Peptide derived from human TrkB

<400> SEQUENCE: 69

Asp Gly Ala Asn Pro Asn Tyr Pro Asp Val Ile Tyr Glu Asp Tyr Gly
1               5                   10                  15

Thr Ala Ala Asn
            20

<210> SEQ ID NO 70
<211> LENGTH: 14
<212> TYPE: PRT
<213> ORGANISM: Artificial
<220> FEATURE:
<223> OTHER INFORMATION: Peptide derived from human TrkB

<400> SEQUENCE: 70

Asn Pro Asn Tyr Pro Asp Val Ile Tyr Glu Asp Tyr Gly Thr
1               5                   10
```

```
<210> SEQ ID NO 71
<211> LENGTH: 12
<212> TYPE: PRT
<213> ORGANISM: Artificial
<220> FEATURE:
<223> OTHER INFORMATION: Peptide derived from human TrkB

<400> SEQUENCE: 71

His Phe Ala Pro Thr Ile Thr Phe Leu Glu Ser Pro
1               5                   10

<210> SEQ ID NO 72
<211> LENGTH: 9
<212> TYPE: PRT
<213> ORGANISM: Artificial
<220> FEATURE:
<223> OTHER INFORMATION: TrkB_MPLLLLLPLLWAGALAG_H284-H430(D5-JM)-5His
      peptide from 283-291

<400> SEQUENCE: 72

Gly His Phe Ala Pro Thr Ile Thr Phe
1               5

<210> SEQ ID NO 73
<211> LENGTH: 8
<212> TYPE: PRT
<213> ORGANISM: Artificial
<220> FEATURE:
<223> OTHER INFORMATION: TrkB_MPLLLLLPLLWAGALAG_H284-H430(D5-JM)-5His
      peptide from 284-291

<400> SEQUENCE: 73

His Phe Ala Pro Thr Ile Thr Phe
1               5

<210> SEQ ID NO 74
<211> LENGTH: 25
<212> TYPE: PRT
<213> ORGANISM: Artificial
<220> FEATURE:
<223> OTHER INFORMATION: TrkB_MPLLLLLPLLWAGALAG_H284-H430(D5-JM)-5His
      peptide from 292-316

<400> SEQUENCE: 74

Leu Glu Ser Pro Thr Ser Asp His His Trp Cys Ile Pro Phe Thr Val
1               5                   10                  15

Lys Gly Asn Pro Lys Pro Ala Leu Gln
            20                  25

<210> SEQ ID NO 75
<211> LENGTH: 9
<212> TYPE: PRT
<213> ORGANISM: Artificial
<220> FEATURE:
<223> OTHER INFORMATION: TrkB_MPLLLLLPLLWAGALAG_H284-H430(D5-JM)-5His
      peptide from 316-324

<400> SEQUENCE: 75

Gln Trp Phe Tyr Asn Gly Ala Ile Leu
1               5

<210> SEQ ID NO 76
<211> LENGTH: 8
<212> TYPE: PRT
<213> ORGANISM: Artificial
<220> FEATURE:
```

<223> OTHER INFORMATION: TrkB_MPLLLLLPLLWAGALAG_H284-H430(D5-JM)-5His
      peptide from 317-324

<400> SEQUENCE: 76

Trp Phe Tyr Asn Gly Ala Ile Leu
1               5

<210> SEQ ID NO 77
<211> LENGTH: 7
<212> TYPE: PRT
<213> ORGANISM: Artificial
<220> FEATURE:
<223> OTHER INFORMATION: TrkB_MPLLLLLPLLWAGALAG_H284-H430(D5-JM)-5His
      peptide from 318-324

<400> SEQUENCE: 77

Phe Tyr Asn Gly Ala Ile Leu
1               5

<210> SEQ ID NO 78
<211> LENGTH: 15
<212> TYPE: PRT
<213> ORGANISM: Artificial
<220> FEATURE:
<223> OTHER INFORMATION: TrkB_MPLLLLLPLLWAGALAG_H284-H430(D5-JM)-5His
      peptide from 347-361

<400> SEQUENCE: 78

Gln Leu Asp Asn Pro Thr His Met Asn Asn Gly Asp Tyr Thr Leu
1               5                   10                  15

<210> SEQ ID NO 79
<211> LENGTH: 10
<212> TYPE: PRT
<213> ORGANISM: Artificial
<220> FEATURE:
<223> OTHER INFORMATION: TrkB_MPLLLLLPLLWAGALAG_H284-H430(D5-JM)-5His
      peptide from 349-358

<400> SEQUENCE: 79

Asp Asn Pro Thr His Met Asn Asn Gly Asp
1               5                   10

<210> SEQ ID NO 80
<211> LENGTH: 18
<212> TYPE: PRT
<213> ORGANISM: Artificial
<220> FEATURE:
<223> OTHER INFORMATION: TrkB_MPLLLLLPLLWAGALAG_H284-H430(D5-JM)-5His
      peptide from 351-368

<400> SEQUENCE: 80

Pro Thr His Met Asn Asn Gly Asp Tyr Thr Leu Ile Ala Lys Asn Glu
1               5                   10                  15

Tyr Gly

<210> SEQ ID NO 81
<211> LENGTH: 16
<212> TYPE: PRT
<213> ORGANISM: Artificial
<220> FEATURE:
<223> OTHER INFORMATION: TrkB_MPLLLLLPLLWAGALAG_H284-H430(D5-JM)-5His
      peptide from 363-378

<400> SEQUENCE: 81

Ala Lys Asn Glu Tyr Gly Lys Asp Glu Lys Gln Ile Ser Ala His Phe
1               5                   10                  15

<210> SEQ ID NO 82
<211> LENGTH: 19
<212> TYPE: PRT
<213> ORGANISM: Artificial
<220> FEATURE:
<223> OTHER INFORMATION: TrkB_MPLLLLLPLLWAGALAG_H284-H430(D5-JM)-5His
      peptide from 377-395

<400> SEQUENCE: 82

His Phe Met Gly Trp Pro Gly Ile Asp Asp Gly Ala Asn Pro Asn Tyr
1               5                   10                  15

Pro Asp Val

<210> SEQ ID NO 83
<211> LENGTH: 7
<212> TYPE: PRT
<213> ORGANISM: Artificial
<220> FEATURE:
<223> OTHER INFORMATION: TrkB_MPLLLLLPLLWAGALAG_H284-H430(D5-JM)-5His
      peptide from 379-385

<400> SEQUENCE: 83

Met Gly Trp Pro Gly Ile Asp
1               5

<210> SEQ ID NO 84
<211> LENGTH: 17
<212> TYPE: PRT
<213> ORGANISM: Artificial
<220> FEATURE:
<223> OTHER INFORMATION: TrkB_MPLLLLLPLLWAGALAG_H284-H430(D5-JM)-5His
      peptide from 379-395

<400> SEQUENCE: 84

Met Gly Trp Pro Gly Ile Asp Asp Gly Ala Asn Pro Asn Tyr Pro Asp
1               5                   10                  15

Val

<210> SEQ ID NO 85
<211> LENGTH: 18
<212> TYPE: PRT
<213> ORGANISM: Artificial
<220> FEATURE:
<223> OTHER INFORMATION: TrkB_MPLLLLLPLLWAGALAG_H284-H430(D5-JM)-5His
      peptide from 379-396

<400> SEQUENCE: 85

Met Gly Trp Pro Gly Ile Asp Asp Gly Ala Asn Pro Asn Tyr Pro Asp
1               5                   10                  15

Val Ile

<210> SEQ ID NO 86
<211> LENGTH: 19
<212> TYPE: PRT
<213> ORGANISM: Artificial
<220> FEATURE:
<223> OTHER INFORMATION: TrkB_MPLLLLLPLLWAGALAG_H284-H430(D5-JM)-5His
      peptide from 379-397

<400> SEQUENCE: 86

Met Gly Trp Pro Gly Ile Asp Asp Gly Ala Asn Pro Asn Tyr Pro Asp
1               5                   10                  15

Val Ile Tyr

```
<210> SEQ ID NO 87
<211> LENGTH: 20
<212> TYPE: PRT
<213> ORGANISM: Artificial
<220> FEATURE:
<223> OTHER INFORMATION: TrkB_MPLLLLLPLLWAGALAG_H284-H430(D5-JM)-5His
      peptide from 379-398

<400> SEQUENCE: 87

Met Gly Trp Pro Gly Ile Asp Asp Gly Ala Asn Pro Asn Tyr Pro Asp
1               5                   10                  15

Val Ile Tyr Glu
            20

<210> SEQ ID NO 88
<211> LENGTH: 18
<212> TYPE: PRT
<213> ORGANISM: Artificial
<220> FEATURE:
<223> OTHER INFORMATION: TrkB_MPLLLLLPLLWAGALAG_H284-H430(D5-JM)-5His
      peptide from 418-435

<400> SEQUENCE: 88

Pro Ser Thr Asp Val Thr Asp Lys Thr Gly Arg Glu His His His His
1               5                   10                  15

His His
```

US 11,078,287 B2

BINDING AGONIST FOR TREATMENT OF NEUROLOGICAL AND OTHER DISORDERS

FIELD OF THE INVENTION

The present invention relates to TrkB binding agonists, and to the use of such agonists in the treatment of neurological disorders and other disorders. The present invention also relates to specific TrkB binding agonists comprising CDRs, variable regions, heavy and light chains, and variant sequences thereof.

BACKGROUND OF THE INVENTION

Neurological disorders are increasing in incidence and prevalence worldwide, and as such therapies are in imminent need. However, neurological disorders are phenotypically heterogeneous, both in familial and sporadic forms, and often have an unknown etiology. Thus targeting a single pathological mechanism, is less likely to provide disease modification with a significant clinical benefit, unless the nature of the pathological mechanism is the key "driver" of the disease.

Several mechanisms and pathways have been implicated in neurological disorders such as neurological diseases, including accumulation of neurotoxic substances, inflammation, lipid metabolism, oxidative stress, autophagy, protein degradation and mitochondrial dysfunction. However, it remains unclear whether they are the cause of the disease or the consequence of the primary and/or secondary damage. Consequently, therapies based on some of these individual mechanisms have not been clinically successful. Many efforts to develop disease-modifying therapies for neurological diseases have followed a toxin-reducing approach given that accumulation of misfolded toxic proteins in the brain is considered to be a key pathogenic factor for some neurodegenerative diseases. However, clinical success by lowering toxic proteins has been limited, such as Aβ in Alzheimer's Disease, although recent trials in patients with mild disease show encouraging results.

Targeting pathogenesis (the biological mechanism(s) that lead to the diseased state) may be a suitable approach for prophylactic or preventative treatment; however, targeting pathophysiology (the endogenous biological mechanisms operating within the diseased state) may be a better approach for therapeutic intervention in a neurological disorder that is already present.

It is possible to use this alternative pathophysiological therapeutic approach by targeting the endogenous neurotrophic and neuroprotective pathways that play a role in neuronal survival, function, plasticity, and homeostasis. There is evidence indicating that endogenous mechanisms can be significantly down regulated in neurological disorders.

Neurotrophins are endogenous growth factors that regulate the development, maintenance and functions of the central and peripheral nervous systems (CNS and PNS respectively). The Nerve Growth Factor (NGF) family of ligands primarily signal through a high-affinity Trk receptor [TrkA for NGF, TrkB for BDNF (Brain Derived Neurotrophic Factor) and NT-4 (Neurotrophin 4, NT-4/5), TrkC for NT-3 (Neurotrophin 3)] and also by binding to the low-affinity pan-neurotrophin receptor, $p75^{NTR}$. Signal transduction through Trk receptors usually enhance cell survival, whereas signalling of neurotrophins through $p75^{NTR}$, in absence of Trk receptors, in general, facilitate apoptosis.

There is preclinical evidence supporting the role of the BDNF-TrkB pathway in promoting the survival and function of CNS neurons both in vitro and in vivo. Further, four clinical trials using BDNF have been conducted in ALS. In addition, a phase I, double-blind, placebo-controlled single ascending dose study in healthy volunteers with subcutaneous injection of a TrkB agonist antibody (Clinical Trial NCT01262690, sponsor: Pfizer) was terminated due to the emergent safety concern of sensory symptoms (no study results were published).

In summary, there remains a need for treatment of neurological disorders and other disorders where restoring or enhancing the BDNF-TrkB pathway by activating TrkB can be beneficial.

SUMMARY OF THE INVENTION

The present invention provides a TrkB binding agonist, wherein the agonist potentiates BDNF-induced and/or NT-4-induced agonism of TrkB. In one embodiment, the invention provides a TrkB binding agonist, wherein the agonist potentiates BDNF-induced agonism of TrkB.

The present invention also provides a TrkB binding agonist that binds to an epitope comprised within beta sheets A and G, and the region between beta sheets A and A', of the D5 domain of TrkB. In this context, the term "epitope" refers to that portion of the antigen (TrkB) that makes contact with the TrkB binding protein, for example that portion of TrkB that approaches the TrkB binding protein to less than or equal to 4.5 Å. In one embodiment, this TrkB binding agonist does not compete with BDNF. Agonists binding to this region of TrkB may:

a) interact with one or more of the following residues of human TrkB: Thr290, Glu293, Ser294, Asp358, Ser375, Lys372, Gln373, Glu341;
b) approach to less than or equal to 4.5 Å a residue from human TrkB selected from the group consisting of: T2886, I289, T290, F291, L292, E293, S294, K308, D358, E371, K372, Q373, I374, and S375;
c) bind to human TrkB in which a residue selected from the group: E210, F285, T288, T290, F291, E293, D370 and K372 are mutated with an altered affinity in comparison with human TrkB with no mutations;
d) bind to human TrkB and results in peptides derived from human TrkB containing part or the whole of the sequence from residues 284-291 (numbering according to full length human TrkB) being more resistant to deuterium incorporation compared to corresponding peptides derived from uncomplexed human TrkB or
e) bind to a peptide having the amino acid sequence set forth in SEQ ID NO: 71.

The present invention also provides a TrkB binding agonist that does binds to an epitope comprised within the juxta-membrane region (W381-H430) of TrkB. In this context, the term "epitope" refers to that portion of the antigen (TrkB) that makes contact with the TrkB binding protein, for example that portion of TrkB that approaches the TrkB binding protein to less than or equal to 4.5 Å. In one embodiment, this TrkB binding agonist does not compete with BDNF.

Agonists binding to this region may:
a) binds to human TrkB extracellular domain in which a residue selected from the group: N389, D394, V395, I396, Y397, E398, D399, Y400 and T402 is mutated with an altered affinity in comparison with human TrkB extracellular domain with no mutations;

b) binds to human TrkB and results in peptides derived from human TrkB containing part or the whole of the sequence from residues 385-398 (numbering according to full length human TrkB) being more resistant to deuterium incorporation compared to corresponding peptides derived from uncomplexed human TrkB; or c) binds to a peptide having the amino acid sequence set forth in SEQ ID NO: 69.

The present invention also provides a TrkB binding agonist that competes for binding to TrkB with a reference antibody having: (a) a heavy chain sequence of SEQ ID NO: 27 and a light chain sequence of SEQ ID NO: 28; or (b) a heavy chain sequence of SEQ ID NO: 29 and a light chain sequence of SEQ ID NO: 30; or (c) a heavy chain sequence of SEQ ID NO: 31 and a light chain sequence of SEQ ID NO: 32. In one embodiment, this TrkB binding agonist does not compete with BDNF. The present invention also provides a TrkB binding agonist that maintains levels of TrkB on the cell surface. In one embodiment, the agonist activates TrkB in the absence of BDNF.

The present invention also provides a TrkB binding agonist comprising (i) any one or a combination of CDRs selected from CDRH1, CDRH2, CDRH3 from SEQ ID NO: 27, and/or CDRL1, CDRL2, CDRL3 from SEQ ID NO:28; or (ii) a CDR variant of (i), wherein the variant has 1, 2, or 3 amino acid modifications in each CDR. In certain embodiments, particular CDRs are as present in SEQ ID NO: 27 or SEQ ID NO: 28 whilst other CDRs are variants of those present in SEQ ID NO: 27 or SEQ ID NO: 28. In one embodiment, the invention provides a TrkB binding agonist comprising:

(a) CDRL1 as present in SEQ ID NO: 28 or a variant thereof, which variant has 1, 2 or 3 amino acid modifications;

(b) CDRL3 as present in SEQ ID NO: 28 or a variant thereof, which variant has 1, 2 or 3 amino acid modifications; and (c) CDRH3 as present in SEQ ID NO: 27 or a variant thereof, which variant has 1, 2 or 3 amino acid modifications.

The present invention also provides a TrkB binding agonist comprising any one or a combination of the following CDRs: (a) CDRH1 of SEQ ID NO: 6; (b) CDRH2 of SEQ ID NO: 7; (c) CDRH3 of SEQ ID NO: 8; (d) CDRL1 of SEQ ID NO: 3; (e) CDRL2 of SEQ ID NO: 4; and/or (f) CDRL3 of SEQ ID NO: 5.

The present invention also provides a TrkB binding agonist comprising a VH region comprising a sequence at least 80% identical to the sequence of SEQ ID NO: 40 and/or a VL region comprising a sequence at least 76% identical to the sequence of SEQ ID NO: 41.

The present invention also provides a TrkB binding agonist comprising: (a) a Heavy Chain (HC) sequence at least 90% identical to SEQ ID NO: 42; and/or (b) a Light Chain (LC) sequence at least 85% identical to SEQ ID NO: 43.

The present invention also provides one or more nucleic acid sequences which encode the TrkB binding agonist as defined herein. In one embodiment, the present invention provides a nucleic acid sequence which encodes a TrkB binding agonist as defined herein.

The present invention also provides one or more expression vectors comprising the one or more nucleic acid sequences as defined herein. In one embodiment, the present invention provides an expression vector comprising a nucleic acid sequence which encodes a TrkB binding agonist as defined herein.

The present invention also provides a recombinant host cell comprising the one or more nucleic acid sequences as defined herein, or one or more expression vectors as defined herein. In one embodiment, the present invention provides a recombinant host cell comprising a nucleic acid sequence which encodes a TrkB binding agonist as defined herein, or an expression vector comprising a nucleic acid sequence which encodes a TrkB binding agonist as defined herein.

The present invention also provides a method for the production of the TrkB binding agonist as defined herein, which method comprises culturing the host cell as defined herein under conditions suitable for expression of said nucleic acid sequence or vector. In one embodiment of this method, the TrkB binding agonist is expressed and purified.

The present invention also provides a TrkB binding agonist produced by the method described herein.

The present invention also provides a pharmaceutical composition comprising the binding agonist as defined herein, and one or a combination of pharmaceutically acceptable carriers, excipients or diluents.

The present invention also provides a method of treating a neurological disorder in a subject in need thereof comprising administering to said subject a therapeutically effective amount of the TrkB binding agonist as defined herein, or the pharmaceutical composition as defined herein to the subject. In one embodiment, the subject is human.

The present invention also provides a method of treating a neurological disorder or other disorder where restoring or enhancing the BDNF-TrkB pathway by activating TrkB can be beneficial, in a subject in need thereof comprising administering to said subject a therapeutically effective amount of the TrkB binding agonist as defined herein, or the pharmaceutical composition as defined herein to the subject. In one embodiment, the subject is human.

The present invention also provides a method of treating a neurological disorder in a subject in need thereof comprising administering to said subject a therapeutically effective amount of a potentiator of BDNF-induced agonism of TrkB to the subject. In one embodiment, the subject is human.

The present invention also provides a method of treating a neurological disorder or other disorder where restoring or enhancing the BDNF-TrkB pathway by activating TrkB can be beneficial, in a subject in need thereof comprising administering to said subject a therapeutically effective amount of a potentiator of BDNF-induced agonism of TrkB to the subject. In one embodiment, the subject is human.

The present invention also provides a TrkB binding agonist as defined herein, or a pharmaceutical composition as defined herein for use in therapy.

The present invention also provides a TrkB binding agonist as defined herein, or a pharmaceutical composition as defined herein for use in the treatment of a neurological disorder or other disorder where restoring or enhancing the BDNF-TrkB pathway by activating TrkB can be beneficial.

The present invention also provides a TrkB binding agonist as defined herein, or a pharmaceutical composition as defined herein for use in the treatment of a neurological disorder.

The present invention also provides a potentiator of BDNF-induced agonism of TrkB, for use in therapy.

The present invention also provides a potentiator of BDNF-induced agonism of TrkB, for use in the treatment of a neurological disorder or other disorder where restoring or enhancing the BDNF-TrkB pathway by activating TrkB can be beneficial.

The present invention also provides a use of a TrkB binding agonist as defined herein, or a pharmaceutical composition as defined herein, in the manufacture of a medicament for the treatment of a neurological disorder.

The present invention also provides a use of a TrkB binding agonist as defined herein, or a pharmaceutical composition as defined herein, in the manufacture of a medicament for the treatment of neurological disorder or other disorder where restoring or enhancing the BDNF-TrkB pathway by activating TrkB can be beneficial.

The present invention also provides a use of a potentiator of BDNF-induced agonism of TrkB, in the manufacture of a medicament for the treatment of a neurological disorder.

The present invention also provides a use of a potentiator of BDNF-induced agonism of TrkB, in the manufacture of a medicament for the treatment of a neurological disorder or other disorder where restoring or enhancing the BDNF-TrkB pathway by activating TrkB can be beneficial.

The present invention also provides a method of treatment, a TrkB binding agonist, or the use, as described herein, wherein treatment comprises enhancement of: cell survival, and/or neuronal repair, and/or neuronal plasticity.

DETAILED DESCRIPTION OF THE INVENTION

Figure 1A:
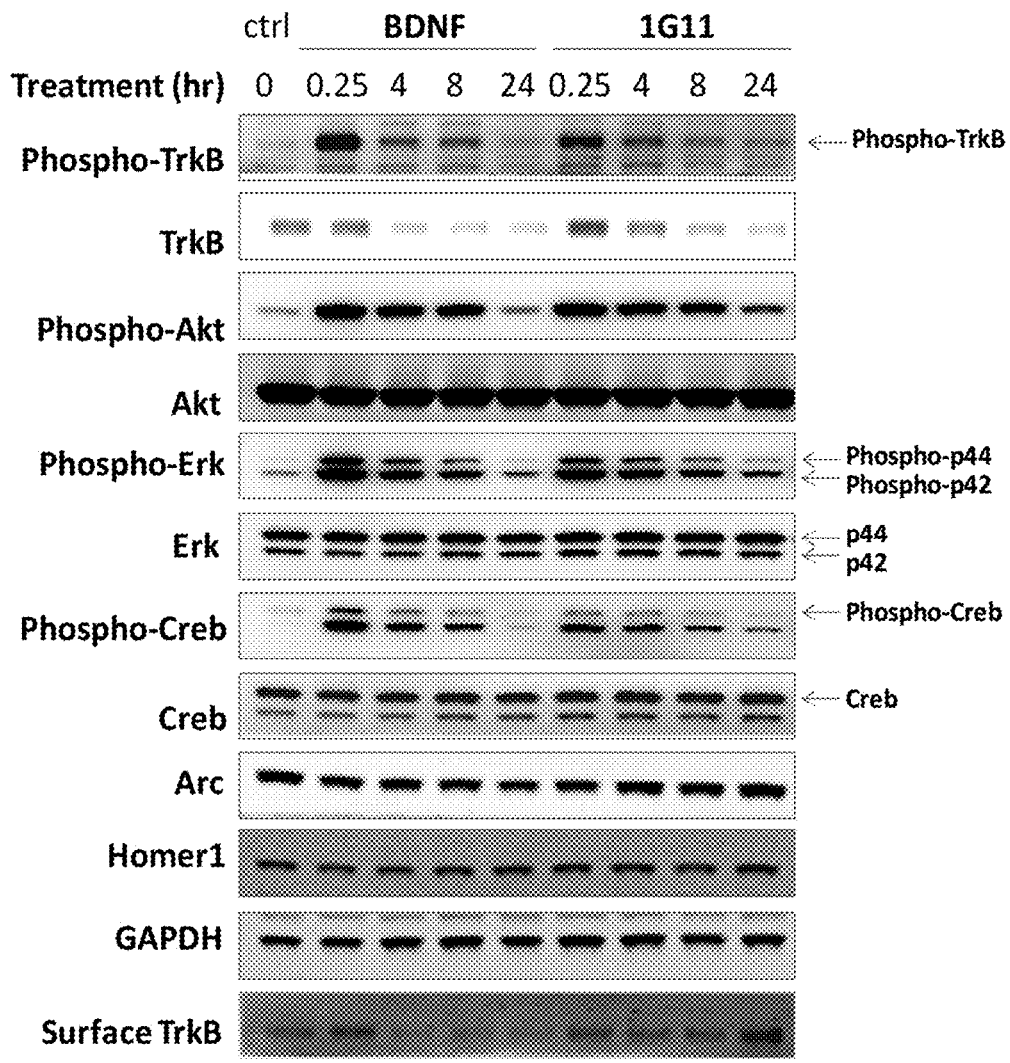
FIG. 1A: Western Blot of BDNF and 1G11 induced TrkB phosphorylation and TrkB downstream signalling and cell surface levels of TrkB in rat cortical neurons over time. Rat cortical neurons in culture (7 days in vitro) were treated with 0.8 nM BDNF or 7.3 nM 1G11 as indicated at 37° C. Cell lysates (30 μg protein) were resolved on a SDS-PAGE under reducing conditions and immunoblotted with antibodies as indicated. Glyceraldehyde-3-Phosphate Dehydrogenase (GAPDH) was used as internal control. For measuring cell surface levels of TrkB, rat cortical neurons following treatment with 1G11 were treated with sulfo-NHS-biotin for 1 hour on ice followed by lysis and isolation of biotinylated proteins using streptavidin agarose beads. Isolated proteins were resolved and immunoblotted with anti-TrkB antibody. Note: Ctrl, untreated zero time control with medium change.

"TrkB" as used herein refers to naturally occurring, endogenous or recombinant TrkB protein. TrkB is a receptor for the ligand brain-derived neurotrophic factor (BDNF) or neurotrophin-4 (NT-4/NT-4/5). Both BDNF and NT-4 can bind to TrkB, and can activate many common signalling pathways. The non-covalent homodimeric ligand BDNF or NT-4 activates TrkB, which is a receptor tyrosine kinase. Activated TrkB can regulate (a) cell survival, (b) neuronal repair, and/or (c) neuronal plasticity.

As described above, TrkB-BDNF signalling plays an important role in promoting the survival, repair, and plasticity of cells in the Central Nervous System (CNS) and Peripheral Nervous System (PNS). Though the causal factor/mechanisms in most neurological disorders are different, the survival and function of the different types of cells that can undergo degeneration are dependent on an efficient BDNF-TrkB signalling mechanism. Therefore, restoring or enhancing the BDNF-TrkB pathway by activating TrkB using an agonist is expected to promote cell survival, neuronal repair and neuronal plasticity to offer a differentiating treatment for disorders. Activating TrkB may mediate both central and peripheral mechanism of action.

BDNF levels have been reported to be decreased in many neurological and pathophysiological diseases and the phenotypes/deficits can be attributed to this reduction. Under BDNF deficient pathophysiological conditions, where TrkB receptor levels remain unaltered, a physiological cellular/system response could still be elicited if the administered therapeutic can: (i) activate (agonise) TrkB, (ii) not compete with the reduced levels of BDNF, (iii) potentiate the cellular signalling induced by the reduced physiological levels of BDNF, and/or (iv) maintain the cell surface levels of TrkB, which otherwise may potentially result in temporary desensitization to the therapeutic.

In the context of the present invention, the term "TrkB binding agonist" refers to a molecule that agonises or activates human full length TrkB (having the sequence set out in SEQ ID NO: 2) in the absence of BDNF or NT-4. The TrkB binding agonist may produce a similar biological effect as the natural ligand BDNF/NT-4 when it binds to the receptor. TrkB is a receptor tyrosine kinase and therefore elicits multiple cellular signalling pathways. Agonism may be measured by activation of TrkB, including measuring increased phosphorylated levels of TrkB (pTrkB), increased phosphorylated levels of Akt (p-Akt), increased phosphorylated levels of Erk (p-Erk), and/or increased phosphorylated levels of Creb (p-Creb). For example, the TrkB binding agonist may activate the TrkB receptor in the absence of BDNF or NT-4 resulting in pTrkB levels of at least 10%, at least 20% at least 25%, at least 30%, at least 40%, at least 50% or at least 60%, relative to BDNF maximal response (set at 100%). In one embodiment, the TrkB binding agonist may activate the TrkB receptor in the absence of BDNF or NT-4 resulting in pTrkB levels of at least 10%, at least 20% at least 25%, at least 30%, at least 40%, at least 50% or at least 60%, relative to NT-4 maximal response (set at 100%).

Affinity is the strength of binding of one molecule, e.g. the TrkB binding agonist, to another, e.g. its target antigen, at a single binding site. The binding affinity of a TrkB binding agonist to TrkB may be determined by equilibrium methods (e.g. enzyme-linked immunoabsorbent assay (ELISA) or radioimmunoassay (RIA)), or kinetics (e.g. BIACORE™ analysis). For example, the Biacore™ methods described in Example 1.1 (and data in Table 1) may be used to measure binding affinity.

Certain TrkB binding agonists of the invention exhibit an equilibrium dissociation constant to human TrkB or human TrkB ECD of (KD) of 100 nM or less, 50 nM or less, 25 nM or less, or 10 nM or less. The smaller the KD numerical value, the stronger the binding. The reciprocal of KD (i.e. 1/KD) is the equilibrium association constant (KA) having units M−1. A skilled person will appreciate that the larger the KA numerical value, the stronger the binding. The dissociation rate constant (kd) or "$k_{off}$" describes the stability of the TrkB binding agonist: TrkB complex, i.e. the fraction of complexes that decay per second. For example, the dissociation rate constant $k_{off}$ between certain TrkB agonists and human TrkB or human TrkB ECD is $10 \times 10^{-4}$/s or less, $9 \times 10^{-4}$/s or less, $8 \times 10^{-4}$/s or less, $7 \times 10^{-4}$/s or less, $6 \times 10^{-4}$/s or less, $5 \times 10^{-4}$/s or less, or $4 \times 10^{-4}$/s or less. The association rate constant (ka) or "$k_{on}$" describes the rate of TrkB binding agonist: TrkB complex formation. For example, the association rate constant $k_{on}$ between certain TrkB agonists and human TrkB or human TrkB ECD is $3 \times 10^4$/Ms or more, $4 \times 10^4$/Ms or more, $5 \times 10^4$/Ms or more, $6 \times 10^4$/Ms or more, or $7 \times 10^4$/Ms or more.

In one embodiment, the TrkB binding agonist specifically binds to full length human TrkB and does not bind to human TrkA or human TrkC or human p75NTR. The term "specifically binds" means that the TrkB binding agonist binds to TrkB with no or insignificant binding to other (for example, unrelated) proteins. The TrkB binding agonist described herein may bind to TrkB with at least 10, 25, 50, 100, or 1000 fold greater affinity than they bind to TrkA, TrkC and/or p75NTR. It will be appreciated that this distinguishes these TrkB binding agonists from BDNF, which can activate both TrkB and p75NTR (which facilitates cell death).

Certain TrkB agonists of the invention potentiate BDNF-induced and/or NT-4-induced TrkB agonism. "Potentiate" is used herein to mean that BDNF-induced agonism and/or NT-4-induced agonism of TrkB is more effective in the presence of the TrkB agonist. BDNF-induced agonism can be measured by assessing activation of TrkB, for example cellular signalling. A saturating concentration (i.e. EC100) of BDNF or NT-4 can be used to benchmark 100% activation of TrkB for each ligand in the absence of the TrkB binding agonist. Potentiation of BDNF-induced agonism can be defined as BDNF-induced activation of TrkB of more than 100% in the presence of a TrkB binding agonist and a saturating concentration (EC100) of BDNF. A saturating concentration of BDNF that can be used is 10 nM (EC100). In one example, 100% activation of TrkB represents TrkB activation using BDNF at 10 nM EC100. Potentiation of NT-4-induced agonism can be defined as NT-4-induced activation of TrkB of more than 100% in the presence of a TrkB binding agonist and a saturating concentration (EC100) of NT-4. Activation of TrkB can be measured by determining the level of phosphorylation of TrkB (pTrkB). The phosphorylation of TrkB in the presence of a saturating concentration of BDNF may be at least 110% in the presence of the TrkB binding agonist, compared with 100% in the absence of the TrkB binding agonist. For example, the phosphorylation of TrkB in the presence of a saturating concentration of BDNF may be at least 115%, at least 120%, at least 125%, at least 130%, at least 135%, at least 140%, at least 145%, or at least 150% in the presence of the TrkB binding agonist, compared with 100% in the absence of the TrkB binding agonist. pTrkB levels may be around 130% in the presence of the TrkB binding agonist and in the presence of a saturating concentration of BDNF. pTrkB levels may be around 160% in the presence of the TrkB binding agonist and in the presence of a saturating concentration of BDNF. pTrkB levels may be around 120% in the presence of the TrkB binding agonist and in the presence of a saturating concentration of BDNF.

It should be noted that although the potentiation effect can only be measured in vitro in the presence of a saturating concentration of BDNF, this saturating concentration of BDNF is not thought to be necessary in a clinical setting. It is hypothesised that the potentiation effect of the TrkB binding agonist should be present at any concentration of BDNF. Under BDNF deficient pathophysiological conditions, where TrkB receptor levels remain unaltered, a physiological response will be beneficial if the TrkB binding agonist can potentiate the cellular signalling induced by the reduced physiological levels of BDNF.

Certain TrkB agonists of the invention maintain TrkB levels on the cell surface. Activated tyrosine kinase receptors typically undergo endocytosis followed by degradation resulting in down regulation of the cell surface receptors thereby becoming non-responsive to the ligand temporarily to maintain cellular homeostasis, which is the case for BDNF's activation effect upon TrkB. The TrkB binding agonist may maintain the cell surface levels of TrkB over time in the presence of the agonist. For example, the cell surface levels of TrkB may be maintained for at least 2 hours, at least 4 hours, at least 6 hours, at least 8 hours, or at least 10 hours. The TrkB binding agonist may increase the cell surface levels of TrkB over time in the presence of the agonist. For example, the cell surface levels of TrkB may be enhanced for at least 5 hours, at least 10 hours, at least 15 hours, at least 20 hours, or at least 25 hours. The TrkB binding agonist may increase the available cell surface levels of TrkB to be activated by agonist; and/or (b) inhibit activated TrkB receptor endocytosis and degradation. Under BDNF deficient pathophysiological conditions, where TrkB receptor levels remain unaltered, a physiological response will be beneficial if the therapeutic TrkB binding agonist could activate TrkB without altering the cell surface levels of TrkB, which otherwise may potentially result in temporary desensitization to the TrkB agonist.

Certain TrkB binding agonist does not compete with BDNF and/or NT-4 for binding to TrkB. Competition between the TrkB binding agonist and BDNF or NT-4 may be determined by a functional assay to assess activation of TrkB, for example, by measuring the TrkB binding agonist's activation effect on TrkB by TrkB phosphorylation both in the presence and absence of BDNF or NT-4. In one embodiment, a TrkB binding agonist that does not compete with BDNF will cause no change in TrkB phosphorylation upon increasing concentrations of the agonist in the presence of saturating BDNF concentration (e.g. 10 nM, EC100). A TrkB binding agonist that does compete with BDNF will cause reduced TrkB phosphorylation upon increasing concentrations of the agonist in the presence of saturating BDNF concentration (e.g. 10 nM, EC100). In one embodiment, the TrkB binding agonist is non competitive with BDNF where the total levels of phosphorylated TrkB in presence of agonist and a saturating concentration (EC100) BDNF is similar to the levels of phosphorylatedTrkB in presence of the saturating concentration of BDNF alone. i.e. Total pTrkB ($EC_{100}$BDNF+ agonist)≈Total pTrkB ($EC_{100}$BDNF). Similarly, in one embodiment, the TrkB binding agonist is non competitive with NT-4 where the total levels of phosphorylated TrkB in presence of agonist and a saturating concentration (EC100) NT-4 is similar to the levels of phosphorylatedTrkB in presence of the saturating concentration of NT-4 alone. i.e. Total pTrkB ($EC_{100}$NT-4+ agonist)≈Total pTrkB ($EC_{100}$NT-4). Levels of phosphorylated TrkB are considered to be similar where the mean total pTrkB measured in the presence of agonist and saturating levels of either BDNF or NT-4 is within the range (mean total pTrkB measured in the presence of saturating levels of either BDNF or NT-±3 standard deviations). In one embodiment, mean total pTrkB measured in the presence of agonist and saturating levels of either BDNF or NT-4 is within the range (mean total pTrkB measured in the presence of saturating levels of either BDNF or NT-4±2 standard deviations). In another embodiment, mean total pTrkB measured in the presence of agonist and saturating levels of either BDNF or NT-4 is within the range (mean total pTrkB measured in the presence of saturating levels of either BDNF or NT-4±1 standard deviation). In the foregoing embodiment, the mean total levels of phosphorylated pTrkB are calculated based on at least three readings, and the larger of the two standard deviations (i.e. the standard deviation calculated in the presence of agonist and the standard deviation calculated in the absence of agonist) is used. In another embodiment, levels of phosphorylated TrkB are considered to be similar where the mean total pTrkB measured in the presence of agonist and saturating levels of either BDNF or NT-4 and the mean total pTrkB measured in the presence of saturating levels of BDNF or NT-4 differ by less than 10%. In another embodiment, levels of phosphorylated TrkB are considered to be similar where the mean total pTrkB measured in the presence of agonist and saturating levels of either BDNF or NT-4 and the mean total pTrkB measured in the presence of saturating levels of BDNF or NT-4 differ by less than 5%. A TrkB binding agonist that does not compete with BDNF or NT-4 for binding to TrkB is beneficial in a clinical setting, since the TrkB agonist could activate TrkB and not compete with the reduced levels of BDNF (or NT-4). Thus, BDNF and NT-4 can continue to play a physiological role, in addition to the TrkB binding agonist.

Alternatively, competition between the TrkB binding agonist and BDNF or NT-4 may be determined by competition ELISA, FMAT or BIAcore assays designed to test whether the TrkB binding agonist and BDNF bind to the same or overlapping epitopes, whether there is steric inhibition of binding, or whether binding of the first molecule induces a conformational change in TrkB that prevents or reduces binding of the second molecule. Competition between the TrkB binding agonist and BDNF or NT-4 for binding to TrkB may be none or minimal (i.e. partial). In one embodiment, TrkB-ECD may be immobilized on a chip surface and either BDNF or NT-4 injected into flow cells. The TrkB binding agonist was then injected and its binding capacity to TrkB-ECD in presence of the BDNF or NT-4 was assessed. Competition may be categorised as: "no" with less than 20% binding of the TrkB agonist; "partial" with 20-60% binding of the TrkB agonist; and "yes" with more than 60% binding of the TrkB agonist.

Certain TrkB binding agonists of the invention may show cross-reactivity between human TrkB and TrkB from another species. For example, the TrkB binding agonist specifically binds human, murine, rat, and cynomolgus TrkB. This is particularly useful, since drug development typically requires testing of lead drug candidates in mouse systems before the drug is tested in humans. The provision of a drug that can bind human, murine, rat, and cynomolgus species allows one to test results in these system and make side-by-side comparisons of data using the same drug. This avoids the complication of needing to find a drug that works for example against mouse TrkB and a separate drug that works against human TrkB, and also avoids the need to compare results using non-identical drugs. Certain TrkB binding agonists exhibit less than or equal to a 5 fold difference, or less than or equal to a 2-fold difference in EC50 in the phosphorylation of human and rat TrkB. Certain TrkB binding agonists exhibit less than or equal to a 5 fold difference, or less than or equal to a 2-fold difference in EC50 in the phosphorylation of human and mouse TrkB. Certain TrkB binding agonists exhibit less than or equal to a 5 fold difference, or less than or equal to a 2-fold difference in EC50 in the phosphorylation of human and cynomolgus TrkB. In one embodiment, the EC50 values are the mean of at least 3 experiments.

The TrkB binding agonist may bind to a TrkB epitope that is in close proximity to the BDNF binding site of TrkB, in particular close to the specificity patch that binds to the N-terminus of the ligand. The TrkB binding agonist may bind to TrkB and enhance or stabilise further binding between BDNF and TrkB (trimeric complex of agonist:ligand:receptor). The TrkB binding agonist may be a TrkB-BDNF potentiator, which is non-competitive with BDNF. The TrkB binding agonist may bind to specific epitopes comprised within the D5 domain of TrkB and/or JuxtaMembrane (JM) region of TrkB; and/or compete for binding to TrkB with a reference antibody. It is possible that binding to these epitopes stabilises TrkB in an active conformation. The TrkB agonists may (a) increase the available cell surface levels of TrkB; and/or (b) inhibit activated TrkB receptor endocytosis and degradation.

Therefore a TrkB binding agonist is described that: (i) activates TrkB in the absence of BDNF, (ii) does not compete with BDNF, (iii) potentiates BDNF-induced or NT-4-induced agonism of TrkB, and/or (iv) maintains the cell surface level of TrkB.

The TrkB primary amino acid sequence is highly conserved across mouse, rat, cynomolgus and human (95% across the full-length sequence), and particularly conserved in the extracellular domain (TrkB-ECD). The TrkB-ECD includes 5 domains (D1-D3: C32-C194; D4: G195-V283; D5: H284-G380) and a short juxtamembrane JM region (W381-H430). The D5 domain of TrkB can replace full length TrkB for binding to the ligand (BDNF/NT-4). There are two contact regions within the ligand binding domain (LBD) of TrkB: the "conserved patch" and the "specificity patch". The contact residues of TrkB D5 in the conserved patch are from the loops between AB, C'D and EF beta sheets, and the C-terminus of the D5 domain. The conserved patch of TrkB binds to the stalk of the ligand (BDNF/NT-4). The contact residues of TrkB D5 in the specificity patch are from the external face of the ABED beta sheet. The specificity patch of TrkB binds to the N-terminus of the ligand (BDNF/NT-4) which is disordered in the unliganded form and becomes ordered upon binding to TrkB.

Most definitions of the term "epitope" specify that the epitope is the part of the antigen that is in contact with a binding protein, such as the TrkB agonist (see, for example, Essential Immunology, Sixth Edition, Blackwell Scientific Publishing, 1988, Ed. Roitt, Chapter 4). Other definitions refer to the part of the antigen that is bound by the binding protein. The terms "contact" and "bound" might imply that an epitope should properly only consist of residues that directly interact with the antibody or fragment via non-covalent interactions such as electrostatics (hydrogen bonding, ionic), Van de Waals forces, n-effects and hydrophobic bonds. On such a strict interpretation, an epitope would not include residues that do not interact, but are in other ways critical for the interaction between antigen and binding protein. For example, certain residues in the antigen might be required to be very small (e.g. glycine) to permit the close interaction required to facilitate direct interaction between other residues of the antigen and antibody (or fragment). Similarly, certain residues (e.g. proline) may be required for the antigen sequence to adopt the correct conformation to permit binding.

In fact, most of the techniques typically performed in order to identify "epitope" information do not (and cannot) distinguish between interacting residues and residues that are critical in other ways. The following techniques are commonly used:
1. Binding of antibodies or fragments thereof to peptides derived from the antigen (wherein peptides that exhibit significant binding are considered to contain "the epitope").
2. Hydrogen deuterium exchange (wherein peptides derived from complexed antigen that are resistant to deuterium incorporation compared to uncomplexed antigen are deemed to contain "the epitope")
3. Mutagenesis studies (e.g. alanine scanning mutagenesis, wherein mutated positions in the antigen significantly alter binding to the binding protein are deemed to form part of "the epitope").

As will be apparent to the skilled person, only techniques with atomic level resolution (e.g. X-ray crystallography, NMR, electron microscopy) are capable of distinguishing between residues that interact and those that are in other ways important. However, even though these are the only techniques capable of giving information on the epitope according to a strict definition, it is submitted that the other techniques nonetheless provide useful information on residues/sequences that are important for binding to the target.

The TrkB binding agonist, 1G11, described in the examples has several desirable properties as follows:
1. Potentiates BDNF-induced and NT-4-induced agonism
2. Maintains cell surface levels of TrkB
3. Cross reactivity with cynomolgus TrkB 1G11 has been shown by X ray crystallography to closely approach residues T288, F291, K372 and E293. T288 and T291 are located in D5 beta sheet A; E293 is located between D5 beta sheets A and A'; and K372 is located in D5 beta sheet G. For example, the TrkB binding agonist may bind to an epitope which comprises residues T288, F291, K372, E293, F285, T290 and D370. F285 and T290 are located in D5 beta sheet A. D370 is located in D5 beta sheet G. Thus, the "epitope" would appear to be comprised within beta sheets A and G, and the region between beta sheets A and A' of the D5 domain of TrkB. Other TrkB binding agonists contacting this same "epitope" may be expected to have similar biological activity. Such binding proteins would be highly desirable.

Accordingly, in one embodiment, the TrkB binding agonist may:
a) interact with one or more of the following residues of human TrkB: Thr290, Glu293, Ser294, Asp358, Ser375, Lys372, Gln373 and Glu341;
b) approach to less than or equal to 4.5 Å a residue from human TrkB selected from the group consisting of: T288, I289, T290, F291, L292, E293, S294, K308, D358, E371, K372, Q373, I374, and S375;
c) bind to human TrkB extracellular domain in which a residue selected from the group: E210, F285, T288, T290, F291, E293, D370 and K372 (numbering according to full length human TrkB) is mutated with an altered affinity in comparison with human TrkB extracellular domain with no mutations;
d) bind to human TrkB and results in peptides derived from human TrkB containing part or the whole of the sequence from residues 284-291 (numbering according to full length human TrkB) being more resistant to deuterium incorporation compared to corresponding peptides derived from uncomplexed human TrkB; or
e) bind to a peptide having the amino acid sequence set forth in SEQ ID NO: 71.

In one embodiment, the TrkB binding agonist may interact with one or more, two or more, or three or more of the following residues of human TrkB: Thr290, Glu293, Ser294, Asp358, Ser375, Lys372, Gln373 and Glu341. In one embodiment, the invention provides a TrkB binding agonist that interacts with Glu293 and optionally with one or more, or two or more further residues selected from the group consisting of: Thr290, Ser294, Asp358, Ser375, Lys372, Gln373, Glu341. In another embodiment, the invention provides a TrkB binding agonist that interacts with Thr290 and Glu 293, or Glu293 and Ser 294, or Thr290, Glu293 and Ser294.

In the above embodiments, the interaction may be a direct interaction or an indirect interaction via water. In one embodiment, the interaction is a direct interaction. In the context of this invention, a direct interaction is a hydrogen bond between the TrkB binding agonist and the named residue(s) of full length human TrkB. However, it should be noted that the information on interacting residues need not be derived from full length human TrkB. For example, human TrkB extracellular domain or the D5-JM domain of human TrkB may be used. Interacting residues may be identified by any technique capable of atomic level resolution. In one embodiment, interacting residues are identified by X-ray crystallography.

In one embodiment, the invention provides a TrkB binding agonist that approaches to less than or equal to 4.5 Å one or more, two or more or three or more residues from human TrkB selected from the group consisting of: T288, I289, T290, F291, L292, E293, S294, K308, D358, E371, K372, Q373, I374, and S375. In one embodiment, the invention provides a TrkB binding agonist that approaches to less than or equal to 4.5 Å Glu293 and optionally one or more, or two or more further residues selected from the group consisting of: T288, I289, T290, F291, L292, S294, K308, D358, E371, K372, Q373, I374, and S375. In one embodiment, the invention provides a TrkB binding agonist that approaches to less than or equal to 4.5 Å Thr290 and Glu 293, or Glu293 and Ser 294, or Thr290, Glu293 and Ser294. In the above embodiment, the proximity analysis may be conducted on structures identified by any technique capable of atomic level resolution e.g. X ray crystallography. The residues of TrkB are numbered as they would be in full length human TrkB. However, it should be noted that the information on proximity to the TrkB binding agonist need not be derived from full length human TrkB. For example, human TrkB extracellular domain or the D5-JM domain of human TrkB may be used.

In one embodiment, the invention provides a TrkB binding agonist that binds to human TrkB extracellular domain in which a residue selected from the group: E210, F285, T288, T290, F291, E293, D370 and K372 (numbering according to full length human TrkB) is mutated with an altered affinity in comparison with human TrkB extracellular domain with no mutations. In one embodiment, the invention provides a TrkB binding agonist that binds to human TrkB extracellular domain in which a residue selected from the group: E210, T288, F291, E293, D370 and K372 is mutated with an altered affinity in comparison with human TrkB extracellular domain with no mutations. In one embodiment, the invention provides a TrkB binding agonist that binds to human TrkB extracellular domain in which a residue selected from the group: F291 and E293 is mutated with an altered affinity in comparison with human TrkB extracellular domain with no mutations. Binding may be assessed by any suitable method, for example, SPR or ELISA. The TrkB may be tagged (e.g. biotinylated) to facilitate the binding assay, but its sequence may not be extended by additional amino acids. The term "altered affinity" refers to the situation where the TrkB binding agonist exhibits substantially reduced or substantially increased affinity for the mutated version when compared with human wild type TrkB extracellular domain. A substantial increase in affinity is where the mean $K_D$ for the mutated version measured on the basis of at least three readings is less than or equal to the mean $K_D$ for human wild type TrkB extracellular domain measured on the basis of at least three readings minus one standard deviation (the larger of the standard deviations for the wild type or mutated version should be used). In one embodiment, a substantial increase in affinity is where the mean $K_D$ for the mutated version measured on the basis of at least three readings is less than or equal to the mean $K_D$ for human wild type TrkB extracellular domain measured on the basis of at least three readings minus two standard deviations (the larger of the standard deviations for the wild type or mutated version should be used). In a further embodiment, a substantial increase in affinity is where the mean $K_D$ for the mutated version measured on the basis of at least three readings is less than or equal to the mean $K_D$ for human wild type TrkB extracellular domain measured on the basis of at least three readings minus three standard deviations (the larger of the standard deviations for the wild type or mutated version should be used). In one embodiment, a substantial increase in affinity is where the mean $K_D$ for the mutated version measured on the basis of at least three readings is at least 3 fold less than the mean $K_D$ for human wild type TrkB extracellular domain measured on the basis of at least three readings. In another embodiment, a substantial increase in affinity is where the mean $K_D$ for the mutated version measured on the basis of at least three readings is at least 5 fold less than the mean $K_D$ for human wild type TrkB extracellular domain measured on the basis of at least three readings. In yet another embodiment, a substantial increase in affinity is where the mean $K_D$ for the mutated version measured on the basis of at least three readings is at least 10 fold less than the mean $K_D$ for human wild type TrkB extracellular domain measured on the basis of at least three readings. A substantial decrease in affinity is where the mean $K_D$ for the mutated version measured on the basis of at least three readings is greater than or equal to the mean $K_D$ for human wild type TrkB extracellular domain measured on the basis of at least three readings plus one standard deviation (the larger of the standard deviations for the wild type or mutated version should be used). In one embodiment, a substantial decrease in affinity is where the mean $K_D$ for the mutated version measured on the basis of at least three readings is greater than or equal to the mean $K_D$ for human wild type TrkB extracellular domain measured on the basis of at least three readings plus two standard deviations (the larger of the standard deviations for the wild type or mutated version should be used). In a further embodiment, a substantial decrease in affinity is where the mean $K_D$ for the mutated version measured on the basis of at least three readings is greater than or equal to the mean $K_D$ for human wild type TrkB extracellular domain measured on the basis of at least three readings plus three standard deviations (the larger of the standard deviations for the wild type or mutated version should be used). In one embodiment, a substantial decrease in affinity is where the mean $K_D$ for the mutated version measured on the basis of at least three readings is at least 3 fold greater than the mean $K_D$ for human wild type TrkB extracellular domain measured on the basis of at least three readings. In another embodiment, a substantial decrease in affinity is where the mean $K_D$ for the mutated version measured on the basis of at least three readings is at least 5 fold greater than the mean $K_D$ for human wild type TrkB extracellular domain measured on the basis of at least three readings. In yet another embodiment, a substantial decrease in affinity is where the mean $K_D$ for the mutated version measured on the basis of at least three readings is at least 10 fold greater than the mean $K_D$ for human wild type TrkB extracellular domain measured on the basis of at least three readings. In one embodiment, altered affinity refers to reduced affinity.

In one embodiment, the invention provides a TrkB binding protein that binds to human TrkB and results in peptides derived from human TrkB containing part or the whole of the sequence from residues 284-291 (numbering according to full length human TrkB) being more resistant to deuterium incorporation compared to corresponding peptides derived from uncomplexed human TrkB. In one embodiment, resistance to deuterium incorporation is assessed at a time point of between 15 and 300 seconds after dilution into deuterated buffer (e.g. at one of 15, 60 or 300 seconds).

Whilst the data from alanine scanning mutagenesis and X-ray crystallography points to a discontinuous epitope for 1G11, it is noted that most interactions would appear to be in the most N-terminal portion of this discontinuous epitope. This is also the portion that is most strongly protected from hydrogen deuterium exchange. For this reason, it is expected that binding proteins binding just to this N-terminal region of the epitope of 1G11 may have similar properties to 1G11. Accordingly, in one embodiment, the invention provides a TrkB binding agonist that binds to a peptide having the amino acid sequence set forth in SEQ ID NO: 71 (a peptide comprising the N-terminal region of the discontinuous epitope of antibody 1G11). In this context, the term "binds to" requires a binding response substantially greater than observed for any non-overlapping peptide of equivalent length derived from human TrkB extracellular domain. Binding may be assessed by any suitable method, for example ELISA. The peptides may be tagged (e.g. biotinylated) to facilitate the binding assay, but the sequence may not be extended by additional amino acids. It should be noted that the requirement to bind to a peptide having the sequences specified does not necessarily mean that the binding protein may not interact with residues outside of this sequence or, for example, protect them from e.g. deuterium uptake provided that an "all or nothing" binding response is achieved (i.e. the levels of binding achieved by peptides having the sequence set forth in SEQ ID NO:71 being substantially greater than levels achieved by other, non-overlapping TrkB peptides). A substantially greater binding response in the context of this invention refers to the situation where the mean $K_D$ for a peptide containing the sequence set forth in SEQ ID NO: 69 (or 70) on the basis of at least three readings is less than or equal to the mean $K_D$ for the non-overlapping TrkB peptides measured on the basis of at least three readings minus one standard deviation (the largest standard deviation observed for any peptide being used). In one embodiment, the mean $K_D$ for a peptide containing the sequence set forth in SEQ ID NO: 71 on the basis of at least three readings is less than or equal to the mean $K_D$ for the non-overlapping TrkB peptides measured on the basis of at least three readings minus two standard deviations (the largest standard deviation observed for any peptide being used). In a further embodiment, the mean $K_D$ for a peptide containing the sequence set forth in SEQ ID NO: 71 on the basis of at least three readings is less than or equal to the mean $K_D$ for the non-overlapping TrkB peptides measured on the basis of at least three readings minus three standard deviations (the largest standard deviation observed for any peptide being used). In one embodiment, the mean $K_D$ for a peptide containing the sequence set forth in SEQ ID NO: 71 on the basis of at least three readings is at least 3 fold lower than the mean $K_D$ for the non-overlapping TrkB peptides measured on the basis of at least three readings. In another embodiment, the mean $K_D$ for a peptide containing the sequence set forth in SEQ ID NO: 71 on the basis of at least three readings is at least 5 fold lower than the mean $K_D$ for the non-overlapping TrkB peptides measured on the basis of at least three readings. In another embodiment, the mean $K_D$ for a peptide containing the sequence set forth in SEQ ID NO: 71 on the basis of at least three readings is at least 10 fold lower than the mean $K_D$ for the non-overlapping TrkB peptides measured on the basis of at least three readings.

1G11 and TrkB binding agonists binding to a similar epitope may bind to an epitope which is located on TrkB D5 domain proximal to the BDNF/NT4 "conserved patch" ligand binding site (loops between AB, C'D and EF beta sheets, and the C-terminus of the D5 domain), and close to the BDNF/NT4 "specificity patch" ligand binding site (external face of the ABED beta sheet). The N-terminus of BDNF potentially protrudes into a space between TrkB and these TrkB binding agonist. Such TrkB binding agonist might be able to interact with the N-terminus of BDNF, in addition to binding to TrkB, possibly stabilising the ternary complex leading to potentiation of the BDNF functional response. Alternatively, such TrkB binding agonist may stabilise the interaction between TrkB and BDNF, by binding not at the ligand binding domain, but close to it.

The TrkB binding agonists, 3A3 and 8E5 described in the examples are also capable of potentiating BDNF-induced agonism. Alanine scanning mutagenesis identifies certain residues in TrkB critical for 3A3 binding. Because 3A3 and 8E5 share certain properties and compete for binding to TrkB, it is believed that they may have overlapping "epitopes". Based on the data for 3A3, the "epitope" comprises residues E398, Y397, D399, Y400, D394, and I396. For example, the TrkB binding agonist may bind to an epitope which comprises residues E398, Y397, D399, and Y400. For example, the TrkB binding agonist may bind to an epitope which comprises residues E398, Y397, D399, Y400, D394, I396, V395, N389, and T402. These residues fall in the juxta-membrane (JM) region (W381-H430). The JM region is, in the absence of any crystal structure, assumed to be a long flexible linker region. It is thought that the JM region may also be important for binding to the ligand. Other TrkB binding agonists contacting this same "epitope" may be expected to have similar biological activity. Such binding proteins would be highly desirable.

Accordingly, in one embodiment, the TrkB binding agonist may:

a) bind to human TrkB extracellular domain in which a residue selected from the group: N389, D394, V395, I396, Y397, E398, D399, Y400 and T402 is mutated with an altered affinity in comparison with human TrkB extracellular domain with no mutations;

b) bind to human TrkB and results in peptides derived from human TrkB containing part or the whole of the sequence from residues 385-398 (numbering according to full length human TrkB) being more resistant to deuterium incorporation compared to corresponding peptides derived from uncomplexed human TrkB; or c) bind to a peptide having the amino acid sequence set forth in SEQ ID NO: 69.

In one embodiment, the invention provides a TrkB binding agonist that binds to human TrkB extracellular domain in which a residue selected from the group: N389, D394, V395, I396, Y397, E398, D399, Y400 and T402 (numbering according to full length human TrkB) is mutated with an altered affinity in comparison with human TrkB extracellular domain with no mutations. In one embodiment, the invention provides a TrkB binding agonist that binds to human TrkB extracellular domain in which a residue selected from the group: D394, I396, Y397, E398, D399 and Y400 is mutated with an altered affinity in comparison with human TrkB extracellular domain with no mutations. In one embodiment, the invention provides a TrkB binding agonist that binds to human TrkB extracellular domain in which a residue selected from the group: Y397, E398, D399 and Y400 is mutated with an altered affinity in comparison with human TrkB extracellular domain with no mutations. Binding may be assessed by any suitable method, for example, SPR or ELISA. The TrkB may be tagged (e.g. biotinylated) to facilitate the binding assay, but its sequence may not be extended by additional amino acids. The term "altered affinity" refers to the situation where the TrkB binding agonist exhibits substantially reduced or substantially increased affinity for the mutated version when compared with human wild type TrkB extracellular domain. A substantial increase in affinity is where the mean $K_D$ for the mutated version measured on the basis of at least three readings is less than or equal to the mean $K_D$ for human wild type TrkB extracellular domain measured on the basis of at least three readings minus one standard deviation (the larger of the standard deviations for the wild type or mutated version should be used). In one embodiment, a substantial increase in affinity is where the mean $K_D$ for the mutated version measured on the basis of at least three readings is less than or equal to the mean $K_D$ for human wild type TrkB extracellular domain measured on the basis of at least three readings minus two standard deviations (the larger of the standard deviations for the wild type or mutated version should be used). In a further embodiment, a substantial increase in affinity is where the mean $K_D$ for the mutated version measured on the basis of at least three readings is less than or equal to the mean $K_D$ for human wild type TrkB extracellular domain measured on the basis of at least three readings minus three standard deviations (the larger of the standard deviations for the wild type or mutated version should be used). In one embodiment, a substantial increase in affinity is where the mean $K_D$ for the mutated version measured on the basis of at least three readings is at least 3 fold less than the mean $K_D$ for human wild type TrkB extracellular domain measured on the basis of at least three readings. In another embodiment, a substantial increase in affinity is where the mean $K_D$ for the mutated version measured on the basis of at least three readings is at least 5 fold less than the mean $K_D$ for human wild type TrkB extracellular domain measured on the basis of at least three readings. In yet another embodiment, a substantial increase in affinity is where the mean $K_D$ for the mutated version measured on the basis of at least three readings is at least 10 fold less than the mean $K_D$ for human wild type TrkB extracellular domain measured on the basis of at least three readings. A substantial decrease in affinity is where the mean $K_D$ for the mutated version measured on the basis of at least three readings is greater than or equal to the mean $K_D$ for human wild type TrkB extracellular domain measured on the basis of at least three readings plus one standard deviation (the larger of the standard deviations for the wild type or mutated version should be used). In one embodiment, a substantial decrease in affinity is where the mean $K_D$ for the mutated version measured on the basis of at least three readings is greater than or equal to the mean $K_D$ for human wild type TrkB extracellular domain measured on the basis of at least three readings plus two standard deviations (the larger of the standard deviations for the wild type or mutated version should be used). In a further embodiment, a substantial decrease in affinity is where the mean $K_D$ for the mutated version measured on the basis of at least three readings is greater than or equal to the mean $K_D$ for human wild type TrkB extracellular domain measured on the basis of at least three readings plus three standard deviations (the larger of the standard deviations for the wild type or mutated version should be used). In one embodiment, a substantial decrease in affinity is where the mean $K_D$ for the mutated version measured on the basis of at least three readings is at least 3 fold greater than the mean $K_D$ for human wild type TrkB extracellular domain measured on the basis of at least three readings. In another embodiment, a substantial decrease in affinity is where the mean $K_D$ for the mutated version measured on the basis of at least three readings is at least 5 fold greater than the mean $K_D$ for human wild type TrkB extracellular domain measured on the basis of at least three readings. In yet another embodiment, a substantial decrease in affinity is where the mean $K_D$ for the mutated version measured on the basis of at least three readings is at least 10 fold greater than the mean $K_D$ for human wild type TrkB extracellular domain measured on the basis of at least three readings. In one embodiment, altered affinity refers to reduced affinity.

In one embodiment, the invention provides a TrkB binding protein that binds to human TrkB and results in peptides derived from human TrkB containing part or the whole of the sequence from residues 385-398 (numbering according to full length human TrkB) being more resistant to deuterium incorporation compared to corresponding peptides derived from uncomplexed human TrkB. In one embodiment, resistance to deuterium incorporation is assessed at a time point of between 15 and 60 seconds after dilution into deuterated buffer (e.g. at one of 15 or 60 seconds).

In one embodiment, the invention provides a TrkB binding agonist that binds to a peptide having the amino acid sequence set forth in SEQ ID NO: 69 (a peptide within the juxta-membrane region containing all the residues identified by alanine scanning mutagenesis as important for binding to antibody 3A3). In this context, the term "binds to" requires a binding response substantially greater than observed for any non-overlapping peptide of equivalent length derived from human TrkB extracellular domain. Binding may be assessed by any suitable method, for example ELISA. The peptides may be tagged (e.g. biotinylated) to facilitate the binding assay, but the sequence may not be extended by additional amino acids. In one embodiment, the peptide may have the sequence set forth as SEQ ID NO: 70 (a smaller peptide, still containing the residues identified by alanine scanning mutagenesis as important for binding to antibody 3A3). It should be noted that the requirement to bind to a peptide having the sequences specified does not necessarily mean that the binding protein may not interact with residues outside of this sequence or, for example, protect them from e.g. deuterium uptake provided that an "all or nothing" binding response is achieved (i.e. the levels of binding achieved by peptides having the sequence set forth in SEQ ID NO:69 (or 70) being substantially greater than levels achieved by other, non-overlapping TrkB peptides). A substantially greater binding response in the context of this invention refers to the situation where the mean $K_D$ for a peptide containing the sequence set forth in SEQ ID NO: 69 (or 70) on the basis of at least three readings is less than or equal to the mean $K_D$ for the non-overlapping TrkB peptides measured on the basis of at least three readings minus one standard deviation (the largest standard deviation observed for any peptide being used). In one embodiment, the mean $K_D$ for a peptide containing the sequence set forth in SEQ ID NO: 69 (or 70) on the basis of at least three readings is less than or equal to the mean $K_D$ for the non-overlapping TrkB peptides measured on the basis of at least three readings minus two standard deviations (the largest standard deviation observed for any peptide being used). In a further embodiment, the mean $K_D$ for a peptide containing the sequence set forth in SEQ ID NO: 69 (or 70) on the basis of at least three readings is less than or equal to the mean $K_D$ for the non-overlapping TrkB peptides measured on the basis of at least three readings minus three standard deviations (the largest standard deviation observed for any peptide being used). In one embodiment, the mean $K_D$ for a peptide containing the sequence set forth in SEQ ID NO: 69 (or 70) on the basis of at least three readings is at least 3 fold lower than the mean $K_D$ for the non-overlapping TrkB peptides measured on the basis of at least three readings. In another embodiment, the mean $K_D$ for a peptide containing the sequence set forth in SEQ ID NO: 69 (or 70) on the basis of at least three readings is at least 5 fold lower than the mean $K_D$ for the non-overlapping TrkB peptides measured on the basis of at least three readings. In another embodiment, the mean $K_D$ for a peptide containing the sequence set forth in SEQ ID NO: 69 (or 70) on the basis of at least three readings is at least 10 fold lower than the mean $K_D$ for the non-overlapping TrkB peptides measured on the basis of at least three readings.

Although the TrkB JM region epitope appears to be distinct to the TrkB D5 epitope, it is important to note that TrkB binding agonists 1G11, 3A3 and 8E5 can (at least partially) compete with each other for binding to TrkB, and therefore the epitopes may be overlapping. It is possible that the long flexible linker of the juxta-membrane (JM) region may actually be in close proximity to the D5 beta sheets A and G, and the region between beta sheets A and A'. It is possible that when a TrkB binding agonist that binds to the JM region epitope, it has some additional interactions with BDNF (for example via the N-terminus of the ligand), and/or similarly stabilises the ternary complex of receptor plus ligand plus agonist. Interestingly, residues D394, I396, and Y400 in the juxta-membrane region confer human TrkB receptor specificity because these residues are different in rat TrkB (Glu, Leu, Trp respectively). It is possible that other TrkB binding agonists binding the same region but making different contacts may exhibit cross reactivity.

In some embodiments, the TrkB binding agonist epitope on TrkB does not overlap with the BDNF ligand binding domain (LBD). The TrkB binding agonist may bind to an epitope on TrkB that allows for binding of BDNF to TrkB to form a ternary complex (TrkB agonist binding agonist +TrkB+BDNF).

Certain TrkB binding agonist epitopes on TrkB may overlap with the epitope on TrkB to which a reference antibody binds. In one embodiment, the invention provides TrkB binding agonists that compete for binding to TrkB with a reference antibody. In one embodiment, the TrkB binding agonist competes for binding to TrkB with a reference antibody, and does not compete for binding to TrkB with BDNF. The reference antibody may have (a) a heavy chain sequence of SEQ ID NO: 27 and a light chain sequence of SEQ ID NO: 28; or (b) a heavy chain sequence of SEQ ID NO: 29 and a light chain sequence of SEQ ID NO: 30; or (c) a heavy chain sequence of SEQ ID NO: 31 and a light chain sequence of SEQ ID NO: 32.

The TrkB binding agonists may agonise cellular signalling of TrkB to enhance (a) cell survival, (b) neuronal repair, and/or (c) neuronal plasticity. Enhancement is an improved biological function or response in the presence of the agonist compared with the absence of the agonist.

"Cell survival" includes maintaining or promoting growth of cells in which TrkB is expressed. TrkB is expressed in both the central (CNS) and peripheral nervous systems (PNS). In CNS, high levels of TrkB are expressed in cerebral cortex, hippocampus, thalamus, choroid plexus, and granular layer of the cerebellum, brain stem, retina and spinal cord. In PNS, TrkB is expressed in cranial ganglia, vestibular system, sub-maxillary glands and the dorsal root ganglia. TrkB is widely expressed in the fetal brain. TrkB is also expressed in other tissues such as skeletal muscle, kidney and pancreas. TrkB is also expressed in Meissner corpuscles. Activating TrkB in central nervous system (CNS) and at the neuromuscular interface in skeletal muscles may regulate cerebral and spinal cord motor neuron survival and progenitor muscle cell differentiation. In one example, cell survival includes neuronal cell survival.

For example, TrkB binding agonists of the invention may promote the neuronal survival, for example survival of rat PC12 neuroblastoma cell line stably expressing human full length TrkB receptor. The TrkB binding agonists 1G11, humanised 1G11, 8E5 and 3A3 can promote the survival of cells (in a rat PC12 neuroblastoma cell line stably expressing human full length TrkB receptor) in a concentration-dependent manner with an average $EC_{50}$ of 0.006-0.025 nM.

The TrkB binding agonist may activate endogenously expressed TrkB receptors in rat brain and/or spinal cord derived neurons, mouse brain derived neurons, and/or recombinantly expressed cynomolgus TrkB in CHO cells.

TrkB can regulate neuronal repair, including axon regeneration and growth, neurite outgrowth, the rate and extent of nerve myelination, and muscle regeneration. Repair may be physiological to maintain homeostasis (i.e. maintaining balance in response to biological inputs), or as a result of injury and/or damage. For example, TrkB binding agonist may induce neurite outgrowth, for example neurite outgrowth in the rat PC12 neuroblastoma cell line stably expressing human full length TrkB receptor. The TrkB binding agonists 1G11, humanised 1G11 and 8E5 induced neurite outgrowth (in a rat PC12 neuroblastoma cell line stably expressing human full length TrkB receptor) in a concentration-dependent manner with an average $EC_{50}$ of 0.07-1.58 nM.

TrkB can regulate neuronal plasticity (neuroplasticity), encompassing both synaptic plasticity and non-synaptic plasticity. Neuronal plasticity refers to changes in neural pathways and synapses due to changes in behaviour, environment, neural processes, thinking, emotions, and changes resulting from injury and/or damage. For example, TrkB can regulate synaptic plasticity functions. Activating TrkB in the central nervous system (CNS) and at the neuromuscular interface in skeletal muscles may stabilise the neuromuscular junction (NMJ), and regulate acetyl choline (ACh) transmission at NMJ.

The TrkB binding agonist may be a peptide, polypeptide, protein, RNA aptamer, or a polysaccharide. For example the TrkB binding agonist is an antigen binding protein. The term "antigen binding protein" as used herein refers to an antibody, and alternative antibody formats which are capable of binding to TrkB.

The term "antibody" is used herein in the broadest sense to refer to molecules with an immunoglobulin-like domain (for example IgG, IgM, IgA, IgD or IgE) and includes monoclonal, recombinant, synthetic, polyclonal, chimeric, human, humanised, multispecific antibodies, including bispecific antibodies, and heteroconjugate antibodies; a single variable domain, antigen binding antibody fragments (e.g. Fab, F(ab')2, Fv, disulphide linked Fv, single chain Fv, disulphide-linked scFv, diabodies, TANDAB™, etc.) and modified versions of any of the foregoing. In one embodiment, the antibody has an IgG, or IgA scaffold. In one embodiment, the antibody has an IgG scaffold, which may be a four chain or two chain antibody. The IgG scaffold may comprise some or all the domains of an antibody (i.e. CH1, CH2, CH3, VH, VL). The antigen binding protein may comprise an IgG scaffold selected from IgG1, IgG2, IgG3, IgG4 or IgG4PE. For example, the scaffold may be IgG1. The scaffold may consist of, or comprise, the Fc region of an antibody, or a part thereof. The TrkB binding agonist may comprise a Fc region that is disabled. For example, the Fc region may be modified with mutations L235A and G237A (EU numbering). This modification of the Fc region diminishes antibody binding to Fcγ receptors and C1q, therefore reducing the potential of the antibody to induce depletion of TrkB positive cells by antibody-dependent cytotoxicity (ADCC) or complement dependent cytotoxicity (CDC). This is commonly described as Fc-disablement. It should be noted that Fc effector function is not critical to the biological function of the TrkB binding agonist.

The term "domain" refers to a folded protein structure which retains its tertiary structure independent of the rest of the protein. Generally domains are responsible for discrete functional properties of proteins and in many cases may be added, removed or transferred to other proteins without loss of function of the remainder of the protein and/or of the domain. The term "single variable domain" refers to a folded polypeptide domain comprising sequences characteristic of antibody variable domains. It therefore includes complete antibody variable domains such as VH, VHH and VL and modified antibody variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain. A single variable domain that is capable of binding an antigen or epitope independently of a different variable region or domain may be referred to as a "domain antibody" or "dAb(™)". A single variable domain may be a human single variable domain, but also includes single variable domains from other species such as rodent, nurse shark and Camelid VHH dAbs™. Camelid VHH are immunoglobulin single variable domain polypeptides that are derived from species including camel, llama, alpaca, dromedary, and guanaco, which produce heavy chain antibodies naturally devoid of light chains. Such VHH domains may be humanised according to standard techniques available in the art, and such domains are considered to be "single variable domains". As used herein VH includes camelid VHH domains.

Alternative antibody formats are those where the CDRs of the TrkB binding agonist are arranged onto a suitable non-immunoglobulin protein scaffold or skeleton. The non-immunoglobulin scaffold may be a derived from the group consisting of CTLA-4, lipocalin, Protein A derived molecules such as Z-domain of Protein A (Affibody, SpA), A-domain (Avimer/Maxibody); heat shock proteins such as GroEl and GroES; transferrin (trans-body); ankyrin repeat protein (DARPin); peptide aptamer; C-type lectin domain (Tetranectin); human γ-crystallin and human ubiquitin (affilins); PDZ domains; LDL receptor class A domains; EGF domains; scorpion toxin kunitz type domains of human protease inhibitors; and fibronectin/adnectin.

The HC and LC domains of the 1G11 TrkB binding agonist are set out in SEQ ID NO: 27 and SEQ ID NO: 28 respectively. The VH and VL domains of the humanised 1G11 TrkB binding agonist are set out in SEQ ID NO: 40 and SEQ ID NO: 41 respectively.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin.

The CDR regions for SEQ ID NO.27, SEQ ID NO. 28, SEQ ID NO: 40 and SEQ ID NO 41 can be defined by any numbering convention, for example the Kabat, Chothia, AbM and contact conventions. The CDR regions for SEQ ID NO.27, SEQ ID NO. 28, SEQ ID NO: 40 and SEQ ID NO 41 defined by each method are set out in Table 1. It is noted that with the exception of CDRH2 defined by the Contact method, the CDR sequences of the mouse 1G11 and humanised 1G11 are identical. Throughout this specification, amino acid residues are numbered according to the Kabat numbering convention.

TABLE 1

| Sequence of CDR | Kabat | Chothia | AbM | Contact |
|---|---|---|---|---|
| CDRH1 from SEQ ID NOs: 27 and 40 | SYYIN (SEQ ID NO: 6) | GYTFTSY (SEQ ID NO: 58) | GYTFTSYY IN (SEQ ID NO: 60) | TSYYIN (SEQ ID NO: 62) |
| CDRH2 from SEQ ID NO: 27 | RIAPGNTY YNEIFKG (SEQ ID NO: 7) | APGN (SEQ ID NO: 59) | RIAPGNTY (SEQ ID NO: 61) | CIGRIAP GNTY (SEQ ID NO: 63) |
| CDRH2 from SEQ ID NO: 40 | RIAPGNTY YNEIFKG (SEQ ID NO: 7) | APGN (SEQ ID NO: 59) | RIAPGNTY (SEQ ID NO: 61) | SMGRIAP GNTY (SEQ ID NO: 64) |
| CDRH3 from SEQ ID Nos: 27 and 40 | RGYEGALDY (SEQ ID NO: 8) | RGYEGALDY (SEQ ID NO: 8) | RGYEGALDY (SEQ ID NO: 8) | ARRGYEG ALD (SEQ ID NO: 65) |
| CDRL1 from SEQ ID NOs: 28 and 41 | RASQRIS NNLH (SEQ ID NO: 3) | RASQRISNNLH (SEQ ID NO: 3) | RASQRISNN LH (SEQ ID NO: 3) | SNNLHWY (SEQ ID NO: 66) |
| CDRL2 from SEQ ID NOs: 28 and 41 | YVSQSIS (SEQ ID NO: 4) | YVSQSIS (SEQ ID NO: 4) | YVSQSIS (SEQ ID NO: 4) | LLIKYVSQ-SI (SEQ ID NO: 67) |
| CDRL3 from SEQ ID NOs: 28 and 41 | QQSNSWPLT (SEQ ID NO: 5) | QQSNSWPLT (SEQ ID NO: 5) | QQSNSWPLT (SEQ ID NO: 5) | QQSNSWPL (SEQ ID NO: 68) |

The main binding residues in the 1G11 TrkB binding agonist paratope and presumably the humanised 1G11 TrkB binding agonist paratope are within CDRs L1 (bold residues represent those approaching the epitope within 4.5 Å, underlined residues represent those that interact directly or indirectly (via water) with the epitope: RAS<u>QRIS</u>NNLH/SEQ ID NO:3), L3 (bold residues represent those approaching the epitope within 4.5 Å, underlined residues represent those that interact directly or indirectly (via water) with the epitope: QQS<u>NSW</u>PLT/SEQ ID NO:5) and H3 (bold residues represent those approaching the epitope within 4.5 Å, underlined residues represent those that interact directly or indirectly (via water) with the epitope: R<u>GYEGALDY</u>/SEQ ID NO:8). There are only two residues in CDRH2 approaching the epitope within 4.5 Å and only one direct interaction (bold residues represent those approaching the epitope within 4.5 Å, underlined residues represent those that interact directly or indirectly (via water) with the epitope: <u>RI</u>APGNTYYNEIFKG/SEQ ID NO:7). There is only and a single residue in CDRH1 that approaches or (indirectly) contacts the epitope (bold residues represent those approaching the epitope within 4.5 Å, underlined residues represent those that interact directly or indirectly (via water) with the epitope: <u>S</u>YYIN/SEQ ID NO:6) and a single residue in CDRL2 that approaches the epitope (bold residues represent those approaching the epitope within 4.5 Å, underlined residues represent those that interact directly or indirectly (via water) with the epitope: YVSQSIS/SEQ ID NO:4). Therefore, from a ranking point of view, CDRs L1, L3 and H3 are most important for binding, followed by CDRH2, then CDRL2 and CDRH1.

In one embodiment, the TrkB binding agonist comprises: (a) CDRL1 as present in SEQ ID NO: 28 or a variant thereof, which variant has 1, 2 or 3 amino acid modifications; (b) CDRL3 as present in SEQ ID NO: 28 or a variant thereof, which variant has 1, 2 or 3 amino acid modifications; and (c) CDRH3 as present in SEQ ID NO: 27 or a variant thereof, which variant has 1, 2 or 3 amino acid modifications.

In one embodiment, CDRL1 is as present in SEQ ID NO: 3 or SEQ ID NO: 66, or a variant of SEQ ID NO: 3 or SEQ ID NO: 66, which variant has 1, 2 or 3 amino acid modifications. In a further embodiment, CDRL1 is as present in SEQ ID NO: 3 or a variant thereof, which variant has 1, 2 or 3 amino acid modifications. In one embodiment, the modifications within CDRL1 are not in residues R28, S30 and N32 (numbering from SEQ ID NO: 28). In certain embodiments, in addition to not modifying R28, S30 and N32, the modifications within CDRL1 are not in residue I29 and/or in residue N31 (numbering from SEQ ID NO: 28). In one embodiment, CDRL1 is as present in SEQ ID NO: 3 or SEQ ID NO: 66. In one embodiment, CDRL1 is as present in SEQ ID NO: 3.

In one embodiment, CDRL3 is as present in SEQ ID NO: 5 or SEQ ID NO: 68, or a variant of SEQ ID NO: 5 or SEQ ID NO: 68, which variant has 1, 2 or 3 amino acid modifications. In a further embodiment, CDRL3 is as present in SEQ ID NO: 5 or a variant thereof, which variant has 1, 2 or 3 amino acid modifications. In one embodiment, the modifications within CDRL3 are not in residues N92 and S93 (numbering from SEQ ID NO: 28). In certain embodiments, in addition to not modifying N92 and S93, the modifications within CDRL3 are not in residues S91 and W94 (numbering from SEQ ID NO: 28). In one embodiment, CDRL3 is as present in SEQ ID NO: 5 or SEQ ID NO: 68. In one embodiment, CDRL3 is as present in SEQ ID NO: 5.

In one embodiment, CDRH3 is as present in SEQ ID NO: 8 or SEQ ID NO: 65, or a variant of SEQ ID NO: 8 or SEQ ID NO: 65, which variant has 1, 2 or 3 amino acid modifications. In a further embodiment, CDRH3 is as present in SEQ ID NO: 8 or a variant thereof, which variant has 1, 2 or 3 amino acid modifications. In one embodiment, the modifications in CDRH3 are not in residues R97, Y99 and E100 (numbering from SEQ ID NO: 27). In one embodiment, CDRH3 is as present in SEQ ID NO: 8 or SEQ ID NO: 65. In one embodiment, CDRH3 is as present in SEQ ID NO: 8, In one embodiment, in addition to comprising CDRL1, CDRL3 and CDRH3 as defined above, the TrkB binding agonist additionally comprises CDRH2 as present in SEQ ID NO: 27 or a variant thereof, or SEQ ID NO: 40 or a variant thereof, wherein variants have 1, 2 or 3 amino acid modifications. In one embodiment, CDRH2 is as present in SEQ ID NO: 7, SEQ ID NO: 59, SEQ ID NO: 61, SEQ ID NO: 63 or SEQ ID NO: 64, or a variant of SEQ ID NO: 7, SEQ ID NO: 59, SEQ ID NO: 61, SEQ ID NO: 63 or SEQ ID NO: 64, which variant has 1, 2 or 3 amino acid modifications. In a further embodiment, CDRH3 is as present in SEQ ID NO: 7 or a variant thereof, which variant has 1, 2 or 3 amino acid modifications. In one embodiment, the modifications within CDRH2 are not in residue R50 and/or residue Y57 (numbering from SEQ ID NO: 27). In one embodiment, CDRH2 is as present in SEQ ID NO: 7, SEQ ID NO: 59, SEQ ID NO: 61, SEQ ID NO: 63 or SEQ ID NO: 64. In one embodiment, CDRH2 is as present in SEQ ID NO: 7.

The TrkB binding agonist may comprise CDRL1 (SEQ ID NO:3), CDRL3 (SEQ ID NO:5), and CDRH3 (SEQ ID NO:8). The TrkB binding agonist may comprise CDRL1 (SEQ ID NO:3), CDRL3 (SEQ ID NO:5), CDRH2 (SEQ ID NO:7) and CDRH3 (SEQ ID NO:8).

In one embodiment, in addition to comprising CDRL1, CDRL3, CDRH3 and CDRH2 as defined above, the TrkB binding agonist additionally comprises CDRL2 as present in SEQ ID NO: 28 or a variant thereof, and CDRH1 as present in SEQ ID NO: 27 or a variant thereof, wherein variants have 1, 2 or 3 amino acid modifications.

In one embodiment, CDRL2 is as present in SEQ ID NO: 4 or SEQ ID NO: 67, or a variant of SEQ ID NO: 4 or SEQ ID NO: 67, which variant has 1, 2 or 3 amino acid modifications. In a further embodiment, CDRL2 is as present in SEQ ID NO: 4 or a variant thereof, which variant has 1, 2 or 3 amino acid modifications. In one embodiment, the modifications within CDRL2 are not in residue Y50 (numbering from SEQ ID NO: 28). In one embodiment, CDRL2 is as present in SEQ ID NO: 4 or SEQ ID NO: 67. In one embodiment, CDRL2 is as present in SEQ ID NO: 4.

In one embodiment, CDRH1 is as present in SEQ ID NO: 6, SEQ ID NO: 58, SEQ ID NO: 60 or SEQ ID NO: 62, or a variant of SEQ ID NO: 6, SEQ ID NO: 58, SEQ ID NO: 60 or SEQ ID NO: 62, which variant has 1, 2 or 3 amino acid modifications. In a further embodiment, CDRH1 is as present in SEQ ID NO: 6 or a variant thereof, which variant has 1, 2 or 3 amino acid modifications. In one embodiment, the modifications within CDRH1 are not in residue Y33 (numbering from SEQ ID NO: 27). In certain embodiments, in addition to not modifying Y33, the modifications within CDRH1 are not in residue S31 (numbering from SEQ ID NO: 27). In one embodiment, CDRH1 is as present in SEQ ID NO: 6, SEQ ID NO: 58, SEQ ID NO: 60 or SEQ ID NO: 62. In one embodiment, CDRH1 is as present in SEQ ID NO: 6.

The TrkB binding agonist may comprise CDRH1 of SEQ ID NO: 6; CDRH2 of SEQ ID NO: 7; CDRH3 of SEQ ID NO: 8; CDRL1 of SEQ ID NO: 3; CDRL2 of SEQ ID NO: 4; and CDRL3 of SEQ ID NO: 5.

In the foregoing embodiments, certain CDRs may be a variant sequences with up to 3 amino acid modifications. Each modification may be independently a substitution, addition or deletion. For example, a variant sequence may have one addition, one deletion and one substitution. In one embodiment, each variant sequence has 1 amino acid modification. In another embodiment, each variant sequence has up to 2 amino acid modifications. In one embodiment, the modification is a substitution, particularly a conservative substitution, for example as shown in Table 2.

TABLE 2

| Side chain | Members |
|---|---|
| Hydrophobic | Met, Ala, Val, Leu, Ile |
| Neutral hydrophilic | Cys, Ser, Thr |
| Acidic | Asp, Glu |
| Basic | Asn, Gln, His, Lys, Arg |
| Residues that influence chain orientation | Gly, Pro |
| Aromatic | Trp, Tyr, Phe |

The CDRs L1, L2, L3, H1 and H2 tend to structurally exhibit one of a finite number of main chain conformations. The particular canonical structure class of a CDR is defined by both the length of the CDR and by the loop packing, determined by residues located at key positions in both the CDRs and the framework regions (structurally determining residues or SDRs). Cluster analysis is used to define the canonical classes for sets of CDRs, and canonical templates are then identified by analysing buried hydrophobics, hydrogen-bonding residues, and conserved glycines and prolines. The CDRs of antibody sequences can be assigned to canonical classes by comparing the sequences to the key residue templates and scoring each template using identity or similarity matrices.

There may be multiple variant CDR canonical positions per CDR, per variable region, per heavy or light chain, and therefore any combination of substitution may be present in the TrkB binding agonist, provided that the canonical structure of the CDR is maintained such that the agonist is capable of binding TrkB.

The TrkB binding agonist CDR variant may comprise:
(a) a variant of CDRH1 having any one or a combination of: Y32 substituted by I, H, F, T, N, C, E, or D; I34 substituted by V, M or W; and N35 substituted by H, E, Q, S, Y or T; and/or
(b) a variant of CDRH2 having I51 substituted by L, V, T, S or N; and/or
(c) a variant of CDRH3 having Y102 substituted by H, V, I, S, D or G; and/or
(d) a variant of CDRL1 having any one or a combination of: L33 substituted by M, V, I or F; and H34 substituted by A, G, N, S, V or F; and/or
(e) a variant of CDRL2 having V51 substituted by A, T or G; and/or
(f) a variant of CDRL3 having any one or a combination of: Q89 substituted by S, G, F or L; Q90 substituted by H or N; L96 substituted by P, Y, R, I, W or F.

The TrkB binding agonist may comprise: a humanised VH region, or a humanised Heavy Chain (HC) sequence; and/or a humanised VL region, or a humanised Light Chain (LC) sequence.

The TrkB binding agonist may comprise: a VH region as set forth in SEQ ID NO: 40 or a variant thereof, which variant has up to 10 amino acid modifications; and/or a VL region as set forth in SEQ ID NO: 41 or a variant thereof, which variant has up to 10 amino acid modifications. The TrkB binding agonist may comprise: a VH region as set forth in SEQ ID NO: 40 or a variant thereof, which variant has up to 10 amino acid modifications; and a VL region as set forth in SEQ ID NO: 41 or a variant thereof, which variant has up to 10 amino acid modifications. In one embodiment, the variant VH region has 1, 2 3, 4, 5, 6, 7, 8, 9 or 10 amino acid modifications. In one embodiment, the variant VL region has 1, 2 3, 4, 5, 6, 7, 8, 9 or 10 amino acid modifications.

The TrkB binding agonist may comprise: a HC as set forth in SEQ ID NO: 42 or a variant thereof, which variant has up to 10 amino acid modifications; and/or a LC region as set forth in SEQ ID NO: 43 or a variant thereof, which variant has up to 10 amino acid modifications. The TrkB binding agonist may comprise: a HC as set forth in SEQ ID NO: 42 or a variant thereof, which variant has up to 10 amino acid modifications; and a LC region as set forth in SEQ ID NO: 43 or a variant thereof, which variant has up to 10 amino acid modifications. In one embodiment, the variant HC has 1, 2 3, 4, 5, 6, 7, 8, 9 or 10 amino acid modifications. In one embodiment, the variant LC has 1, 2 3, 4, 5, 6, 7, 8, 9 or 10 amino acid modifications.

The modifications to the VH, VL, HC and LC may be independently a substitution, addition or deletion such that any particular variant sequence may contain substitutions, additions and deletions. Typically, the variation is a substitution, particularly a conservative substitution, for example as shown in Table 2 above.

In certain embodiments, the modification(s) to the VH, VL, HC and LC may exclude the CDRs such that the CDRs are intact and the variation is in the remaining portion of the VH, VL, HC or LC sequence. The variant sequence substantially retains the biological characteristics of the unmodified TrkB binding agonist.

The TrkB binding agonist may comprise a VH region comprising a sequence at least 80% identical to the sequence of SEQ ID NO: 40 and/or a VL region comprising a sequence at least 76% identical to the sequence of SEQ ID NO: 41. In one embodiment, the VH region comprises a sequence at least 85% identical, at least 90% identical, at least 95% identical, at least 97% identical, at least 98% identical, or at least 99% identical to the sequence of SEQ ID NO: 40. In one embodiment, the VL region comprises a sequence at least 80% identical, at least 85% identical, at least 90% identical, at least 95% identical, at least 97% identical, at least 98% identical, or at least 99% identical to the sequence of SEQ ID NO: 41.

The TrkB binding agonist may comprise VH region wherein position 47 is Cys or Ser. The TrkB binding agonist may comprise VH region wherein position 47 is Cys, Ser, Gly, Ala, Val, Thr or Asn.

"Percent identity" between a query sequence and a subject sequence can be calculated using the "Identities" value, expressed as a percentage, that is calculated by the BLASTP algorithm when a subject amino acid sequence has 100% query coverage with a query amino acid sequence after a pair-wise BLASTP alignment is performed. Such pair-wise BLASTP alignments between a query amino acid sequence and a subject amino acid sequence can be performed by using the default settings of the BLASTP algorithm available on the National Center for Biotechnology Institute's website with the filter for low complexity regions turned off.

The query sequence may be 100% identical to the subject sequence, or it may include up to a certain integer number of amino acid or nucleotide alterations as compared to the subject sequence such that the % identity is less than 100% as set forth above. Such alterations include at least one amino acid deletion, substitution (including conservative and non-conservative substitution), or insertion, and wherein said alterations may occur at the amino- or carboxy-terminal positions of the query sequence or anywhere between those terminal positions, interspersed either individually among the amino acids or nucleotides in the query sequence or in one or more contiguous groups within the query sequence.

The % identity may be determined across the entire length of the query sequence, including the CDRs. Alternatively, the % identity may exclude the CDRs, for example the CDRs are 100% identical to the subject sequence and the % identity variation is in the remaining portion of the query sequence (i.e. SEQ ID NO: 40 or SEQ ID NO: 41), so that the CDR sequence is fixed/intact. Alternatively, the CDR sequences are as set forth in any of the foregoing embodiments and % identity variation is calculated over the remaining portion of the query sequence. The variant sequence substantially retains the biological characteristics of the unmodified TrkB binding agonist.

The present invention also provides a TrkB binding agonist comprising: (a) a VH region of SEQ ID NO: 40; and/or (b) a VL region of SEQ ID NO: 41. In one embodiment, the invention provides a TrkB binding agonist comprising: (a) a VH region of SEQ ID NO: 40; and (b) a VL region of SEQ ID NO: 41.

The present invention also provides a TrkB binding agonist comprising: (a) a Heavy Chain (HC) sequence at least 90% identical to SEQ ID NO: 42; and/or (b) a Light Chain (LC) sequence at least 85% identical to SEQ ID NO: 43. In one embodiment, the HC comprises a sequence at least 95% identical, at least 97% identical, at least 98% identical, or at least 99% identical to the sequence of SEQ ID NO: 42. In one embodiment, the LC comprises a sequence at least 90% identical, at least 95% identical, at least 97% identical, at least 98% identical, or at least 99% identical to the sequence of SEQ ID NO: 42.

The TrkB binding agonist may comprise HC region wherein position 47 is Cys or Ser. The TrkB binding agonist may comprise HC region wherein position 47 is Cys, Ser, Gly, Ala, Val, Thr or Asn.

"Percent identity" is calculated as set out above. Again, the % identity may be determined across the entire length of the query sequence, including the CDRs. Alternatively, the % identity may exclude the CDRs, for example the CDRs are 100% identical to the subject sequence and the % identity variation is in the remaining portion of the query sequence (i.e. SEQ ID NO: 40 or SEQ ID NO: 41), so that the CDR sequence is fixed/intact. Alternatively, the CDR sequences are as set forth in any of the foregoing embodiments and % identity variation is calculated over the remaining portion of the query sequence. The variant sequence substantially retains the biological characteristics of the unmodified TrkB binding agonist.

The present invention also provides a TrkB binding agonist comprising: (a) a Heavy Chain (HC) sequence of SEQ ID NO: 42; and/or (b) a Light Chain (LC) sequence of SEQ ID NO: 43. In one embodiment, the invention provides a TrkB binding agonist comprising: (a) a Heavy Chain (HC) sequence of SEQ ID NO: 42; and (b) a Light Chain (LC) sequence of SEQ ID NO: 43.

The HC and LC domains of the 3A3 TrkB binding agonist are set out in SEQ ID NO: 29 and SEQ ID NO: 30 respectively. The VH and VL domains of the humanised 3A3 TrkB binding agonist are set out in SEQ ID NO: 46 and SEQ ID NO: 47 respectively.

The TrkB binding agonist may comprise any one or a combination of CDRs selected from CDRH1, CDRH2, CDRH3 from SEQ ID NO: 29, and/or CDRL1, CDRL2, CDRL3 from SEQ ID NO:30; or a CDR variant, wherein the variant has 1, 2, or 3 amino acid modifications in each CDR. For example, the TrkB binding agonist may comprise 1, 2, 3, 4, 5, or 6 CDRs selected from CDRH1, CDRH2, CDRH3 from SEQ ID NO: 29, and/or CDRL1, CDRL2, CDRL3 from SEQ ID NO:30; or a CDR variant, wherein the variant has 1, 2, or 3 amino acid modifications in each CDR. In certain embodiments, particular CDRs are as present in SEQ ID NO: 29 or SEQ ID NO: 30 whilst other CDRs are variants of those present in SEQ ID NO: 29 or SEQ ID NO: 30. In one embodiment, the invention provides a TrkB binding agonist comprising one of more of the following CDRs:
(a) CDRL1 as present in SEQ ID NO: 30 or a variant thereof, which variant has 1, 2 or 3 amino acid modifications;
(b) CDRL2 as present in SEQ ID NO: 30 or a variant thereof, which variant has 1, 2 or 3 amino acid modifications;
(c) CDRL3 as present in SEQ ID NO: 30 or a variant thereof, which variant has 1, 2 or 3 amino acid modifications;
(d) CDRH1 as present in SEQ ID NO: 29 or a variant thereof, which variant has 1, 2 or 3 amino acid modifications;
(e) CDRH2 as present in SEQ ID NO: 29 or a variant thereof, which variant has 1, 2 or 3 amino acid modifications; and
(f) CDRH3 as present in SEQ ID NO: 29 or a variant thereof, which variant has 1, 2 or 3 amino acid modifications.

In one embodiment, the TrkB binding agonist comprises at least two CDRs, at least three CDRs, at least four CDRs or at least five CDRs or all six CDRs selected from the group:
(a) CDRL1 as present in SEQ ID NO: 30 or a variant thereof, which variant has 1, 2 or 3 amino acid modifications;
(b) CDRL2 as present in SEQ ID NO: 30 or a variant thereof, which variant has 1, 2 or 3 amino acid modifications;
(c) CDRL3 as present in SEQ ID NO: 30 or a variant thereof, which variant has 1, 2 or 3 amino acid modifications;
(d) CDRH1 as present in SEQ ID NO: 29 or a variant thereof, which variant has 1, 2 or 3 amino acid modifications;
(e) CDRH2 as present in SEQ ID NO: 29 or a variant thereof, which variant has 1, 2 or 3 amino acid modifications; and
(f) CDRH3 as present in SEQ ID NO: 29 or a variant thereof, which variant has 1, 2 or 3 amino acid modifications.

In embodiments relating to 3A3, certain CDRs may be a variant sequences with up to 3 amino acid modifications. Each modification may be independently a substitution, addition or deletion. For example, a variant sequence may have one addition, one deletion and one substitution. In one embodiment, each variant CDR may have 1 amino acid modification. In another embodiment, each variant sequence has up to 2 amino acid modifications. In one embodiment, the modification is a substitution, particularly a conservative substitution, for example as shown in Table 2 above.

The TrkB binding agonist may comprise any one or a combination of the following CDRs: CDRH1 of SEQ ID NO: 12; CDRH2 of SEQ ID NO: 13; CDRH3 of SEQ ID NO: 14; CDRL1 of SEQ ID NO: 9; CDRL2 of SEQ ID NO: 10; and/or CDRL3 of SEQ ID NO: 11. For example, the TrkB binding agonist may comprise 1, 2, 3, 4, 5, or 6 CDRs selected from CDRH1 of SEQ ID NO: 12; CDRH2 of SEQ ID NO: 13; CDRH3 of SEQ ID NO: 14; CDRL1 of SEQ ID NO: 9; CDRL2 of SEQ ID NO: 10; and/or CDRL3 of SEQ ID NO: 11. The TrkB binding agonist may comprise CDRH1 of SEQ ID NO: 12; CDRH2 of SEQ ID NO: 13; CDRH3 of SEQ ID NO: 14; CDRL1 of SEQ ID NO: 9; CDRL2 of SEQ ID NO: 10; and CDRL3 of SEQ ID NO: 11.

The TrkB binding agonist may comprise: a humanised VH region, or a humanised Heavy Chain (HC) sequence; and/or a humanised VL region, or a humanised Light Chain (LC) sequence.

The TrkB binding agonist may comprise: a VH region as set forth in SEQ ID NO: 40 or a variant thereof, which variant has up to 10 amino acid modifications; and/or a VL region as set forth in SEQ ID NO: 41 or a variant thereof, which variant has up to 10 amino acid modifications. The TrkB binding agonist may comprise: a VH region as set forth in SEQ ID NO: 40 or a variant thereof, which variant has up to 10 amino acid modifications; and a VL region as set forth in SEQ ID NO: 41 or a variant thereof, which variant has up to 10 amino acid modifications. In one embodiment, the variant VH region has 1, 2 3, 4, 5, 6, 7, 8, 9 or 10 amino acid modifications. In one embodiment, the variant VL region has 1, 2 3, 4, 5, 6, 7, 8, 9 or 10 amino acid modifications.

The TrkB binding agonist may comprise: a HC as set forth in SEQ ID NO: 42 or a variant thereof, which variant has up to 10 amino acid modifications; and/or a LC region as set forth in SEQ ID NO: 43 or a variant thereof, which variant has up to 10 amino acid modifications. The TrkB binding agonist may comprise: a HC as set forth in SEQ ID NO: 42 or a variant thereof, which variant has up to 10 amino acid modifications; and a LC region as set forth in SEQ ID NO:

43 or a variant thereof, which variant has up to 10 amino acid modifications. In one embodiment, the variant HC has 1, 2 3, 4, 5, 6, 7, 8, 9 or 10 amino acid modifications. In one embodiment, the variant LC has 1, 2 3, 4, 5, 6, 7, 8, 9 or 10 amino acid modifications.

The modifications to the VH, VL, HC and LC may be independently a substitution, addition or deletion such that any particular variant sequence may contain substitutions, additions and deletions. Typically, the variation is a substitution, particularly a conservative substitution, for example as shown in Table 2 above.

The TrkB binding agonist may comprise a VH region comprising a sequence at least 80% identical to the sequence of SEQ ID NO: 46 and/or a VL region comprising a sequence at least 80% identical to the sequence of SEQ ID NO: 47. In one embodiment, the VH region comprises a sequence at least 85% identical, at least 90% identical, at least 95% identical, at least 97% identical, at least 98% identical, or at least 99% identical to the sequence of SEQ ID NO: 46. In one embodiment, the VL region comprises a sequence at least 85% identical, at least 90% identical, at least 95% identical, at least 97% identical, at least 98% identical, or at least 99% identical to the sequence of SEQ ID NO: 47. The TrkB binding agonist may comprise a VH region of SEQ ID NO: 46; and/or a VL region of SEQ ID NO: 47. The TrkB binding agonist may comprise a VH region of SEQ ID NO: 46; and a VL region of SEQ ID NO: 47.

The TrkB binding agonist may comprise: a Heavy Chain (HC) sequence at least 80% identical to SEQ ID NO: 48; and/or a Light Chain (LC) sequence at least 80% identical to SEQ ID NO: 49. In one embodiment, the HC comprises a sequence at least 85%, at least 90%, at least 95% identical, at least 97% identical, at least 98% identical, or at least 99% identical to the sequence of SEQ ID NO: 48. In one embodiment, the LC comprises a sequence at least 85%, at least 90% identical, at least 95% identical, at least 97% identical, at least 98% identical, or at least 99% identical to the sequence of SEQ ID NO: 49. The TrkB binding agonist may comprise a Heavy Chain (HC) sequence of SEQ ID NO: 48; and/or a Light Chain (LC) sequence of SEQ ID NO: 49. The TrkB binding agonist may comprise a Heavy Chain (HC) sequence of SEQ ID NO: 48; and a Light Chain (LC) sequence of SEQ ID NO: 49.

In the embodiments relating to 3A3, "percent identity" is calculated as set out above. Again, the % identity may be determined across the entire length of the query sequence, including the CDRs. Alternatively, the % identity may exclude the CDRs, for example the CDRs are 100% identical to the subject sequence and the % identity variation is in the remaining portion of the query sequence (i.e. SEQ ID NOs: 46, 47, 48 or 49), so that the CDR sequence is fixed/intact. Alternatively, the CDR sequences are as set forth in any of the foregoing embodiments relating to 3A3 and % identity variation is calculated over the remaining portion of the query sequence. The variant sequence substantially retains the biological characteristics of the unmodified TrkB binding agonist.

The HC and LC domains of the 8E5 TrkB binding agonist are set out in SEQ ID NO: 31 and SEQ ID NO: 32 respectively.

The TrkB binding agonist may comprise any one or a combination of CDRs selected from CDRH1, CDRH2, CDRH3 from SEQ ID NO: 31, and/or CDRL1, CDRL2, CDRL3 from SEQ ID NO:32; or a CDR variant, wherein the variant has 1, 2, or 3 amino acid modifications in each CDR. For example, the TrkB binding agonist may comprise 1, 2, 3, 4, 5, or 6 CDRs selected from CDRH1, CDRH2, CDRH3 from SEQ ID NO: 31, and/or CDRL1, CDRL2, CDRL3 from SEQ ID NO:32; or a CDR variant, wherein the variant has 1, 2, or 3 amino acid modifications in each CDR. In certain embodiments, particular CDRs are as present in SEQ ID NO: 31 or SEQ ID NO: 32 whilst other CDRs are variants of those present in SEQ ID NO: 31 or SEQ ID NO: 32. In one embodiment, the invention provides a TrkB binding agonist comprising one of more of the following CDRs:

(a) CDRL1 as present in SEQ ID NO: 32 or a variant thereof, which variant has 1, 2 or 3 amino acid modifications;
(b) CDRL2 as present in SEQ ID NO: 32 or a variant thereof, which variant has 1, 2 or 3 amino acid modifications;
(c) CDRL3 as present in SEQ ID NO: 32 or a variant thereof, which variant has 1, 2 or 3 amino acid modifications;
(d) CDRH1 as present in SEQ ID NO: 31 or a variant thereof, which variant has 1, 2 or 3 amino acid modifications;
(e) CDRH2 as present in SEQ ID NO: 31 or a variant thereof, which variant has 1, 2 or 3 amino acid modifications; and
(f) CDRH3 as present in SEQ ID NO: 31 or a variant thereof, which variant has 1, 2 or 3 amino acid modifications.

In one embodiment, the TrkB binding agonist comprises at least two CDRs, at least three CDRs, at least four CDRs or at least five CDRs or all six CDRs selected from the group:

(a) CDRL1 as present in SEQ ID NO: 32 or a variant thereof, which variant has 1, 2 or 3 amino acid modifications;
(b) CDRL2 as present in SEQ ID NO: 32 or a variant thereof, which variant has 1, 2 or 3 amino acid modifications;
(c) CDRL3 as present in SEQ ID NO: 32 or a variant thereof, which variant has 1, 2 or 3 amino acid modifications;
(d) CDRH1 as present in SEQ ID NO: 31 or a variant thereof, which variant has 1, 2 or 3 amino acid modifications;
(e) CDRH2 as present in SEQ ID NO: 31 or a variant thereof, which variant has 1, 2 or 3 amino acid modifications; and
(f) CDRH3 as present in SEQ ID NO: 31 or a variant thereof, which variant has 1, 2 or 3 amino acid modifications.

In embodiments relating to 8E5, certain CDRs may be a variant sequences with up to 3 amino acid modifications. Each modification may be independently a substitution, addition or deletion. For example, a variant sequence may have one addition, one deletion and one substitution. In one embodiment, each variant CDR may have 1 amino acid modification. In another embodiment, each variant sequence has up to 2 amino acid modifications. In one embodiment, the modification is a substitution, particularly a conservative substitution, for example as shown in Table 2 above.

The TrkB binding agonist may comprise any one or a combination of the following CDRs: CDRH1 of SEQ ID NO: 18; CDRH2 of SEQ ID NO: 19; CDRH3 of SEQ ID NO: 20; CDRL1 of SEQ ID NO: 15; CDRL2 of SEQ ID NO: 16; and/or CDRL3 of SEQ ID NO: 17. For example, the TrkB binding agonist may comprise 1, 2, 3, 4, 5, or 6 CDRs selected from CDRH1 of SEQ ID NO: 18; CDRH2 of SEQ ID NO: 19; CDRH3 of SEQ ID NO: 20; CDRL1 of SEQ ID NO: 15; CDRL2 of SEQ ID NO: 16; and/or CDRL3 of SEQ ID NO: 17. The TrkB binding agonist may comprise CDRH1 of SEQ ID NO: 18; CDRH2 of SEQ ID NO: 19; CDRH3 of SEQ ID NO: 20; CDRL1 of SEQ ID NO: 15; CDRL2 of SEQ ID NO: 16; and CDRL3 of SEQ ID NO: 17.

The TrkB binding agonist may comprise: a humanised VH region, or a humanised Heavy Chain (HC) sequence; and/or a humanised VL region, or a humanised Light Chain (LC) sequence.

The TrkB binding agonist may comprise: a Heavy Chain (HC) sequence at least 80% identical to SEQ ID NO: 31; and/or a Light Chain (LC) sequence at least 80% identical to SEQ ID NO: 32. In one embodiment, the HC comprises a sequence at least 85%, at least 90%, at least 95% identical, at least 97% identical, at least 98% identical, or at least 99% identical to the sequence of SEQ ID NO: 48. In one embodiment, the LC comprises a sequence at least 85%, at least 90% identical, at least 95% identical, at least 97% identical, at least 98% identical, or at least 99% identical to the sequence of SEQ ID NO: 49. The TrkB binding agonist may comprise a Heavy Chain (HC) sequence of SEQ ID NO: 31; and/or a Light Chain (LC) sequence of SEQ ID NO: 32. The TrkB binding agonist may comprise a Heavy Chain (HC) sequence of SEQ ID NO: 31; and a Light Chain (LC) sequence of SEQ ID NO: 32.

In the embodiments relating to 8E5, "percent identity" is calculated as set out above. Again, the % identity may be determined across the entire length of the query sequence, including the CDRs. Alternatively, the % identity may exclude the CDRs, for example the CDRs are 100% identical to the subject sequence and the % identity variation is in the remaining portion of the query sequence (i.e. SEQ ID NOs: 31 and 32), so that the CDR sequence is fixed/intact. Alternatively, the CDR sequences are as set forth in any of the foregoing embodiments relating to 8E5 and % identity variation is calculated over the remaining portion of the query sequence. The variant sequence substantially retains the biological characteristics of the unmodified TrkB binding agonist.

The TrkB binding agonist may be produced by any of a number of conventional techniques. For example, the TrkB binding agonist may purified from cells that naturally express them (e.g., an antibody can be purified from a hybridoma that produces it), or produced by a recombinant expression system. Generally, host cells are transformed with a recombinant expression vector encoding the desired TrkB binding agonist.

One or more nucleic acid sequences encoding the TrkB binding agonist are also described. For embodiments relating to 1G11, a single nucleic acid sequence may comprise SEQ ID NO: 44 encoding the heavy chain; and/or SEQ ID NO: 45 encoding the light chain, or SEQ ID NO: 44. Alternatively, the invention provides a nucleic acid comprising SEQ ID NO: 44 encoding the heavy chain; and/or a separate nucleic acid comprising SEQ ID NO: 45 encoding the light chain. In one embodiment, a single nucleic acid sequence may comprise SEQ ID NO: 50 encoding the heavy chain; and/or SEQ ID NO: 51 encoding the light chain. In an alternative embodiment, the invention provides a nucleic acid comprising SEQ ID NO: 50 encoding the heavy chain; and/or a separate nucleic acid comprising SEQ ID NO: 51 encoding the light chain.

An expression vector comprising the nucleic acid sequence which encodes the TrkB binding agonist is also described. A recombinant host cell comprising the nucleic acid sequence, or the expression vector is also described. The host cell may be an isolated host cell. The host cell is usually not part of a multicellular organism (e.g., plant or animal). The host cell may be a non-human host cell. A wide range of host cells can be employed, including Prokaryotes (including Gram negative or Gram positive bacteria, for example *Escherichia coli*, Bacilli sp., *Pseudomonas* sp., *Corynebacterium* sp.), Eukaryotes including yeast (for example *Saccharomyces cerevisiae*, *Pichia pastoris*), fungi (for example, *Aspergillus* sp.), or higher Eukaryotes including insect cells and cell lines of mammalian origin (for example, CHO, Perc6, HEK293, HeLa, NSO). Suitable host cells include mammalian cells such as CHO (e.g. CHOK1 and CHO-DG44). Appropriate cloning and expression vectors for use with bacterial, fungal, yeast, and mammalian cellular hosts and methods of cloning are known in the art.

A method for the production of the TrkB binding agonist is described, which method comprises culturing the host cell under conditions suitable for expression of the nucleic acid sequence or vector. In one embodiment, the TrkB binding agonist is purified (e.g. by conventional protein purification procedures). A TrkB binding agonist that is produced by this method is also described. The invention thus provides a population of substantially homogeneous TrkB binding agonist, substantially free of contaminating materials.

Upon expression and production of the TrkB binding agonist, post-translational modifications may occur. This may include the cleavage of certain leader sequences, the addition of various sugar moieties in various glycosylation patterns, deamidation (for example at an asparagine or glutamine residue), oxidation (for example at a methionine, tryptophan or free cysteine residue), disulfide bond scrambling, isomerisation (for example at an aspartic acid residue), C-terminal lysine clipping (for example from one or both heavy chains), and N-terminal glutamine cyclisation (for example in the heavy and/or light chain). The TrkB agonists may have have been subjected to, or have undergone, one or more post-translational modifications. The modification may occur in a CDR, the variable framework region, or the constant region. The modification may result in a change in charge of the molecule.

Deamidation is an enzymatic reaction primarily converting asparagine (N) to iso-aspartic acid (iso-aspartate) and aspartic acid (aspartate) (D) at approximately 3:1 ratio. This deamidation reaction is therefore related to isomerization of aspartate (D) to iso-aspartate. The deamidation of asparagine and the isomerisation of aspartate, both involve the intermediate succinimide. To a much lesser degree, deamidation can occur with glutamine residues in a similar manner. Deamidation can occur in a CDR, in a Fab (non-CDR region), or in the Fc region.

Oxidation can occur during production and storage (i.e. in the presence of oxidizing conditions) and results in a covalent modification of a protein, induced either directly by reactive oxygen species or indirectly by reaction with secondary by-products of oxidative stress. Oxidation happens primarily with methionine residues, but may occur at tryptophan and free cysteine residues. Oxidation can occur in a CDR, in a Fab (non-CDR) region, or in the Fc region.

Disulfide bond scrambling can occur during production and basic storage conditions. Under certain circumstances, disulfide bonds can break or form incorrectly, resulting in unpaired cysteine residues (—SH). These free (unpaired) sulfhydryls (—SH) can promote shuffling.

N-terminal glutamine (Q) and glutamate (glutamic acid) (E) in the heavy chain and/or light chain is likely to form pyroglutamate (pGlu) via cyclization. Most pGlu formation happens in the production bioreactor, but it can be formed non-enzymatically, depending on pH and temperature of processing and storage conditions. Cyclization of N-terminal Q or E is commonly observed in natural human antibodies.

C-terminal lysine clipping is an enzymatic reaction catalyzed by carboxypeptidases, and is commonly observed in recombinant and natural human antibodies. Variants of this process include removal of lysine from one or both heavy chains due to cellular enzymes from the recombinant host cell. Administration of the TrkB binding agonist to the human subject/patient is likely to result in the removal of any remaining C-terminal lysines within the human body.

In the present invention, the post-translational modifications and changes in primary amino acid sequence described above, do not typically result in significant changes in antigen binding affinity, biological activity, PK/PD, aggregation, immunogenicity, or binding to the Fc receptor.

The TrkB binding agonist may be incorporated into pharmaceutical compositions for use in the treatment of the human diseases. In one embodiment, the pharmaceutical composition comprises a TrkB binding agonist optionally in combination with one or more pharmaceutically acceptable carriers and/or excipients and/or diluents. An example of a pharmaceutical composition may comprise one or a combination of buffer(s), salt(s), amino acid(s), polyol(s), sugar(s), surfactant(s), detergent(s), antioxidant(s), and/or chelator(s).

Pharmaceutical compositions may be administered as a bolus or intermittently (for example by injection or by use of sustained release formulations) or by continuous infusion. Routes of administration include, but are not limited to, intravenous, intrathecal, intraperitoneal, intradermal, subcutaneous, topical, transtympanic, intracochlear, intraocular, intravitreally, intramuscular and intraportal. Pharmaceutical compositions may be suitable for topical administration (which includes, but is not limited to, epicutaneous, inhaled, intranasal or ocular administration) or enteral administration (which includes, but is not limited to, oral or rectal administration). For example, the composition is suitable for intravenous or intrathecal administration. In another embodiment, the composition is suitable for intravitreal administration.

Pharmaceutical compositions may comprise between 1 mg to 10 g of TrkB binding agonist, for example between 5 mg and 1 g of antigen binding protein. Alternatively, the composition may comprise between 5 mg and 500 mg, for example between 5 mg and 50 mg.

Effective doses and treatment regimes for administering the TrkB binding agonist may be dependent on factors such as the age, weight and health status of the patient and disease to be treated. Pharmaceutical formulations may be immediate release formulations and sustained release formulations. Sustained release formulations are particularly desirable for transtympanic and intracochlea delivery.

The pharmaceutical composition may comprise a kit of parts of the TrkB binding agonist together with other medicaments, optionally with instructions for use. For convenience, the kit may comprise the reagents in predetermined amounts with instructions for use.

The terms "individual", "subject" and "patient" are used herein interchangeably. In one embodiment, the subject is a mammal, such as a primate, for example a cynomolgus, marmoset or monkey. In another embodiment, the subject is a human.

The TrkB binding agonist may also be used in therapy, for example in methods of treatment or prevention. Treatment and encompasses alleviation or reduction or cure of at least one aspect or symptom or biological manifestations of a disorder.

For example, treatment includes: (1) amelioration of one or more of the biological manifestations of the disorder (2) interference with (a) one or more points in the biological cascade that leads to or is responsible for the disorder or (b) one or more of the biological manifestations of the disorder, (3) alleviation of one or more of the symptoms or effects associated with the disorder, (4) slowing the progression of the disorder or one or more of the biological manifestations of the disorder, and/or (5) diminish the likelihood of severity of a disorder or biological manifestations of the disorder.

Prevention includes the prophylactic administration of a drug to diminish the likelihood of the onset of or to delay the onset of a disorder or biological manifestation thereof, for example by interference with one or more points in the biological cascade that leads to or is responsible for the disorder.

The TrkB binding agonist is used in an effective amount for the methods described. A therapeutically effective amount of the TrkB binding agonist is an amount effective to ameliorate or reduce one or more symptoms of, or to prevent or cure, the disorder.

The TrkB agonist can be used to enhance: cell survival, and/or neuronal repair, and/or neuronal plasticity, both centrally at the CNS and peripherally at the PNS.

The TrkB agonist can be used to treat or prevent a neurological disorder or other disorder where restoring or enhancing the BDNF-TrkB pathway by activating TrkB can be beneficial. Considering the mechanisms of action of the BDNF-TrkB pathway and that TrkB is widely expressed in the CNS and PNS, the TrkB binding agonist can provide therapy to subjects with neurological disorders, neurodegenerative disorders, developmental disorders and other disorders. These are disorders where TrkB agonism is expected to be beneficial.

For example, the TrkB binding agonist may agonise TrkB cellular signalling at the NeuroMuscular Junction (NMJ) and enhance NMJ development, stability and maintenance. The TrkB binding agonist may agonise TrkB cellular signalling in skeletal muscle and regulate proliferation and differentiation of skeletal muscle progenitor cells. This may be beneficial, for example, following muscle injury and degeneration. The TrkB binding agonist may agonise TrkB cellular signalling in Schwann cells and enhance axon regeneration and growth. This may be beneficial, for example, following nerve injury and degeneration.

Disorders include diseases, conditions, syndromes, symptoms and signs. Neurological disorders include neurological diseases, conditions, syndromes, symptoms and signs. A neurological disorder can include those where there is a disruption in the structure or function of component(s) of the central and peripheral nervous system, including the brain, spinal cord, cranial nerves, peripheral nerves, nerve roots, autonomic nervous system, neuromuscular junction, and/or muscles. Neurological disorders can be phenotypically heterogeneous, and often have an unknown etiology. Several mechanisms and pathways have been implicated in neurological disorders such as neurological diseases. In these diseases, specific symptoms and structure/function relationships have led to an understanding of the underlying etiology.

The disorder can also be one where restoring or enhancing the BDNF-TrkB pathway by activating TrkB can be beneficial. For example, in those disorders involving degeneration or dysfunction of cells expressing TrkB.

The TrkB binding agonist may be used in a method of treatment or prevention of the disorders described herein. More specifically, the TrkB binding agonist may be used in a method of treatment of the disorders described herein. The disorders comprise neurodegenerative diseases, optic neuropathies and retinal degenerative conditions, hearing loss disorders, psychiatric disorders, neurodevelopmental disorders, disorders of body weight regulation, muscular disorders and other CNS disorders.

Neurodegenerative diseases include: Amyotrophic Lateral Sclerosis (ALS), Huntington's Disease (HD), Alzheimer's Disease (AD), Motor Neuron Disease (including progressive muscular atrophy), Parkinson's disease, prion diseases including Creutzfeldt-Jakob disease (CJD), Lewy body disease, Spinal muscular atrophy, Multiple system atrophy, Dementia (including fronto-temporal dementia) and tauopathies. More particular neurodegenerative disorders include ALS, Huntington's Disease and Motor Neuron Disease.

In one example, treatment of ALS includes promoting motor neuron survival and function. The TrkB binding agonist may have a neuroprotective and/or neuro-repair effect.

In one example, treatment in reference to dementia or Alzheimer's disease means: to slow the progression of cognitive function decline. The TrkB binding agonist may enhance cell survival, promote neurite outgrowth, and/or regulating synapse plasticity. The TrkB binding agonist may prevent or delay neuronal dysfunction in Alzheimer's disease and other dementias.

In one example, treatment in reference to Huntington's disease means to slow disease progression, including but not limited to slowing progression of cognitive function decline. The TrkB binding agonist may enhance cell survival, promote neurite outgrowth, and/or regulating synapse plasticity. The TrkB binding agonist may prevent or delay neuronal dysfunction in Huntington's disease.

Optic neuropathies include, for example conditions impacting retinal ganglion cells (RGC) and/or the optic nerve. Particular optic neuropathies include: glaucoma (for example open angle glaucoma, wide angle glaucoma, angle closure glaucoma (acute and chronic), normal tension glaucoma), anterior ischaemic optic neuropathy (AION) (for example, non-arteritic ischeamic optic neuropathy (NAION)), posterior ischemic optic neuropathy, radiation optic neuropathy, compressive optic neuropathy (for example, papilledema), infiltrative optic neuropathy, traumatic optic neuropathy, mitochondrial optic neuropathy, toxic optic neuropathies, hereditary optic neuropathies (for example, autosomal dominant optic atrophy (ADOA; optic atrophy type Kjer), Leber hereditary optic neuropathy, Rosenberg Chutorian syndrome, Wolfram syndrome, optic nerve hypoplasia), optic neuritis (for example, neuromyelitis optica, papillitis). Retinal degenerative disorders would include hereditary dystrophies (e.g. retinitis pigmentosa) or acquired conditions including age-related macular degeneration (wet and dry). In one embodiment, optic neuropathies include for example conditions impacting retinal ganglion cells (RGC) and/or the optic nerve. Particular optic neuropathies include: glaucoma (for example open angle glaucoma, wide angle glaucoma, primary angle closure glaucoma, normal tension glaucoma), anterior ischaemic optic neuropathy (AION), non-anterior ischemic optic neuropathy (NAION), traumatic optic neuropathies and Leber hereditary optic neuropathy. Retinal degenerative disorders would include hereditary or acquired conditions including age-related macular degeneration (wet and dry).

Hearing loss disorders include sensorineural hearing loss (SNHL) (bilateral, unilateral and unspecified) and composite hearing loss (in which there are sensorineural and conductive loss elements; bilateral, unilateral and unspecified). Sensorineural hearing loss includes sensory (cochlear related) or a neural ($8^{th}$ nerve related) hearing loss. Sensorineural hearing loss may result from end organ lesions. End organ lesions associated with sensorineural hearing loss include: acoustic trauma (due to a noise greater than, for example 85 decibels (db)), viral endolymphatic labyrinthitis, Meniere's disease, cerebellopontine angle tumors of the 8th nerve, bacterial or viral infection of the 8th nerve ganglia, (e.g. with herpes zoster oticus), purulent labyrinthitis arising from acute otitis media, purulent meningitis, chronic otitis media, sudden deafness including that of viral origin, e.g., viral endolymphatic labyrinthitis caused by viruses including mumps, measles, influenza, chickenpox, mononucleosis and adenoviruses) and transient ischaemic deafness, fractures of the temporal bone extending into the middle ear and rupturing the tympanic membrane and possibly the ossicular chain, fractures affecting the cochlea, and acoustic neurinoma, which are tumors generally of Schwann cell origin that arise from either the auditory or vestibular divisions of the 8th nerve. The end organ lesion hearing loss can be congenital, such as that caused by rubella, anoxia during birth, bleeding into the inner ear due to trauma during delivery, ototoxic drugs administered to the mother, erythroblastosis fetalis, and hereditary conditions including Waardenburg's syndrome and Hurler's syndrome. Sensorineural hearing loss may alternatively be age-related, for example, presbycusis (including presbyacusia), which is a sensorineural hearing loss occurring as a normal part of aging. Sensorineural hearing loss may ototoxic hearing loss (hearing loss resulting from an ototoxic drug (e.g. certain antiobiotics, certain chemotherapeutics, certain salicylate compounds—particularly aspirin—certain diuretics—common loop diuretics- and certain quinines) that affects the auditory portion of the inner ear, particularly the organ of Corti). Sudden sensorineural hearing loss, hidden hearing loss (thought to result from synapse and auditory fibre loss in the inner ear) and tinnitus (possibly resulting from damage to the Organ of Corti) are also included.

Psychiatric disorders include: anxiety, mood disorder, depression (including major depressive disorder), panic disorder, post-traumatic stress disorder (PTSD), attention deficit hyperactive disorder (ADHD), bipolar disorder and Schizophrenia.

Neurodevelopmental disorders include: Angelman syndrome, Prader-Willi syndrome Autistic disorder and Rett syndrome.

Energy balance depends on the regulation of two central circuits that control feeding behaviour: the central nervous system (CNS) must coordinate and integrate appetite, food-seeking behaviour, and thermoregulation; and signals relating to satiety (e.g., from the gut) and overall energy balance must be transduced in the periphery and feedback to the CNS. Therefore disorders of bodyweight regulation include: anorexia nervosa, cachexia, unwanted weight loss (including unwanted weight loss that is related to and/or caused by cancer treatment), sarcopenia, obesity and opioid-induced emesis.

Muscular Disorders Include Sarcopenia.

Other CNS disorders include: diabetic neuropathy, epilepsy, multiple sclerosis, migraine, nerve injury (including traumatic brain injury (TBI), spinal cord injury and peripheral nerve injury), peripheral neuropathies, neuromuscular diseases (including myasthenia gravis and myasthenic syndromes), sleep disorders and Stroke. In one example, peripheral neuropathy includes Chemotherapy induced peripheral neuropathy (CIPN). CIPN is a major dose-limiting side effect of many anticancer drugs.

The TrkB binding agonist can be used as a treatment for neurological disorders and other disorders that will significantly slow/stop/delay progression of the disorder, enhance daily life function, and increase life span of the subject.

In one embodiment, the TrkB binding agonist is used for the treatment of any one of the following disorders: Amyotrophic Lateral Sclerosis (ALS), Huntington's Disease (HD), Stroke, Spinal Cord Injury, Alzheimer's Disease (AD), motor neuron disorders, traumatic brain injury (TBI), dementias, tauopathies, peripheral neuropathy, nerve injury, peripheral nerve injury, Parkinson's disease, prion diseases including Creutzfeldt-Jakob disease (CJD), psychiatric disorders, Schizophrenia, multiple sclerosis, Rett syndrome, Lewy body disease, Multiple system atrophy, myasthenia gravis, diabetic neuropathy, retinal degeneration, glaucoma, hearing loss, bodyweight regulation, anorexia nervosa, cachexia, neuromuscular disease, mood and depressive disorders, post-traumatic stress disorder, attention deficit hyperactive disorder (ADHD), bipolar disorder, anxiety, Autistic disorder, pain, disorders involving bodyweight regulation, anorexia nervosa, cachexia, unwanted weight loss, and opioid-induced emesis.

When used for the treatment or prevention of the disorders described above, the TrkB binding agonist may be administered together with one or more active agents, for example active agents approved for use in the treatment or prevention of the particular disorder and more particularly agents considered to form the current standard of care. Where combination therapy is envisaged, the active agents may be administered simultaneously, separately or sequentially in one or more pharmaceutical compositions.

In embodiments in which the TrkB binding agonist of the invention is used for the treatment of Alzheimer's disease, it may be used in combination with cholinesterase inhibitors and/or memantine.

In embodiments in which the TrkB binding agonist of the invention is used for the treatment of ALS, it may be used in combination with riluzole.

In embodiments in which the TrkB binding agonist of the invention is used for the treatment of glaucoma, it may be used in combination with one or more of: prostaglandin analogues, beta blockers, alpha agonists and carbonic anhydrase inhibitors. In another embodiment in which the TrkB binding agonist of the invention is used for the treatment of glaucoma, it may be used in combination with selective laser trabeculoplasty (SLT) and argon laser trabeculoplasty (ALT).

In one embodiment, the TrkB binding agonist of the invention may used in combination with cochlear implant as a co-therapy to treat sensorineural hearing loss. In another embodiment, the TrkB binding agonist of the invention, this may used in combination with steroids to treat sensorineural hearing loss. In another embodiment, the TrkB binding agonist of the invention, this may used in combination with gene therapy, for example ATOH1 gene therapy, to treat sensorineural hearing loss.

In one particular embodiment, the TrkB binding agonist administered in combination with an ototoxic agent. The skilled person will appreciate that may prevent hearing impairment resulting from the ototoxic agent and may further permit higher doses of the ototoxic agent to be administered to the patient.

The present invention also has the following embodiments:

Embodiment 1

A TrkB binding agonist, wherein the agonist potentiates BDNF-induced agonism of TrkB.

Embodiment 2

The TrkB binding agonist of embodiment 1, wherein the agonist does not compete with BDNF for binding to TrkB.

Embodiment 3

The TrkB binding agonist of embodiment 1 or 2, wherein the potentiating effect of BDNF-induced agonism of TrkB is measured by increased activation of TrkB in the presence of a saturating concentration of BDNF in the presence of the TrkB binding agonist, compared with the absence of the TrkB binding agonist.

Embodiment 4

The TrkB binding agonist of embodiment 3, wherein increased activation of TrkB is measured by increased levels of phosphorylation of TrkB.

Embodiment 5

The TrkB binding agonist of embodiment 4, wherein the phosphorylation of TrkB in the presence of a saturating concentration of BDNF is 100% in the absence of the TrkB binding agonist, compared with at least 110% in the presence of the TrkB binding agonist.

Embodiment 6

The TrkB binding agonist of embodiment 4 or 5, wherein the phosphorylation of TrkB in the presence of a saturating concentration of BDNF is 100% in the absence of the TrkB binding agonist, compared with at least 115%, at least 120%, at least 125%, at least 130%, at least 135%, at least 140%, at least 145%, or at least 150% in the presence of the TrkB binding agonist.

Embodiment 7

A TrkB binding agonist that does not compete with BDNF for binding to TrkB, and binds to an epitope comprised within beta sheets A and G, and the region between beta sheets A and A', of the D5 domain of TrkB.

Embodiment 8

The TrkB binding agonist according to embodiment 7, wherein the epitope comprises residues T288, F291, K372, and E293.

Embodiment 9

A TrkB binding agonist that does not compete with BDNF for binding to TrkB, and binds to an epitope comprised within the juxta-membrane region (W381-H430) of TrkB.

Embodiment 10

The TrkB binding agonist according to embodiment 9, wherein the epitope comprises residues E398, Y397, D399, and Y400.

Embodiment 11

A TrkB binding agonist that does not compete with BDNF for binding to TrkB, and competes for binding to TrkB with a reference antibody having: (a) a heavy chain sequence of SEQ ID NO: 27 and a light chain sequence of SEQ ID NO: 28; or (b) a heavy chain sequence of SEQ ID NO: 29 and a light chain sequence of SEQ ID NO: 30; or (c) a heavy chain sequence of SEQ ID NO: 31 and a light chain sequence of SEQ ID NO: 32.

Embodiment 12

The TrkB binding agonist of any one of embodiments 7 to 11, wherein the TrkB binding agonist potentiates the BDNF induced agonism of TrkB.

Embodiment 13

A TrkB binding agonist, wherein the agonist activates TrkB in the absence of BDNF, and maintains TrkB levels on the cell surface.

Embodiment 14

The TrkB binding agonist according to any one of the preceding embodiments wherein the TrkB binding agonist does not bind to the ligand binding domain of TrkB.

Embodiment 15

A TrkB binding agonist comprising:
(a) (i) any one or a combination of CDRs selected from CDRH1, CDRH2, CDRH3 from SEQ ID NO: 27, and/or CDRL1, CDRL2, CDRL3 from SEQ ID NO:28; or
(ii) a CDR variant of (i), wherein the variant has 1, 2, or 3 amino acid modifications in each CDR; or
(b) a VH region comprising a sequence at least 80% identical to the sequence of SEQ ID NO: 40 and/or a VL region comprising a sequence at least 80% identical to the sequence of SEQ ID NO: 41.

Embodiment 16

A TrkB binding agonist comprising any one or a combination of the following CDRs:
(a) CDRH1 of SEQ ID NO: 6;
(b) CDRH2 of SEQ ID NO: 7;
(c) CDRH3 of SEQ ID NO: 8;
(d) CDRL1 of SEQ ID NO: 3;
(e) CDRL2 of SEQ ID NO: 4; and/or
(f) CDRL3 of SEQ ID NO: 5.

Embodiment 17

The TrkB binding agonist according to embodiment 15 or 16, wherein the binding agonist comprises CDRL1, CDRL3, and CDRH3.

Embodiment 18

The TrkB binding agonist according to embodiment 17, wherein the binding agonist additionally comprises CDRH2.

Embodiment 19

The TrkB binding agonist according to any one of embodiments 15 to 18, wherein the binding agonist comprises:
(a) a humanised VH region, or a humanised Heavy Chain (HC) sequence; and/or
(b) a humanised VL region, or a humanised Light Chain (LC) sequence.

Embodiment 20

The TrkB binding agonist according to any one of embodiments 15 to 19, wherein VH position 47 is Cys, Ser, Gly, Ala, Val, Thr or Asn.

Embodiment 21

A TrkB binding agonist comprising:
(a) a VH region of SEQ ID NO: 40; and/or
(b) a VL region of SEQ ID NO: 41.

Embodiment 22

The TrkB binding agonist according to any one of embodiments 15 to 21, wherein the binding agonist comprises:
(a) a Heavy Chain (HC) sequence at least 80% identical to SEQ ID NO: 42; and/or
(b) a Light Chain (LC) sequence at least 80% identical to SEQ ID NO: 43.

Embodiment 23

A TrkB binding agonist comprising:
(a) a Heavy Chain (HC) sequence of SEQ ID NO: 42; and/or
(b) a Light Chain (LC) sequence of SEQ ID NO: 43.

Embodiment 24

The TrkB binding agonist according to any one of embodiments 15 to 23 that agonises human TrkB receptor, does not compete with BDNF, and potentiates the BDNF-induced agonism of TrkB.

Embodiment 25

The TrkB binding agonist according to any one of the preceding embodiments, wherein the Fc region is disabled.

Embodiment 26

The TrkB binding agonist according to any one of the preceding embodiments, wherein the binding agonist comprises a synthetic sequence, a humanised sequence, or a chimeric sequence.

Embodiment 27

A nucleic acid sequence which encodes the TrkB binding agonist as defined in any one of the preceding embodiments.

Embodiment 28

The nucleic acid sequence according to embodiment 27, wherein the sequence comprises SEQ ID NO: 44 encoding the heavy chain; and/or SEQ ID NO: 45 encoding the light chain.

Embodiment 29

An expression vector comprising the nucleic acid sequence as defined in embodiment 27 or 28.

Embodiment 30

A recombinant host cell comprising the nucleic acid sequence as defined in embodiment 27 or 28, or the expression vector as defined in embodiment 29.

Embodiment 31

A method for the production of the TrkB binding agonist as defined in any one of embodiments 1 to 26, which method comprises culturing the host cell as defined in claim 30 under conditions suitable for expression of said nucleic acid sequence or vector, whereby the TrkB binding agonist is expressed and purified.

Embodiment 32

A TrkB binding agonist produced by the method of embodiment 31.

Embodiment 33

A pharmaceutical composition comprising the TrkB binding agonist as defined in any one of embodiments 1 to 26 or embodiment 32, and one or a combination of pharmaceutically acceptable carriers, excipients or diluents.

Embodiment 34

A TrkB binding agonist as defined in any one of embodiments 1 to 26 or embodiment 32, or a pharmaceutical composition as defined in embodiment 33 for use in therapy.

Embodiment 35

A TrkB binding agonist as defined in any one of embodiments 1 to 26 or embodiment 32, or a pharmaceutical composition as defined in embodiment 33 for use in the treatment of a neurological disorder.

Embodiment 36

A TrkB binding agonist as defined in any one of embodiments 1 to 26 or embodiment 32, or a pharmaceutical composition as defined in embodiment 33, for use in the treatment of a neurological disorder or other disorder where restoring or enhancing the BDNF-TrkB pathway by activating TrkB can be beneficial.

Embodiment 37

A TrkB binding agonist for use according to embodiment 35 or 36, wherein the disorder is: a neurodegenerative disease, an optic neuropathy, a retinal degenerative condition, a disorder involving hearing loss, a psychiatric disorder, a neurodevelopmental disorder, a disorder of body weight regulation, a muscular disorder and another CNS disorder.

Embodiment 38

A TrkB binding agonist for use according to embodiment 37, wherein the disorder is: Amyotrophic Lateral Sclerosis (ALS), Huntington's Disease (HD), Alzheimer's Disease (AD), Motor Neuron Disease, Parkinson's disease, prion diseases, Lewy body disease, Spinal muscular atrophy, Multiple system atrophy, Dementia and tauopathies, glaucomaanterior ischaemic optic neuropathy (AION), non-anterior ischeamic optic neuropathy (NAION), traumatic optic neuropathies, Leber hereditary optic neuropathy, age-related macular degeneration, neural deafness, cochlear deafness, tinnitus, sensorineural hearing loss, composite hearing loss, anxiety, mood disorder, depression, panic disorder, post-traumatic stress disorder (PTSD), attention deficit hyperactive disorder (ADHD), bipolar disorder, Schizophrenia, Angelman syndrome, Prader-Willi syndrome, Autistic disorder, Rett syndrome, anorexia nervosa, cachexia, unwanted weight loss, sarcopenia, obesity, opioid-induced emesis, sarcopenia, diabetic neuropathy, epilepsy, multiple sclerosis, migraine, nerve injury, peripheral neuropathy, neuromuscular disease, sleep disorder and Stroke.

Embodiment 39

The TrkB binding agonist of any one of embodiments 34, 35, 36, 37 or 38, wherein treatment comprises enhancement of: cell survival, and/or neuronal repair, and/or neuronal plasticity.

Embodiment 40

A potentiator of BDNF-induced agonism of TrkB, for use in therapy.

EXAMPLES

1. TrkB Agonists

Mouse monoclonal antibodies against the TrkB receptor were generated by immunization of Balb/c mice with recombinant human TrkB extracellular domain (hereafter referred to as TrkB-ECD, SEQ ID NO:1, D1-D2-D3-D4-D5-JM, C32-H430, 399 amino acids) generated using HEK293-6E cell line expression and purification. The TrkB-ECD used for immunization was FLAG tagged via a GSA linker, and had a His tag (5 His residues) at the C-terminus (FLAG tag-GSA-C32-H430-His5). Screening of the hybridoma fusion clones (~3000 wells) was conducted by selecting clones that showed a correlation between (i) direct antigen ELISA (i.e. binding to TrkB-ECD), and (ii) TrkB activation-dependent NFAT promoter driven reporter assay (i.e. agonists of TrkB). This selection criteria led to the identification of multiple hybridoma clones expressing the murine agonist antibodies 1G11, 3A3 (same antibody sequence as 3B3), 8E5, 5D11 (same as 3E10), 5C7 (same antibody sequence as 5E6), 3A4, and 2A1.

1.1 Affinity

1G11 demonstrated binding to human TrkB-ECD with an affinity of ~42 nM ($k_{on}$=5.66×10$^4$/Ms, $k_{off}$=0.00239/s) as determined by surface plasmon resonance. The affinity of 1G11 is shown in Table 3, together with the affinities of other agonist antibodies identified.

1.2 Receptor Selectivity

Evaluation of 1G11 selectivity against the Trk family of receptors using a Trk activation dependent NFAT promoter driven reporter assay in CHO-K1 cells expressing either TrkA or TrkB or TrkC revealed that 1G11 selectively induced reporter gene expression in cells expressing TrkB receptors, but not in TrkA or TrkC receptor expressing cells at the concentrations tested (0.00006-125 nM). As a control, the cognate ligands (NGF for TrkA, BDNF for TrkB and NT-3 for TrkC) induced comparable levels of reporter gene expression in corresponding Trk receptor expressing cells. 1G11 was also tested for its ability to bind the pan-neurotrophin receptor, p75$^{NTR}$. The cell based binding assay showed no detectable binding of 1G11 to p75$^{NTR}$ receptor. The receptor selectivity of the TrkB agonists is summarised in Table 3.

1.3 Cross Species Reactivity

1G11 binds to and activates rodent (murine, rat), cynomolgus, and human TrkB receptors. 2A1 and 5D11 also activate rat, mouse and human TrkB receptors. Interestingly, 3A3 and 8E5 only activate the human TrkB receptors but not the rodent TrkB receptors. The species cross-reactivity was tested using either recombinantly expressed TrkB receptors in heterologous cell line or primary cells derived from corresponding species or human iPSC derived cells. The species selectivity of the TrkB agonists is summarised in Table 3.

1.4 Activation of TrkB

CHO-K1 stably expressing human full-length TrkB receptor (SEQ ID NO:2) when treated with 1G11 led to TrkB activation as measured by the phosphorylated levels of TrkB (pTrkB, Y515) with an average $EC_{50}$ of 3.1±2.1 nM (mean±S.D., n=8). The TrkB activation effect of the TrkB agonists is summarised in Table 3. 1G11 by itself activates the TrkB receptor to about 30-40% of the cognate ligand BDNF (as well as NT-4) maximal response.

Figure 1B:
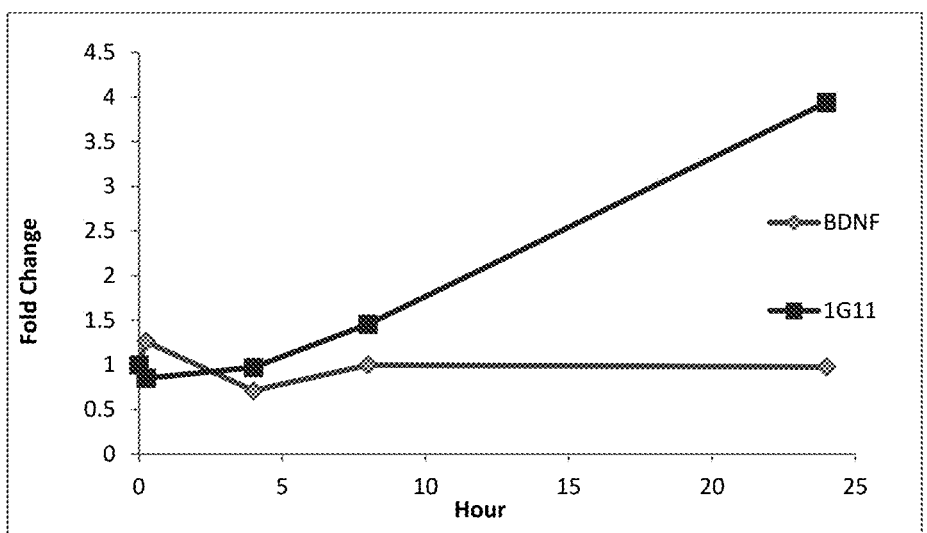
FIG. 1B: BDNF and 1G11 induced cell surface levels of TrkB as a proportion of total cellular TrkB over time. Rat cortical neurons in culture (7 days in vitro) were treated with 0.8 nM BDNF or 7.3 nM 1G11 as indicated at 37° C. The relative surface levels of TrkB compared to total TrkB was determined by densitometric analysis. The ratio of surface TrkB to total TrkB is shown as fold change compared to untreated control at zero time point.

1G11 induced sustained activation of TrkB and its downstream signalling pathways in rat cortical neurons (up to 24 hours) indicating that 1G11 when exposed to TrkB can maintain the receptor in the activated state for a prolonged period of time, compared with BDNF (see FIG. 1A). Mechanistically, 1G11 induced TrkB activation is different from BDNF. Activated tyrosine kinase receptors typically undergo endocytosis followed by degradation resulting in down regulation of the cell surface receptors thereby becoming non-responsive to the ligand temporarily to maintain cellular homeostasis. Interestingly, 1G11 did not alter the surface levels of TrkB in rat cortical neurons up to 4 hrs, however levels increased at 24 hours compared to untreated controls despite reduction in total cellular levels of TrkB receptors as measured by cell surface biotinylation (see FIG. 1B).

1.5 BDNF Competition

1G11's activation effect on TrkB receptor was determined by TrkB phosphorylation both in the presence and absence of BDNF. The competitive effect of the TrkB agonists in the presence of BDNF was defined as reduced TrkB phosphorylation. Evaluation of the effect of different concentrations of 1G11 on TrkB phosphorylation in the presence of saturating BDNF concentration (10 nM, EC100) in the CHO cells overexpressing full-length TrkB receptor revealed that 1G11 does not compete with BDNF for TrkB. The only TrkB agonist identified that did compete with BDNF was 5D11, which reduced BDNF-induced TrkB phosphorylation by ~50%. The BDNF competition results of the TrkB agonists are summarised in Table 3.

1.6 TrkB Agonist Competition Assays

To analyse the epitope binding properties of the TrkB agonist mAbs, competition assays were set up to determine which TrkB agonists competed with each other, to enable grouping together of those which bound to similar or overlapping epitope(s) on TrkB. TrkB-ECD was immobilized on a chip surface and a single TrkB agonist mAb was injected into flow cells for binding to TrkB. The second TrkB agonist mAb was then injected and its binding capacity to TrkB-ECD in presence of the $1^{st}$ TrkB agonist mAb was assessed. Competition was categorised as: "no" with less than 20% binding of the $2^{nd}$ TrkB agonist; "partial" with 20-60% binding of the $2^{nd}$ TrkB agonist; and "yes" with more than 60% binding of the $2^{nd}$ TrkB agonist. Thus "no" binding of the second TrkB agonist was concluded as no competition, and thus the two TrkB agonists binding to non-overlapping epitopes, or alternately binding of the $1^{st}$ TrkB agonist alters the TrkB-ECD conformation in such a way that the $2^{nd}$ TrkB agonist was unable to bind. "Partial" and "yes" was concluded as competition of the two TrkB agonists for binding to a similar or overlapping epitope(s) on TrkB.

The TrkB agonist competition results are summarised in Table 3 (competition with 1G11, or 3A3, or 8E5). Table 2 shows that 1G11, 3A3, and 8E5 can be grouped together as TrkB agonists that compete with each other for binding to a similar or overlapping epitope(s) on TrkB.

1.7 BDNF Potentiation

The potentiation effect of 1G11 on BDNF-induced agonism of TrkB was assessed by measuring TrkB phosphorylation levels (pTrkB, Y515) in the presence of BDNF. Evaluation of the effect of different concentrations of 1G11 on TrkB in the presence of saturating BDNF concentration (10 nM, EC100) in CHO cells overexpressing full-length TrkB receptor (SEQ ID NO:2) resulted in enhancement in the steady state levels of TrkB activation 30 minutes following treatment, as reflected in maximal response (BDNF—100%; BDNF+1G11—~100%-145%), as shown in FIG. 2.

Figure 2:
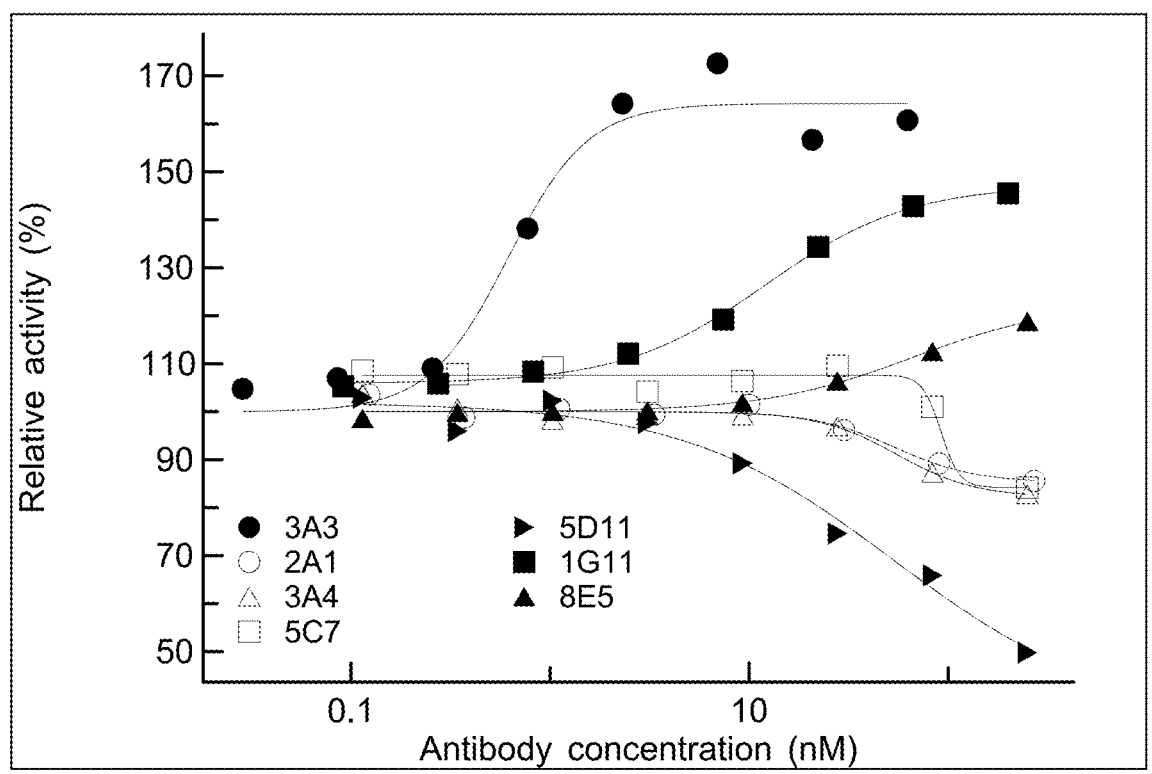
FIG. 2: Representative data showing TrkB agonist antibodies with different properties-potentiators and non-competitors (3A3, 1G11, 8E5), competitors (5D11), non-competitors (2A1, 3A4, 5C7). 100% activity represents TrkB activation at saturating concentration of BDNF i.e. 10 nM EC100.

Evaluation of other TrkB agonists in the presence of saturating BDNF concentration revealed that 3A3 and 8E5 also "potentiated" TrkB receptor activation (~100-165%, and ~100-120%, respectively), as shown in FIG. 2. These results are summarised in Table 3.

Interestingly, clones 5C7, 5E6, 3A4 and 2A1 neither competed nor potentiated BDNF mediated TrkB receptor activation indicating that (a) not all agonist antibodies will harbour the potentiating property, and (b) not all ligand non-competitive antibodies will be potentiators.

FIG. 2 shows representative data for the TrkB antibodies—potentiators and non-competitors (3A3, 1G11, 8E5), competitors (5D11), non-competitors (2A1, 3A4, 5C7). 100% activity represents TrkB activation at saturating concentration of BDNF i.e. 10 nM EC100. BDNF levels have been reported to be decreased in most neurological and pathophysiological diseases and the phenotypes/deficits have been attributed to this reduction. Under BDNF deficient pathophysiological conditions, where TrkB receptor levels remain unaltered, a physiological cellular/system response could still be elicited if the administered therapeutic TrkB agonist could: (i) activate TrkB receptors (e.g. 1G11, 3A3, 8E5, 5D11, 5C7, 5E6, 3A4 and 2A1), (ii) not compete with the reduced levels of BDNF (e.g. 1G11, 3A3, 8E5, 5C7, 5E6, 3A4 and 2A1), (iii) potentiate the cellular signalling induced by the reduced physiological levels of BDNF (e.g. 1G11, 3A3, 8E5), and (iv) without altering the cell surface levels of TrkB (e.g. 1G11), which otherwise may potentially result in temporary desensitization to the TrkB agonist. This data is also summarised in Table 3.

1.8 NT-4 Potentiation

Similarly, 1G11 failed to compete with NT-4 and displayed the "potentiation" effect on NT-4-induced agonism of TrkB in the presence of saturating levels of NT-4 (NT-4-100%; NT-4±1G11-~130%; Table 3). It is therefore expected that 3A3 and 8E5 will also have a potentiating effect on NT-4 induced agonism of TrkB.

1.9 Cell Survival and Repair

1G11 promoted the survival of and induced neurite outgrowth in the rat PC12 neuroblastoma cell line stably expressing human full length TrkB receptor in a concentration-dependent manner with an average $EC_{50}$ of 0.025±0.01 nM and 0.19±0.06 nM respectively. 1G11 activated endogenously expressed TrkB receptors in rat brain and spinal cord derived neurons, mouse brain derived neurons, and recombinantly expressed cynomolgus TrkB in CHO cells.

Similarly 8E5 and 3A3 enhanced cell survival with an EC50 of 0.09±0.06 nM (mean±SD) and 0.006±0.001 nM (mean±SD), respectively.

While 8E5 induced neurite outgrowth in a concentration-dependent manner with an EC50 of 1.58±0.34 nM (mean±SD), 3A3 consistently displayed a biphasic neurite outgrowth response with increasing antibody concentrations making it challenging to derive accurate EC50.

TABLE 3

| | 1G11 | 3A3 (=3B3) | 8E5 | 5D11 (=3E10) | 5C7 (=5E6) | 3A4 | 2A1 |
|---|---|---|---|---|---|---|---|
| Affinity KD (nM) | ~42 nM ($k_{on}$ = 5.66 × $10^4$/Ms, $k_{off}$ = 0.00239/s) | ~7.5 nM ($k_{on}$ = 1.2 × $10^5$/Ms, $k_{off}$ = 8.97 × $10^{-4}$/s) | ~9.8 nM ($k_{on}$ = 6.9 × $10^4$/Ms, $k_{off}$ = 6.76 × $10^{-4}$/s) | ~3.3 nM ($k_{on}$ = 4.41 × $10^4$/Ms, $k_{off}$ = 1.45 × $10^{-4}$/s) | | | ~68 nM ($k_{on}$ = 6.1 × $10^3$/Ms, $k_{off}$ = 4.17 × $10^{-4}$/s) |
| Receptor selectivity | TrkB (negative for TrkA and TrkC) | TrkB (negative for TrkA and TrkC) | TrkB (negative for TrkA) TrkC: ND | TrkB (negative for TrkA and TrkC) | TrkB (negative for TrkA and TrkC) | TrkB (negative for TrkA and TrkC) | TrkB (negative for TrkA and TrkC) |
| Species selectivity | Murine, rat, cynomolgus, human | Human, not active in rat | Human, not active in rat | Murine, rat, cynomolgus, human | | | rat, human |
| Activation of TrkB (pTrkB) | $EC_{50}$ of 3.1 ± 2.1 nM | $EC_{50}$ of 0.2-0.6 nM | $EC_{50}$ of ~15 nM | $EC_{50}$ of 1-2 nM | | | $EC_{50}$ of ~5-6 nM |
| Competition with BDNF | No | No | No | Yes | No | No | No |
| Competition with NT-4 | No | ND | ND | ND | ND | ND | ND |
| Competition with 1G11 | — | Partial 20-60% (1G11 $1^{st}$, 3A3 $2^{nd}$) | Yes >60% (1G11 1st, 8E5 $2^{nd}$) | | No >20% (1G11 $1^{st}$, 5C7 $2^{nd}$) No >20% (5C7 $1^{st}$, 1G11 $2^{nd}$) | | ND |
| Competition with 3A3 | Yes >60% (3A3 $1^{st}$, 1G11 $2^{nd}$) | — | Yes >60% (3A3 $1^{st}$, 8E5 $2^{nd}$) | | No >20% (3A3 $1^{st}$, 5C7 $2^{nd}$) No >20% (3A3 $1^{st}$, 1G11 $2^{nd}$) | | ND |
| Competition with 8E5 | Yes >60% (8E5 $1^{st}$, 1G11 $2^{nd}$) | Partial 20-60% (8E5 $1^{st}$, 3A3 $2^{nd}$) | — | | No >20% (8E5 $1^{st}$, 5C7 $2^{nd}$) No >20% (5C7 $1^{st}$, 8E5 $2^{nd}$) | | ND |
| Potentiation of BDNF-induced agonism of TrkB | Yes ~130% | Yes ~160% | Yes ~120% | No | No | No | No |
| Potentiation of NT-4-induced agonism of TrkB | Yes 130% | ND | ND | ND | ND | ND | ND |
| Increased surface levels of TrkB | Yes, ~4 fold to BDNF control | ND | ND | ND | ND | ND | No |
| Activation of p-Akt, p-Erk and/or p-Creb | Yes, increased p-Akt, p-Erk and p-Creb | ND | ND | Yes, increased p-Akt and p-Erk | ND | ND | Yes, increased p-Akt and p-Erk |

ND: not determined

2. Sequencing of 1G11, 3A3, and 5D11

The TrkB agonists were sequenced by conventional techniques. The CDRs were determined by Kabat and are presented for 1G11, 3A3, 8E5, and 5D11 in Table 4 (note that the CDR regions for 1G11 determined by different numbering conventions are presented in Table 1). The full length murine sequences (heavy chain and light chain) for each of 1G11 (SEQ ID NO: 27 and 28), 3A3 (SEQ ID NO: 29 and 30), 8E5 (SEQ ID NO: 31 and 32), and 5D11 (SEQ ID NO: 33 and 34) are also referenced in Table 4.

TABLE 4

| Kabat CDRs | | SEQ ID NO: | Heavy chain SEQ ID NO: | Light chain SEQ ID NO: |
|---|---|---|---|---|
| 1G11 | | | | |
| CDRL1 | RASQRISNNLH | 3 | 27 | 28 |
| CDRL2 | YVSQSIS | 4 | | |
| CDRL3 | QQSNSWPLT | 5 | | |
| CDRH1 | SYYIN | 6 | | |

TABLE 4 -continued

| Kabat CDRs | | SEQ ID NO: | Heavy chain SEQ ID NO: | Light chain SEQ ID NO: |
|---|---|---|---|---|
| CDRH2 | RIAPGNTYYNEIFKG | 7 | | |
| CDRH3 | RGYEGALDY | 8 | | |
| 3A3 (383) | | | | |
| CDRL1 | KSSQSLLYSGNQKNYLA | 9 | 29 | 30 |
| CDRL2 | WASTRES | 10 | | |
| CDRL3 | QQYYSYPYT | 11 | | |
| CDRH1 | SYWMH | 12 | | |
| CDRH2 | YINPSTGYTDYNQKFKD | 13 | | |
| CDRH3 | SRAARY | 14 | | |
| 8E5 | | | | |
| CDRL1 | RASSSVSSSYLH | 15 | 31 | 32 |
| CDRL2 | STSNLAS | 16 | | |
| CDRL3 | QQYSGYPLT | 17 | | |
| CDRH1 | TYGMS | 18 | | |
| CDRH2 | TVSTGGTYTYYPDSVKG | 19 | | |
| CDRH3 | GGYSFAY | 20 | | |
| 5D11 (3E10) | | | | |
| CDRL1 | RASQSVSTSFYSYMH | 21 | 33 | 34 |
| CDRL2 | YASNLQS | 22 | | |
| CDRL3 | QHSWEIPWT | 23 | | |
| CDRH1 | NYLIE | 24 | | |
| CDRH2 | VINPGSGGTNYNDKFKG | 25 | | |
| CDRH3 | GGNDYGDY | 26 | | |

2. Epitope

The TrkB primary amino acid sequence is highly conserved across mouse, rat, cynomolgus and human (95% across the full-length sequence), and particularly conserved in the extracellular domain where all the TrkB agonists identified in Example 1 bind. To determine binding epitopes on TrkB, epitope mapping studies were performed by domain deletion and alanine scanning mutagenesis (using surface plasmon resonance), as well as X-ray crystallography studies, using TrkB ECD (SEQ ID NO:1). The TrkB ECD includes 5 domains (D1-D3: C32-C194; D4: G195-V283; D5: H284-G380) and a short juxtamembrane JM region (W381-H430). The TrkB-ECD used for epitope mapping studies was FLAG tagged via a GSA linker, and had a His tag (5 His residues) at the C-terminus (FLAG tag-GSA-C32-H430-His5).

Deletion domain variants were generated: the D1-D3 domain variant includes C32-L196 (SEQ ID NO:35); the D4-D5-JM domain variant includes P197-H430 (SEQ ID NO:36), and the D5-JM domain variant includes H284-H430 (SEQ ID NO:37).

For alanine scanning mutatgenesis studies (2.2, 2.3 and 2.5), single point mutants were made in TrkB-ECD (SEQ ID NO: 1) as listed:
N193A; S198A; N200A; L206A; E210A; K212A; S213A; T215A; S217A; D223A; N227A; Y229A; D231A; N234A; V236A; H239A; S244A; T246A; S249A; R251A; Q263A; L271A; Q276A; T288A; F291A; E293A; T296A; D298A; H299A; K308A; K312A; F318A; N325A; K328A; K333A; H335A; H343A; N350A; M354A; K364A E366A E371A K372A Q373A H377A M379A W381A D385A N389A D394A E398A T402A; D406A; T410A; N415A; T420A; D424A; R428A; F285A; T290A; S294A; H300A; S327A; Y329A; C331A; Q347A; D349A; T352A; D370A; D386A; N391A; Y392A; V395A; I396A; Y397A; D399A; Y400A; N405A; D358A; or S375A.

2.1 Binding Between TrkB and BDNF

Figure 3:
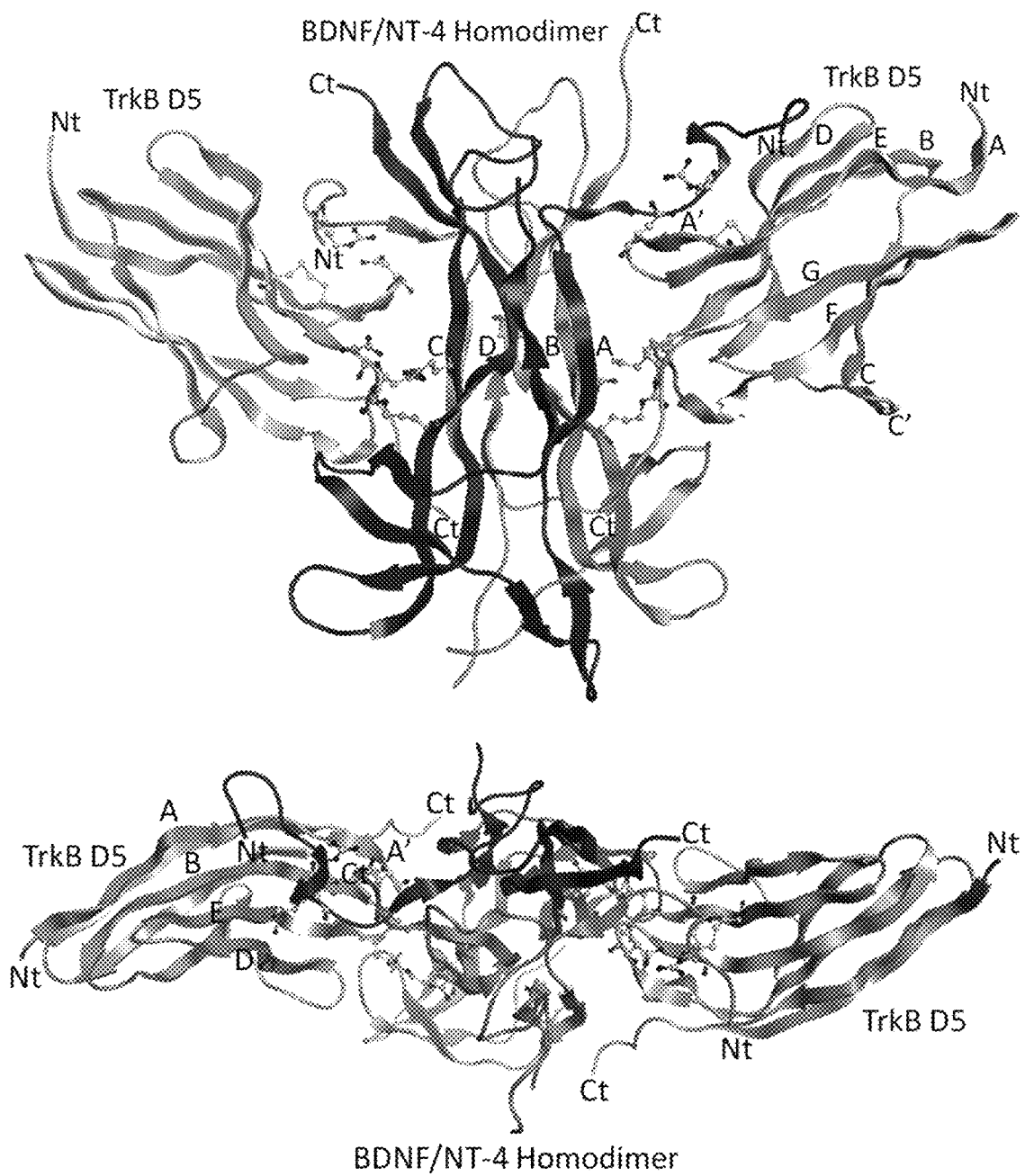
FIG. 3: Structural interactions between the BDNF/NT-4 homodimer and two TrkB D5 domains showing various secondary structures (beta sheets, loops, N-terminus "Nt", and C-terminus "Ct"), based on published structures.

It is known that the D5 domain of TrkB (residues 286-384) can replace full length TrkB for binding to the ligand (BDNF/NT-4). There are two contact regions within the ligand binding site of TrkB: the "conserved patch" and the "specificity patch". The contact residues of TrkB D5 in the conserved patch are from the loops between AB, C'D and EF beta sheets, and the C-terminus of the D5 domain. The conserved patch of TrkB binds to the stalk of the ligand (BDNF/NT-4). The contact residues of TrkB D5 in the specificity patch are from the external face of the ABED beta sheet. The specificity patch of TrkB binds to the N-terminus of the ligand (BDNF/NT-4) which is disordered in the unliganded form and becomes ordered upon binding to TrkB. The structural interactions between the BDNF/NT-4 homodimer and two TrkB D5 domains are summarised in FIG. 3.

2.2 Epitope of 1G11

Initial surface plasmon resonance binding analysis of 1G11 with different TrkB domain deletion variants revealed that 1G11 binds to TrkB-ECD (C32-H430), the D4-D5 domain variant (P197-H430), and the D5 domain variant (H284-H430), but not to the D1-D3 domain variant (C32-L196).

Surface plasmon resonance binding analysis of 1G11 with ~80 single point alanine mutants in TrkB-ECD, mostly in the D4-D5-JM domain, identified 8 amino acids as critical residues for binding, although to varying extents showing the most important first: F291, E293>K372, E210, T288, D370>F285, T290. All the residues are from the D5 domain of TrkB, except for E210 which is in the D4 domain.

The co-crystal structure of 1G11 chimeric Fab1 [variable region from 1G11 fused with constant region from human IgG1] (SEQ ID NOs: 38 and 39) complexed with the D5-JM domain of TrkB(SEQ ID NO: 37) at 2.3 Å resolution revealed 14 residues on the D5-JM domain of TrkB that closely approach IG11 (using a distance cut-off of 4.5 Å). The 14 residues identified included those that were also identified by alanine scanning analysis (T288, F291, K372, E293); as well as other amino acid residues that are in close proximity (I289, T290, L292, S294, K308, D358, E371, Q373, I374, S375) only identified by X-ray crystallography. Using a distance cut-off of 3.5 Å at 2.3 Å resolution, identified 7 residues (290, 293, 294, 372, 373, 374, 375).

The interactions involved in the epitope were defined using CCG (Chemical Computing Group) MOE v2015.1001 (Molecular Operating Environment). Protein residues within 7 Å of the 1G11 chimeric Fab1 on the D5-JM domain of TrkB were selected, and then the "Ligand Interaction" tool with the default parameters was used to identify water molecules or residues from the interacting molecule that were deemed to be interacting with these residues. Note that due to this tool being designed for defining small molecule ligand interactions, rather than protein residues, the "Ligand interactions" of each selected residue were calculated individually. The interactions defined by MOE were edited in Excel to delete any intrachain interactions, and to delete all water interactions apart from those that formed a bridge between the two chains. The remaining interacting residues are as follows:

Direct interaction with 1G11 chimeric Fab1 residues
    Thr290, Glu293, Ser294, Asp358, Ser375
Direct interaction with 1G11 chimeric Fab1 residues, and indirect interaction via water
    Lys372, Gln373
Indirect interaction via water only
    Glu341

The analysis of the co-crystal structure and alanine scan mutagenesis complement and corroborate with each other, and identify residues in the D5-JM domain of TrkB that either interacts with the TrkB agonist or indirectly influence binding through structural interactions.

Using the alanine scanning data and the X-ray data, it appears that K372 and E293 as a minimum, are part of the TrkB epitope to which 1G11 binds. This data is summarised in Table 5.

E293 is located between D5 beta sheets A and A'; and K372 is located in D5 beta sheet G. Residues T288 and T291 (identified by alanine scanning and proximity analysis) are located in D5 beta sheet A.

Figure 4A:
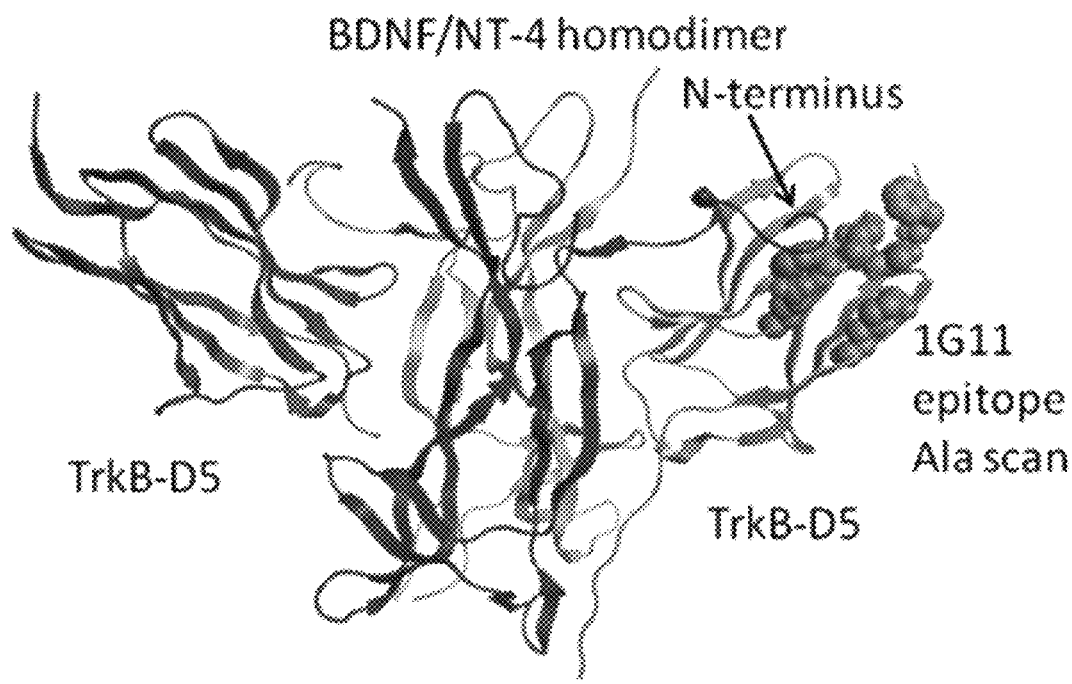
FIG. 4: Structural interactions between the BDNF/NT-4 homodimer and two TrkB D5 domains and 1G11. The residues identified by alanine scanning are shown in FIG. 4A, and the residues identified by co-crystal X-ray crystallography are shown in FIG. 4B.
Figure 4B:
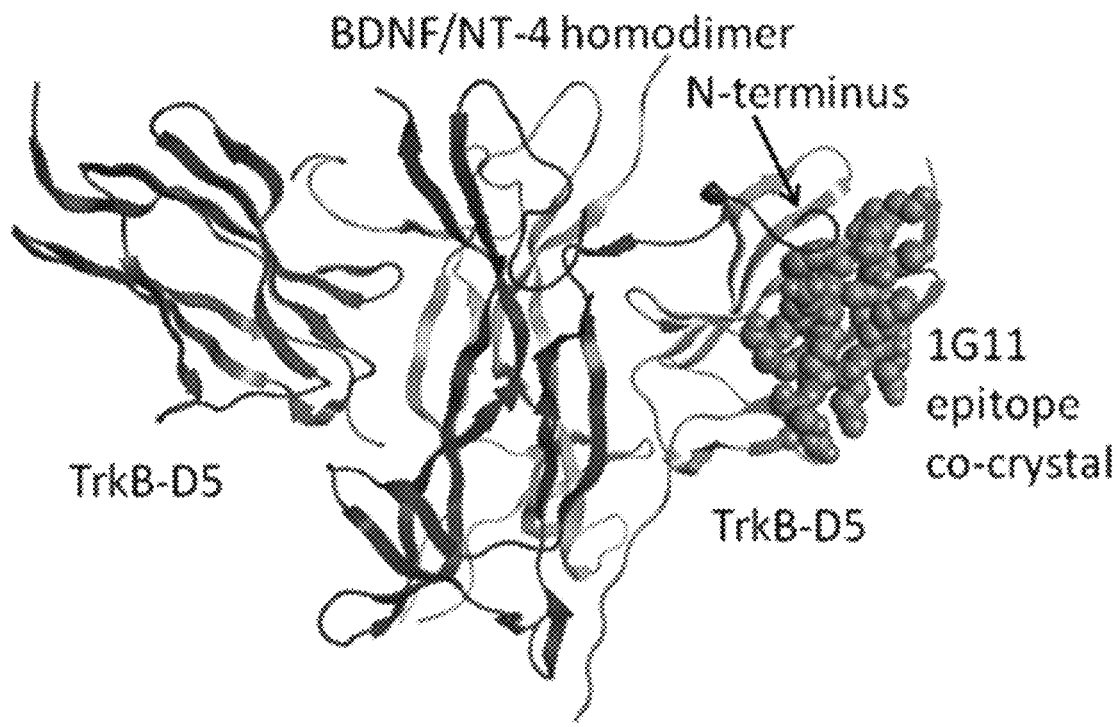

The residues identified by alanine scanning are shown in FIG. 4A, and the residues identified by co-crystal X-ray crystallography proximity analysis are shown in FIG. 4B. In FIG. 4, the D5 TrkB domain from the co-crystal structure of 1G11 Fab bound to TrkB D5 was superimposed with the same TrkB domain from the published co-crystal structure of human TrkB domain D5 bound to NT-4 homodimer to orientate the binding of TrkB to ligand with respect to the 1G11 Fab. The BDNF chain from the human BDNF/NT-4 heterodimer was subsequently superimposed to show the potential binding site of TrkB on BDNF. The C-terminus of TrkB D5 from the published co-crystal structure of human TrkB domain D5 bound to NT-4 homodimer was extended using beta-strand geometry to join the juxtamembrane (JM) region and up to the transmembrane region to demonstrate the potential length of this missing region, due to lack of published/available crystal structure data. The structure was displayed using a ribbon cartoon format and atoms were displayed on the structures for residues that were indicated as potential TrkB epitopes.

It can be seen from FIGS. 4A and 4B, that the epitope of 1G11 is located on TrkB D5 domain proximal to the BDNF/NT4 "conserved patch" ligand binding site (loops between AB, C'D and EF beta sheets, and the C-terminus of the D5 domain), and close to the BDNF/NT4 "specificity patch" ligand binding site (external face of the ABED beta sheet). More particularly, the 1G11 epitope on TrkB domain 5 appears to be along D5 beta sheet A, the region between D5 beta sheets A and A', and D5 beta sheet G, close to the external face of the ABED beta sheet of the specificity patch. The fact that 1G11 epitope on TrkB does not overlap directly with the BDNF/NT4 ligand binding site, presumably allows for 1G11 to bind to TrkB, and for TrkB to also bind to BDNF/NT-4, to form a ternary complex "TrkB agonist+TrkB+ligand".

Figure 5:
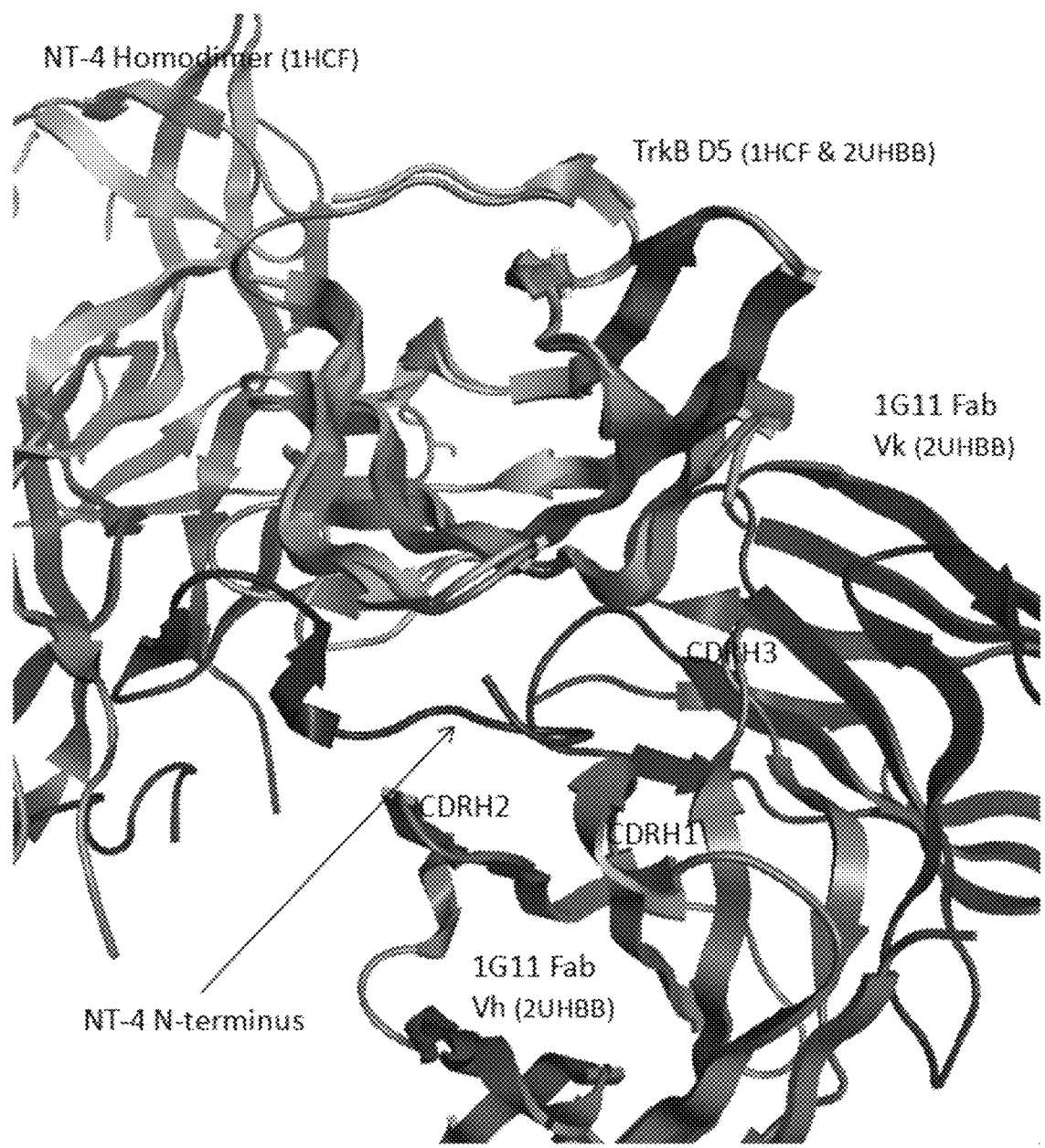
FIG. 5: Further structural analysis of the BDNF/NT-4 homodimer and two TrkB D5 domains and 1G11 shows that the N-terminus of NT-4/BDNF potentially protrudes into a space between TrkB and the Heavy Chain of the 1G11 Fab.
Figure 6:
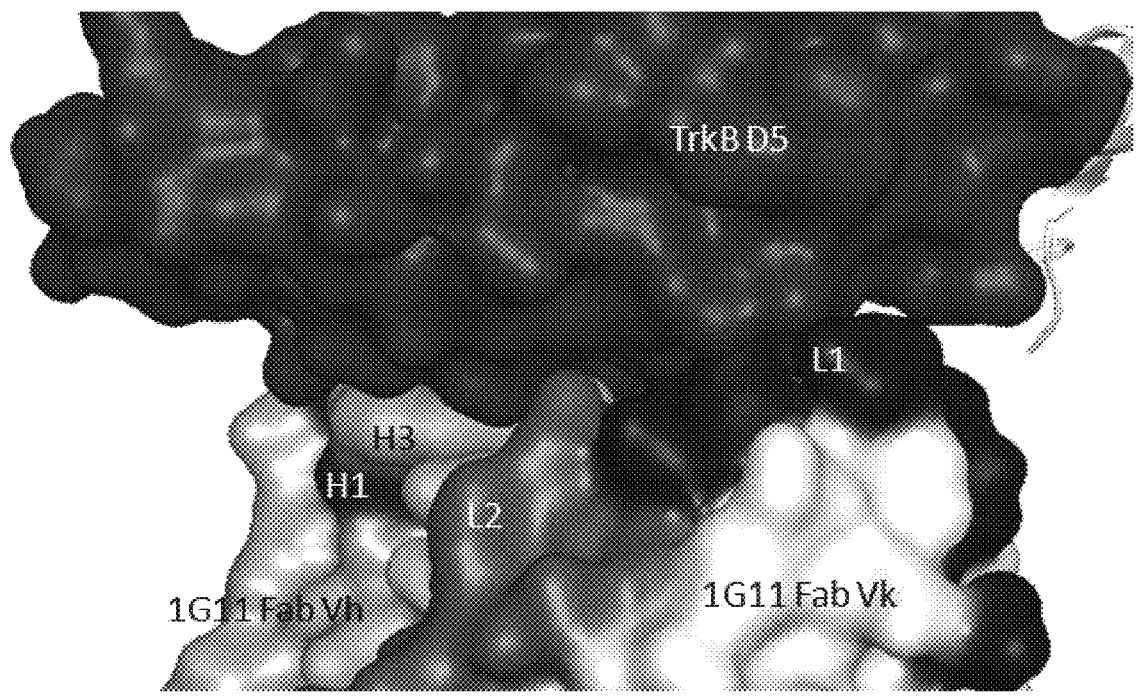
FIG. 6: addition of molecular surfaces to the structural analysis of the BDNF/NT-4 homodimer and two TrkB D5 domains and 1G11 shows that the VK CDRs L1 and L3, and CDRH3 interact closely with TrkB, and there is a cleft between TrkB and CDRs H1 and H2 which could be envisaged to potentially accommodate the N-terminus of BDNF.
Figure 6:
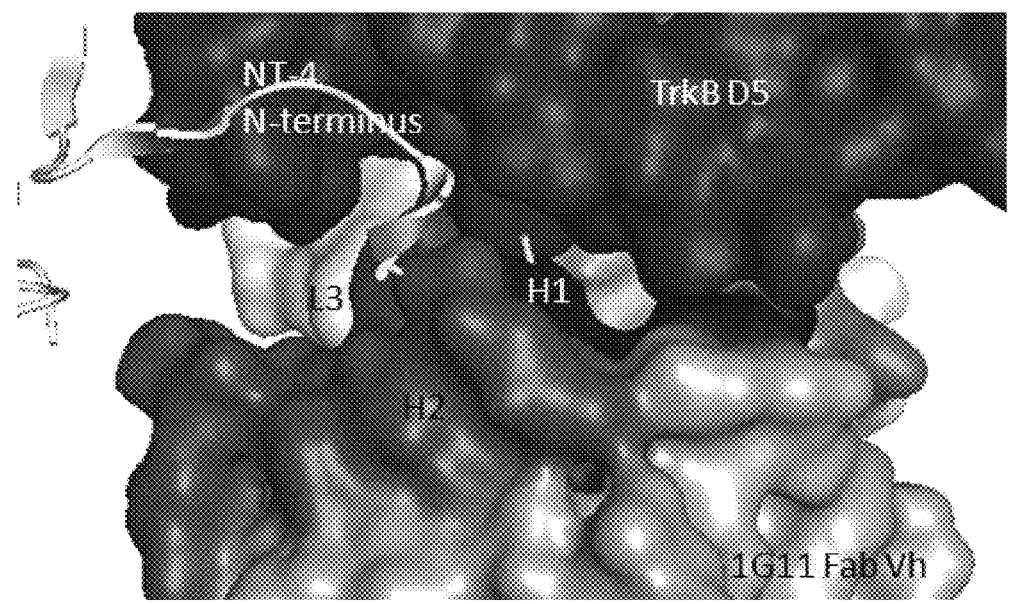

Further analysis of the superimposition of the 1G11, TrkB, BDNF/NT-4 components shows that the N-terminus of NT-4/BDNF potentially protrudes into a space between TrkB and the Heavy Chain of the 1G11 Fab (see FIG. 5). The addition of molecular surfaces to the superimposition shows that the VK CDRs L1 and L3, and CDRH3, interact closely with TrkB, and there is a cleft between TrkB and CDRs H1 and H2 which could be envisaged to potentially accommodate the N-terminus of BDNF (see FIG. 6). Binding of 1G11 to TrkB in the presence of BDNF thus may also include binding to the N-terminus of BDNF, and this binding possibly stabilises the ternary complex leading to potentiation of the BDNF functional response. 1G11 thus may, in addition to TrkB, also be able to interact with the N-terminus of the ligand (BDNF/NT-4). Alternatively, 1G11 may stabilise the interaction between TrkB and the ligand, by binding not at the ligand binding site, but close to it.

The residues involved in the paratope were identified by analysis of the co-crystal structure by proximity analysis (using a distance cut-off of 4.5 Å) and by defining residues interacting with the epitope using CCG (Chemical Computing Group) MOE v2015.1001 (Molecular Operating Environment). The main binding residues in the paratope are within CDRs L1 (bold residues represent those approaching the epitope within 4.5 Å, underlined residues represent those that interact directly or indirectly (via water) with the epitope: RASQRISNNLH/SEQ ID NO:3), L3 (bold residues represent those approaching the epitope within 4.5 Å, underlined residues represent those that interact directly or indirectly (via water) with the epitope: QQSNSWPLT/SEQ ID NO:5) and H3 (bold residues represent those approaching the epitope within 4.5 Å, underlined residues represent those that interact directly or indirectly (via water) with the epitope: RGYEGALDY/SEQ ID NO:8). There are only two residues in CDRH2 approaching the epitope within 4.5 Å and only one direct interaction (bold residues represent those approaching the epitope within 4.5 Å, underlined residues represent those that interact directly or indirectly (via water) with the epitope: RIAPGNTYYNEIFKG/SEQ ID NO:7). There is only and a single residue in CDRH1 that approaches or (indirectly) contacts the epitope (bold residues represent those approaching the epitope within 4.5 Å, underlined residues represent those that interact directly or indirectly (via water) with the epitope: SYYIN/SEQ ID NO:6) and a single residue in CDRL2 that approaches the epitope (bold residues represent those approaching the epitope within 4.5 Å, underlined residues represent those that interact directly or indirectly (via water) with the epitope: YVSQSIS/SEQ ID NO:4). Therefore, from a ranking point of view, CDRs L1, L3 and H3 are most important for binding, followed by CDRH2, then CDRL2 and CDRH1.

2.3 Epitope of 3A3

Figure 7:
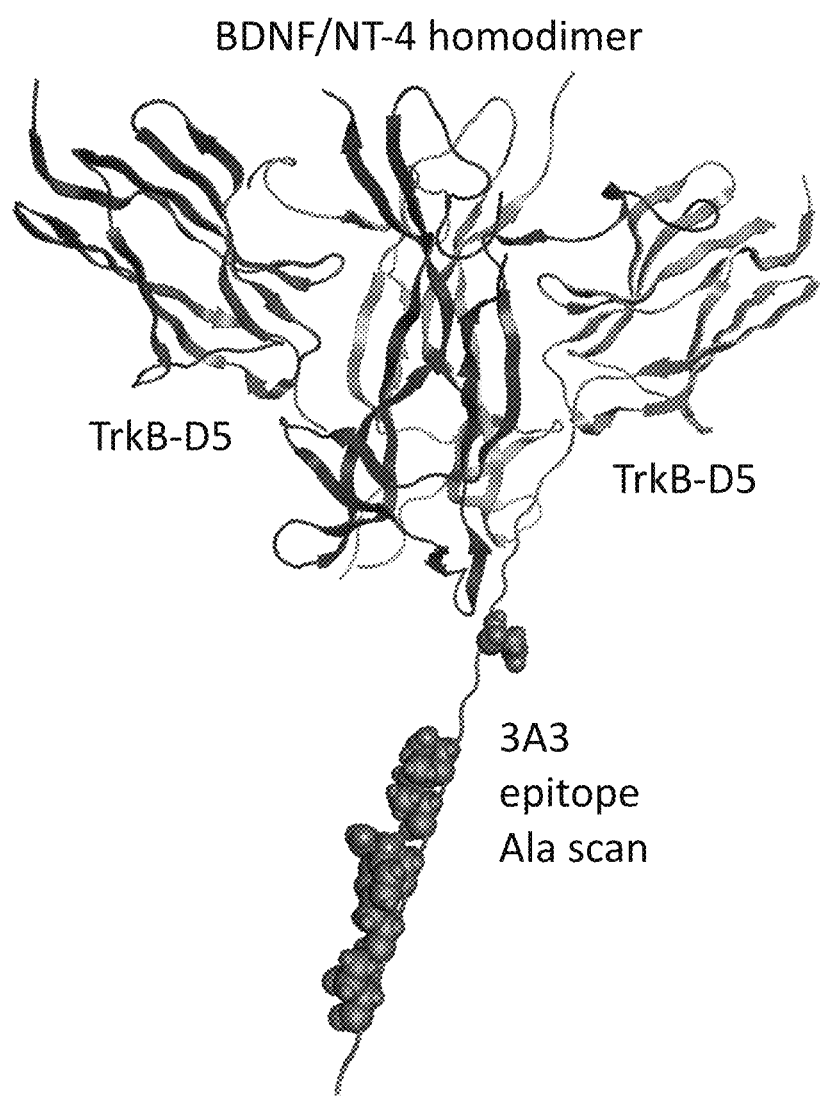
FIG. 7: structural interactions between the BDNF/NT-4 homodimer and two TrkB D5 domains and 3A3. The residues identified by alanine scanning are shown, which are all in the JM region (C-terminal to the D5 domain and N-terminal to the transmembrane region). The JM residues were extended using beta-strand geometry.

Surface plasmon resonance binding analysis of 3A3 with ~80 single point alanine mutants in TrkB-ECD, mostly in the D4-D5-JM domain, identified 9 amino acids as critical residues for binding, although to varying extents (E398, Y397, D399, Y400>D394, I396>V395, N389, T402). This data is summarized in Table 5. These residues are all in the JM region, which is C-terminal to the D5 domain of TrkB and N-terminal to the transmembrane region (see FIG. 7—JM residues were extended using beta-strand geometry). This juxta-membrane (JM) region is, in the absence of any crystal structure, assumed to be a long flexible linker region. It is thought that the JM region may also be important for binding to the ligand.

Although the TrkB epitope to which 3A3 binds appears to be distinct to the epitope for 1G11, it is important to note that 3A3 competes with 1G11 (and 8E5) for binding to TrkB, and therefore the epitopes may be overlapping in some way (see Example 1.6 above) or binding to JM or D5 domain may result in a conformational change that alter the binding epitope for the other antibody. It is possible that the long flexible linker of the juxta-membrane (JM) region may actually be in close proximity to the D5 beta sheets A, B and G.

3A3 also shows potentiation of BDNF induced agonism of TrkB (see Example 1.7 above). There is thus a possibility that when 3A3 binds to TrkB, it too may have some additional interactions with BDNF/NT-4 (for example via the N-terminus of the ligand), and/or similarly stabilises the complex of receptor plus ligand.

Interestingly, the study revealed that residues D394, I396, and Y400 in the juxta-membrane region confer human TrkB receptor specificity because these residues are different in rat TrkB (Glu, Leu, Trp respectively), and 3A3 does not activate rat TrkB.

2.4 Epitope of 8E5

No alanine scan mutagenesis or crystallography studies have been carried out to determine the binding epitope for 8E5. However, it is important to note that 8E5 competes with 1G11 (and 3A3) for binding to TrkB, and therefore the epitopes may be overlapping in some way (see Example 1.6 above), or binding to JM or D5 domain may result in a conformational change that alters the binding epitope for the other antibody. 8E5 also shows potentiation of BDNF induced agonism of TrkB (see Example 1.7 above). The fact that 8E5 is human TrkB specific, similar to 3A3, implies that the epitope is likely to be in the JM region, similar to 3A3, where the sequence is diverse between rodent and human (see Table 5).

2.5 Epitope of 5D11

Figure 8:
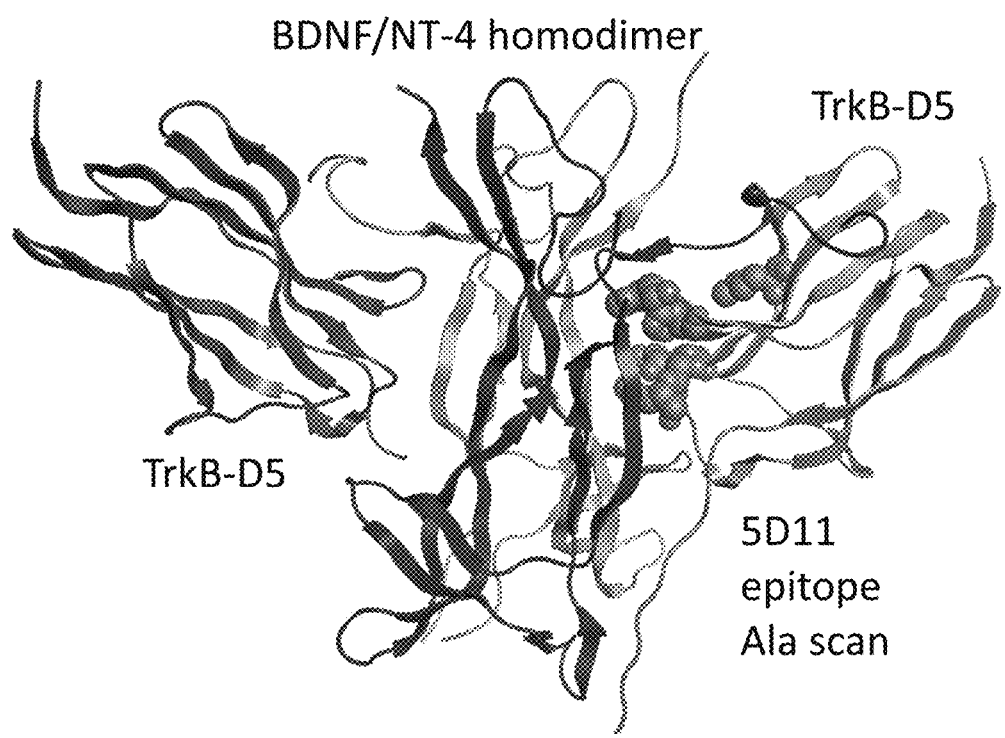
FIG. 8: structural interactions between the BDNF/NT-4 homodimer and two TrkB D5 domains and 5D11. The residues identified by alanine scanning are shown, which are at the ligand binding site.

Surface plasmon resonance binding analysis of 5D11 with ~80 single point alanine mutants in TrkB-ECD, mostly in the D4-D5-JM domain, identified 6 amino acids as critical residues for binding, although to varying extents (N350>H299, D349>H300, K328, K333). This data is summarised in Table 5. FIG. 8 shows that the epitope for 5D11 is at the ligand binding site (the loops between AB, C'D and EF beta sheets of the D5 domain; and the D beta sheet). This is entirely in agreement with the fact that 5D11 competes with BDNF as measured in TrkB phosphorylation assay.

(a) increase the available cell surface levels of TrkB to be activated by the antibody; and/or (b) inhibit activated TrkB receptor endocytosis and degradation.

SEC-MALS was conducted to evaluate the formation of binary complexes of a soluble truncated form of the ECD of TrkB (TrkB_H284-H430 ECD-6H) with 3A3 or 1G11 or BNDF. The presence of binary complexes could be detected in all cases. SEC-MALS was also used to evaluate whether a ternary complex was formed between this construct of TrkB with BDNF and 3A3, and/or between TrkB, BDNF and 1G11. The TrkB, BDNF and 3A3 experiment provided no clear evidence of the presence of a ternary complex. No binary or ternary complexes could be detected in this experiment, suggesting complicated solution behaviour and the possibility of formation of higher order species not visible by SEC-MALS. The data from the TrkB, BDNF and 1G11 experiment also suggested formation of higher than simple binary complexes. In this instance some of these larger than simple binary species could be detected. However, the constituents of these higher molecular weight species could not be accurately determined. Thus it remains possible that potentiation by both antibodies may result from the formation of a ternary complex.

TABLE 5

Epitope summary

| Agonist Ab | Residues identified by alanine scanning mutagenesis | Residues identified by X-ray crystallography proximity analysis and interaction analysis (bold: same as alanine scanning) | TrkB epitope | (a) BDNF competition (b) BDNF interaction/ stabilisation |
|---|---|---|---|---|
| 1G11 | F291, E293 > K372, E210, T288, D370 > F285, T290 | T288, F291, K372, E293, I289, T290, L292, S294, E371, Q373, I374, S375, K308, D358, E341 | D5 beta sheet A, region between beta sheets A and A', D5 beta sheet G; Not ligand binding site | (a) No (b) Possibly via N-terminus of BDNF |
| 3A3 | E398, Y397, D399, Y400 > D394, I396 > V395, N389, T402 | ND | Juxta-membrane region; Not ligand binding site | a) No (b) Possibly via N-terminus of BDNF |
| 8E5 | ND | ND | Presume juxta-membrane region; Not ligand binding site | a) No (b) Possibly via N-terminus of BDNF |
| 5D11 | N350 > H299, D349 > H300, K328, K333 | | D5, ligand binding site | (a) Yes (b) No |

ND: not determined

2.6 Potentiating Antibodies

Based on the results from Examples 1 and 2, there are (i) TrkB agonists which bind to TrkB epitopes that are in close proximity to the BDNF binding site of TrkB, in particular close to the specificity patch that binds to the N-terminus of the ligand, and allow for binding to TrkB which is either enhanced or stabilised in the presence of BDNF/NT-4: these are TrkB-BDNF potentiators; (ii) TrkB agonists that bind within or in close proximity to the ligand binding site, and destabilise the interactions between receptor and ligand: these are BDNF competitors; and (iii) TrkB agonists that bind to epitopes away from the BDNF binding site that are simple agonists with no potentiating function.

1G11, 3A3 and 8E5 are exemplars of potentiators which are non-competitive with BDNF and which appear to bind to two epitopes (8E5 epitope not yet determined). It is possible that binding to these epitopes stabilises the TrkB receptor in an active conformation in the presence of BDNF, and also

2.6 Hydrogen Deuterium Exchange

HDX-MS was used to monitor the exchange rates of his tagged D5-JM TrkB in the presence or absence of a number of other potential protein partners. The following protein solutions were prepared by diluting the individual components into a non-deuterated H$_2$O buffer of 50 mM Na phosphate, 150 mM NaCl pH 7.0:

TrkB_MPLLLLLPLLWAGALAG_H284-H430(D5-JM)-5His (20 µM)

TrkB_MPLLLLLPLLWAGALAG_H284-H430(D5-JM)-5His (20 µM); 1G11 mAb (40 µM; to ensure all TrkB is present in a binary complex)

TrkB_MPLLLLLPLLWAGALAG_H284-H430(D5-JM)-5His (20 µM); 3A3 mAb (40 µM; to ensure all TrkB is present in a binary complex)

TrkB_MPLLLLLPLLWAGALAG_H284-H430(D5-JM)-5His (20 µM); BDNF (40 µM; to ensure all TrkB is present in a binary complex)

TrkB_MPLLLLLPLLWAGALAG_H284-H430(D5-JM)-
5His (20 μM); 1G11 mAb (20 μM); BDNF (20 μM)
TrkB_MPLLLLLPLLWAGALAG_H284-H430(D5-JM)-
5His (20 μM); 3A3 mAb (20 μM); BDNF (20 μM)

The HDX labelling reaction was carried out using a standard HDX method with a 20 fold dilution from non-deuterated into deuterated buffer (50 mM Na phosphate, 100 mM NaCl in D20, pH 6.6) at ambient temperature. Exchange samples (1-3 replicates) were taken at 4 time points: 0 seconds (i.e. on dilution into non-deuterated buffer), 15 seconds; 60 seconds and 300 seconds. The samples were quenched with a pre-chilled low pH and denaturing quench buffer (400 mM sodium phosphate, 8 M guanidine HCl, 500 mM (tris(2-carboxyethyl)phosphine), pH 2.2) at 4° C.

The denatured quenched samples were injected onto an immobilised pepsin digestion column (Waters Enzymate BEH, 2.1 mm×30 mm, Part no: 186007233) with a 240 second digestion time, a column flow rate of 100 μl/min and digest buffer of 0.2% aqueous formic acid at 15° C. The released peptides were analysed by a UPLC-MS at 0° C. on a Acquity UPLC system using a 1.0×100 mm UPLC BEH C18 column (Part no 186002346) with typically a 15 minute run time and mobile phase A: $H_2O$/formic acid (99.8:0.2 v/v) and mobile phase B: ACN/formic acid (99.8:0.2 v/v) at a flow rate of 40 μl/min.

Peptides produced by proteolysis of the non-deuterated proteins were identified using a ProteinLynxGlobal SERVER (http://www.waters.com/waters/en_GB/ProteinLynx-Global-SERVER %28PLGS %29/nav.htm?cid=513821&locale=en_GB), or a Mascot search engine, against a database containing only the protein sequences of interest. The deuterium incorporation for each time point and state was calculated using DynamX Analysis Software v 3.0 (or HD Examiner) by comparing the undeuterated peptide list imported from PLGS to the data acquired for the deuterated samples[1].

Deuteration data for each peptide were manually assessed and charge states or peptides giving poor quality data were removed from the analysis.

Results

Figure 9:
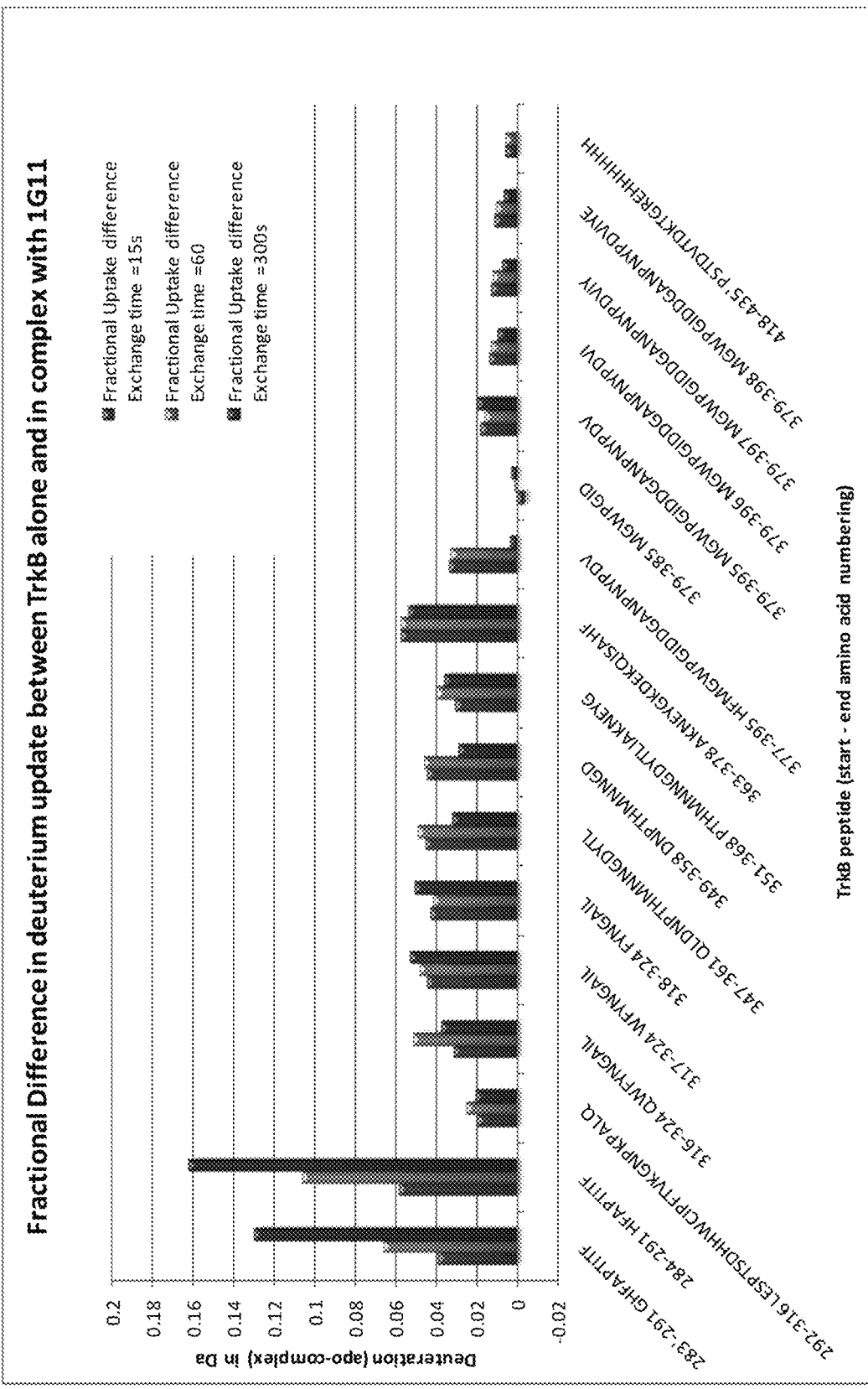
FIG. 9 shows the fractional difference in deuterium update between TrkB peptides derived from MPLLLLLPLLWA-GALAG_H284-H430(D5-JM)-5His alone or in complex with 1G11.

TrkB in the presence of 1G11 showed significant changes in the profile of deuterium exchange rates observed for TrkB peptides. The fractional deuteration update difference plot (FIG. 9), shows strongest deuteration protection for the TrkB peptide region 284-291. This remains strongly protected over all time points investigated suggesting this region is likely to be important for the interaction of TrkB with 1G11. More subtle exchange protection was seen throughout the central region of TrkB approximately 316-380 suggesting additional residues here may play a role in the interaction.

Figure 10:
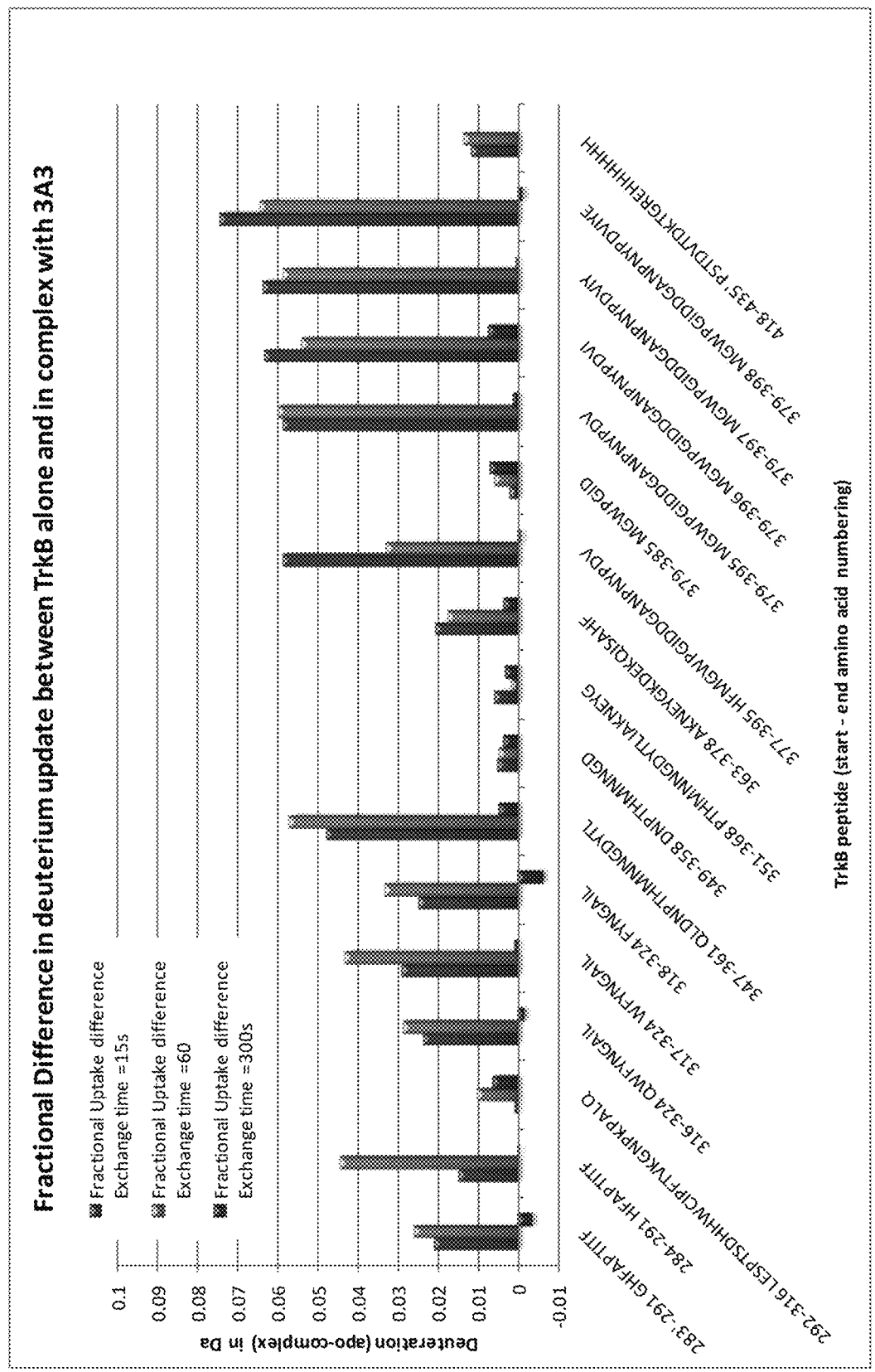
FIG. 10 shows the fractional difference in deuterium update between TrkB peptides derived from MPLLLLLPLLWAGALAG_H284-H430(D5-JM)-5His alone or in complex with 3A3.

TrkB in the presence of 3A3 showed significant changes in the profile of deuterium exchange rates observed for TrkB peptides but only at the earliest exchange time points of 15 and 60s. The fractional deuteration update difference plot (FIG. 10), shows strongest deuteration protection for TrkB peptides containing the region 385-398. However this protection is lost at an exchange time point of 300s. Together with the very rapid deuteration of this region for TrkB, this data suggests that this region may be solvent-exposed and is rapidly deuterated; protection from deuteration through interaction with 3A3 is incomplete and while the rate is slowed, even this slower rate allows saturating deuteration to be reached within 300s.

TrkB alone; TrkB-3A3 mAb; TrkB-1G11 mAb in the presence of BDNF. Addition of BDNF, either to TrkB alone or to TrkB-mAb complexes, did not give robust changes in TrkB deuteration so it was not possible to show either the presence or absence of TrkB-mAb-BDNF ternary complexes.

3. Humanised 1G11, 3A3, 5D11

3.1 Humanisation

1G11, 3A3 and 5D11 were humanised. The sequences are as follows:

Humanised 1G11 variable heavy (VH) region—SEQ ID NO: 40; variable light (VL) region-SEQ ID NO: 41; heavy chain (HC)—SEQ ID NO: 42; light chain (LC)—SEQ ID NO: 43; DNA encoding the HC—SEQ ID NO: 44; DNA encoding the LC—SEQ ID NO: 45.

Humanised 3A3 variable heavy (VH) region—SEQ ID NO: 46; variable light (VL) region-SEQ ID NO: 47; heavy chain (HC)—SEQ ID NO: 48; light chain (LC)—SEQ ID NO: 49; DNA encoding the HC—SEQ ID NO: 50; DNA encoding the LC—SEQ ID NO: 51.

Humanised 5D11 variable heavy (VH) region—SEQ ID NO: 52; variable light (VL) region-SEQ ID NO: 53; heavy chain (HC)—SEQ ID NO: 54; light chain (LC)—SEQ ID NO: 55; DNA encoding the HC—SEQ ID NO: 56; DNA encoding the LC—SEQ ID NO: 57.

The murine CDRs of the heavy and light chains were grafted onto suitable human framework sequences using standard procedures in the art: search of the CDR-masked variable (V) region sequences on the human V gene germline databases, V and J gene template sequences selected based on sequence similarity. Potential back-mutations were identified based on the comparison between human and mouse.

Murine CDRs of the heavy chain of 1G11 were grafted onto the IGHV1_69 heavy chain framework and three humanised heavy chain variants were generated: one which was a straight graft of the CDRs (H0), a second variant which incorporated a back mutation at kabat position 47 (W47C) (H4) and a third variant which incorporated a serine residue at position 47 (W47S) (H7).

Murine CDRs of the light chain of 1G11 were grafted onto the IGKV3_11 human framework (Lo1); and onto the IGKV3D-15 human framework with a single back-mutation of tyrosine at Kabat position 49 to lysine (Y49K) (Ln1).

The humanised variants of 1G11 were generated and tested for binding to TrkB-ECD and in various functional assays. The Ln1 variants showed no significant difference in binding compared to the Lo1 variants.

However, the variants with the human framework residue tryptophan at Kabat position 47 (W47) of the heavy chain, just before CDRH2, had significant loss of binding to TrkB. Tryptophan at Kabat position 47 of the heavy chain is 100% conserved in human antibodies and is at the heavy chain-light chain interface. When W47C/S back-mutations were introduced, binding to TrkB was restored. Cysteine and serine are similar sized amino acids, and both mutants retained binding and functional properties of the humanised 1G11 similar to that of the murine parental 1G11. It is therefore expected that other similar sized amino acids at position 47 of the heavy chain would also retain binding and function. For example, other possible substitutions include Gly, Ala, Val, Thr or Asn. It is also expected that if tryptophan was maintained at position 47 of the heavy chain, there could be other framework changes that would restore the heavy chain-light chain interface structure and therefore restore binding to TrkB.

Humanised 1G11 is a straight graft of the 1G11 CDRs onto human frameworks with incorporation of a serine mutation in the variable heavy chain at Kabat position 47 (H7, Lo1). Humanised 1G11 contains a human IgG1 Fc region modified with mutations L235A and G237A (EU numbering). This modification of the IgG1 Fc region diminishes mAb binding to Fcγ receptors and C1q, therefore reducing the potential of the mAb to induce depletion of TrkB positive cells by antibody-dependent cytotoxicity (ADCC) or complement dependent cytotoxicity (CDC). This is commonly described as Fc-disablement.

Humanised 1G11 was assessed for its ability to bind to C1q and various human and cynomolgus monkey Fc receptors (FcRn, FcγR I, FcγR IIaH, FcγR IIaR, FcγR IIb, FcγR IIIaV and FcγR IIIaF) by surface plasmon resonance. The results demonstrated that, as anticipated, introduction of the Fc disabling L235A and G237A mutations in the heavy chain did not affect the binding of humanised 1G11 to FcRn, but did diminish binding to C1q, FcγR I, FcγR IIaH, FcγR IIaR, FcγR IIb, FcγR IIIaV and FcγR IIIaF.

It should be noted that humanised 1G11 is Fc-disabled whereas the murine 1G11 is not. Fc effector function is not critical to the biological function of this TrkB agonist.

3.2 Humanised Antibody Properties

Humanised 1G11 was compared to the murine 1G11 in a number of assays including surface plasmon resonance to measure binding affinity of the antibodies to TrkB, as well as in TrkB phosphorylation assays. In these assays humanised 1G11 was comparable to 1G11 confirming that humanisation was successful. Humanised 1G11 bound to recombinant human and cynomolgus TrkB-ECD with an affinity of ~55 nM and ~60 nM, respectively, in a 1:1 binding mode as measured by surface plasmon resonance. Humanised 1G11 activated human TrkB receptor in CHO-K1 cells stably overexpressing the human full length TrkB receptor, with the EC50 of 0.65±0.14 nM (Mean±SD, n=3) determined by measuring the levels of phosphorylated TrkB. Humanised 1G11 selectively activated the human TrkB receptor, but not the human TrkA or TrkC receptors; and also cross-reacts with and activates rodent (murine, rat), cynomolgus and human TrkB receptors.

Humanised 1G11 did not compete with BDNF; and it activated human TrkB in CHO-K1 cells with an $EC_{50}$ of 0.65±0.14 nM (Mean±SD, n=3); retained the property of potentiation (~120% vs BDNF) i.e. enhancing the levels of TrkB activation in the presence of saturating concentrations of BDNF.

In vitro, humanised 1G11 enhanced TrkB mediated cell survival in the rat PC12 neuroblastoma cells stably expressing human full length TrkB receptor in a concentration-dependent manner with an average $EC_{50}$ of 0.007±0.003 nM (mean±S.D.; 1G11=0.025±0.01 nM). In the same rat PC12 neuroblastoma cells stably expressing human full length TrkB receptor humanised 1G11 enhanced TrkB mediated neurite outgrowth in a concentration-dependent manner with an average $EC_{50}$ of 0.07±0.02 nM (mean±S.D.; 1G11=0.19±0.06 nM).

4. In Vivo Effects

SRA Rat Model of Neuronal Survival

The in vivo effect of 1G11 on neuronal survival was evaluated in a rat model of avulsion (unilateral) induced spinal motor neuron degeneration. Briefly, the ventral root from the lumbar segment 4 (L4) was avulsed in young adult sprague-dawley rats by surgery and allowed to recover for 1 week before intervention with 1G11 either intravenously (as single bolus) or intrathecally (continuous). For continuous intrathecal infusion, a catheter was inserted into the subarachnoid cavity through the intervertebral hole between L4-L5 with the other end connected to alzet 2002 miniosmotic pump which was implanted subcutaneously at the back of the neck. Until antibody intervention, vehicle formulation was loaded to the pump and delivered at the rate of 0.5 µl/hr.

Continuous intrathecal infusion of 2 different doses of 1G11(60 µg or 240 µg/day) or BDNF (positive control; 12 µg/day), but not vehicle formulation (negative control) in the rat SRA model for 2 weeks enhanced the survival of ChAT expressing neurons (stained with anti-ChAT antibody) to a similar extent (i.e. compared to the contralateral side) with no distinct dose-dependent response compared to vehicle treated group. Intravenous administration of 1G11 (0.03, 0.1, 0.3, 1, 3, 30 mg/kg) or BDNF (positive control; 12 µg/day) 1 week post-nerve root avulsion, but not isotype control (IgG1, 3 mg/kg) or vehicle formulation (negative control), showed an exposure-dependent enhancement of spinal neuron survival as visualised by ChAT staining. 1G11 was able to rescue ChAT⁺ neurons to different extent at 1, 3, and 30 mg/kg with negligible effect at ≤0.3 mg/kg.

In summary, 1G11, when administered either as a single bolus intravenous tail vein injection or by continuous intrathecal infusion, 7 days post-injury in the unilaterally (L4 ventral root) avulsed rats, enhanced the survival of spinal cord ChAT⁺ neurons.

Gait function (hSOD1$^{G93A}$ mice)

In addition to the effect of 1G11 on neuronal survival (as described above), the functional effect of 1G11 was investigated in the congenic B6Cg-Tg(hSOD1$^{G93A}$)1Gur/J transgenic mice. The hSOD1 Tg mice display impairment in various gait parameters as the disease develop and progress. 1G11 (0.3 mg/kg), but not the vehicle formulation (negative control), when administered through tail vein bolus injection every 2 weeks for 28 days (twice during the intervention period) in a cohort of females (~3.5 months old) significantly improved the gait features in hSOD1 mice compared to hSOD1-vehicle control to different extent: run speed, cadence (steps/second), stride time, and stance time almost comparable to that in wild type littermates; relatively moderate effect on stride length; and much reduced effect on swing speed. These results indicate that 1G11 when administered intravenously could ameliorate gait deficits in hSOD1$^{G93A}$ transgenic mice.

To further evaluate the effect of 1G11 on gait and neurological score, mice (males and females, approximately 3.5 months old, at least 16 mice of each gender per group at the beginning of the study) were dosed in accordance with table 6. The experiment was performed in a randomized, placebo and isotype controlled, and double blinded manner.

TABLE 6

| Cohort | Animals | Therapeutic | Administration Route | Dosing Regimen |
|---|---|---|---|---|
| A | Wild type | Vehicle | iv, bolus, tail vein | 4 doses, 14 days between doses |
| B | hSOD1-G93A | Mouse 1gG1 isotype control (1 mg/kg in vehicle) | iv, bolus, tail vein | 4 doses, 14 days between doses |
| C | hSOD1-G93A | 1G11 (0.3 mg/kg in vehicle) | iv, bolus, tail vein | 4 doses, 14 days between doses |
| D | hSOD1-G93A | 1G11 (1 mg/kg in vehicle) | iv, bolus, tail vein | 4 doses, 14 days between doses |

TABLE 6-continued

| Cohort | Animals | Therapeutic | Administration Route | Dosing Regimen |
|---|---|---|---|---|
| E | hSOD1-G93A | Vehicle | iv, bolus, tail vein | 4 doses, 14 days between doses |

Vehicle = 20 mM Phosphate Buffer, 130 mM NaCl pH 6.0, and 0.005% Polysorbate 20
iv = intravenous,
ip = intraperitoneal Animals were subjected to gait analysis using the rodent CatWalk System at 8 time points: Day 97 (baseline), Day 99 (1 d post $1^{st}$ dose), Day 111 (13 d post $1^{st}$ dose), Day 113 (1 d post $2^{nd}$ dose), Day 125 (13 d post $2^{nd}$ dose), Day 139 (13 d post $3^{rd}$ dose), Day 146 (7 d post $4^{th}$ dose) and on Day 153 (13 d post $4^{th}$ dose). Six kinds of gait parameters (run speed, stride length, stance time, stride time, cadence and swing speed) were selected for the analysis. Results showed that 1G11 significantly improved the gait features in hSOD1-G93A mice compared to IgG1 isotype control for both genders, especially at Day 125 and Day 139. On average, there was a better improvement in gait features in high dose group, compared to low dose group.

Neurological score was monitored for all hSOD1-G93A animals throughout the whole study time period. Log-Rank tests showed that relative to lgG1 isotype control, both 1 mg/kg and 0.3 mg/kg 1G11 delayed the median time to death noticeably for female mice. For male mice, 0.3 mg/kg of hSOD1-1G11 group delayed the median time to death noticeably while 1 mg/kg of hSOD1-1G11 groups did not show much improvement relative to the IgG1 isotype control. Wilcoxon tests showed for female mice, 1 mg/kg 1G11, but not 0.3 mg/kg 1G11, delayed the median time to tremor onset noticeably, relative to the IgG1 isotype control. Both 1 mg/kg and 0.3 mg/kg 1G11 delayed the median time to tremor onset marginally in male mice relative to the IgG1 isotype control.

In summary, these results indicate that 1G11 when administered intravenously could ameliorate gait deficits in both genders of hSOD1-G93A transgenic mice, delay tremor onset in both genders and improve overall 'survival' only in females of hSOD1-G93A transgenic mice.

Motor Neuron Survival (hSOD1$^{G93A}$ mice)

To evaluate the effect of 1G11 on spinal cord ChAT positive neurons, male mice (approximately 50 days old, 12 mice per group at the beginning of the study) were dosed in accordance with table 7. The experiment was performed in a randomized, placebo & isotype controlled, and double blinded manner.

TABLE 7

| Cohort | Animals | Therapeutic | Administration Route | Dosing Regimen |
|---|---|---|---|---|
| A | Wild type | Vehicle | iv, bolus, tail vein | 3 doses, 14 days between doses |
| B | hSOD1-G93A | Mouse 1gG1 isotype control (1 mg/kg in vehicle) | iv, bolus, tail vein | 3 doses, 14 days between doses |
| C | hSOD1-G93A | 1G11 (0.3 mg/kg in vehicle) | iv, bolus, tail vein | 3 doses, 14 days between doses |
| D | hSOD1-G93A | 1G11 (1 mg/kg in vehicle) | iv, bolus, tail vein | 3 doses, 14 days between doses |
| E | hSOD1-G93A | Vehicle | iv, bolus, tail vein | 3 doses, 14 days between doses |

Vehicle = 20 mM Phosphate Buffer, 130 mM NaCl pH 6.0, and 0.005% Polysorbate 20
iv = intravenous,
ip = intraperitoneal At the end of the dosing period, mice were deeply anesthetized with isoflurane. Mice were transcardially perfused with ice cold 0.9% saline (120 mL) to drain the blood followed by 60 mL of 4% Paraformaldehyde (PFA). The spinal cord was collected and post-fixed for 24 hours in 4% PFA at 4° C. Immunohistochemistry (IHC) of Choline acetyltransferase (ChAT) was performed on an IHC autostainer (Ventana Discovery Ultra, Roche, USA). Whole slide images were captured by ScanScope XT (Leica Biosystems, USA).

ChAT positive cells in L3-L5 of lumbar spinal cord were quantified and analyzed. In order to count the neurons accurately, hematoxylin channel was separated from DAB (ImageScope, version 11, Leica Biosystem) and then DAB only images (10×) covering whole ventral spinal cord was taken for cell quantification. ChAT positive MN neurons were manually counted by an independent observer in a blinded manner. To eliminate bias and ensure consistency, image quantification was randomly checked for quality by another independent investigator.

Lumbar spinal cord (L3-L5) analysis by ChAT immunostaining showed a highly significant reduction of ChAT positive motor neurons in vehicle treated hSOD1-G93A transgenic mice compared to vehicle treated wild type mice (35% reduction, $p<0.0001$). These data indicate obvious degeneration of motor neurons in the spinal cord of hSOD1-G93A mice, compared with wild type mice. Mouse IgG1 (172.6±31.10) and 1G11 treatment groups did not demonstrate statistical significance over vehicle, (0.3 mg/kg: 169.1±17.25; 1 mg/kg:160.1±28.12).

The invention claimed is:

1. A method of treating sensorineural hearing loss in a subject in need thereof, comprising administering to said subject a therapeutically effective amount of a TrkB agonist antibody comprising a heavy chain variable region and a light chain variable region, wherein the heavy chain variable region comprises complementarity determining region (CDR) H1, CDRH2, and CDRH3 of SEQ ID NO: 6, SEQ ID NO: 7, and SEQ ID NO: 8, respectively, and the light chain variable region comprises CDRL1, CDRL2, and CDRL3 of SEQ ID NO: 3, SEQ ID NO: 4, and SEQ ID NO: 5, respectively.

2. The method according to claim 1, wherein the sensorineural hearing loss results from acoustic trauma.

3. The method according to claim 1, wherein the sensorineural hearing loss is sensory hearing loss.

4. The method according to claim 1, wherein the sensorineural hearing loss is neural (8th nerve related) hearing loss.

5. The method according to claim 1, wherein the sensorineural hearing loss is hidden hearing loss.

6. The method according to claim 1, wherein the sensorineural hearing loss is tinnitus.

7. The method according to claim 1, wherein the sensorineural hearing loss is presbycusis.

8. The method according to claim 1, wherein the TrkB agonist antibody is used in combination with cochlear implant.

9. The method according to claim 1, wherein the TrkB agonist antibody is used in combination with a steroid.

10. The method according to claim 1, wherein the TrkB agonist antibody is administered by the intracochlear route in a pharmaceutical composition.

11. The method according to claim 1, wherein the TrkB agonist antibody is administered by the transtympanic route in a pharmaceutical composition.

12. The method according to claim 1, wherein the TrkB agonist antibody comprises a light chain variable region comprising SEQ ID NO: 41 and a heavy chain variable region comprising SEQ ID NO: 40.

13. The method according to claim 2, wherein the TrkB agonist antibody comprises a light chain variable region comprising SEQ ID NO: 41 and a heavy chain variable region comprising SEQ ID NO: 40.

14. The method according to claim 3, wherein the TrkB agonist antibody comprises a light chain variable region comprising SEQ ID NO: 41 and a heavy chain variable region comprising SEQ ID NO: 40.

15. The method according to claim 4, wherein the TrkB agonist antibody comprises a light chain variable region comprising SEQ ID NO: 41 and a heavy chain variable region comprising SEQ ID NO: 40.

16. The method according to claim 5, wherein the TrkB agonist antibody comprises a light chain variable region comprising SEQ ID NO: 41 and a heavy chain variable region comprising SEQ ID NO: 40.

17. The method according to claim 6, wherein the TrkB agonist antibody comprises a light chain variable region comprising SEQ ID NO: 41 and a heavy chain variable region comprising SEQ ID NO: 40.

18. The method according to claim 7, wherein the TrkB agonist antibody comprises a light chain variable region comprising SEQ ID NO: 41 and a heavy chain variable region comprising SEQ ID NO: 40.

* * * * *

UNITED STATES PATENT AND TRADEMARK OFFICE
CERTIFICATE OF CORRECTION

| | |
|---|---|
| PATENT NO. | : 11,078,287 B2 |
| APPLICATION NO. | : 15/776493 |
| DATED | : August 3, 2021 |
| INVENTOR(S) | : Bhinder et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 351 days.

Signed and Sealed this
Thirty-first Day of January, 2023

*Katherine Kelly Vidal*

Katherine Kelly Vidal
*Director of the United States Patent and Trademark Office*